(12) United States Patent
Bekkali et al.

(10) Patent No.: US 6,313,117 B1
(45) Date of Patent: Nov. 6, 2001

(54) SUCCINATE DERIVATIVE COMPOUNDS USEFUL AS CYSTEINE PROTEASE INHIBITORS

(75) Inventors: Younes Bekkali, Danbury; Rajashehar Betageri, Bethel; Michel Jose Emmanuel; Eugene Richard Hickey, both of Danbury; Weimin Liu, Shelton; Usha R. Patel, Brookfield; Denice Mary Spero, West Redding; David S. Thomson, Ridgefield; Yancey David Ward, Sandy Hook; Erick Richard Roush Young; Sanxing Sun, both of Danbury, all of CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/627,869

(22) Filed: Jul. 28, 2000

Related U.S. Application Data

(60) Provisional application No. 60/146,647, filed on Jul. 30, 1999.

(51) Int. Cl.[7] .......................... A61K 31/5355; A61P 9/10; C07D 295/185; C07D 413/12

(52) U.S. Cl. ..................... 514/235.5; 544/130; 544/141; 544/143; 544/163; 548/309.7

(58) Field of Search .................................. 544/141, 163, 544/130; 514/235.5

(56) References Cited

FOREIGN PATENT DOCUMENTS

99/24460   5/1999   (WO).
99/56765   11/1999  (WO).

*Primary Examiner*—Robert W. Ramsuer
(74) *Attorney, Agent, or Firm*—Robert P. Raymond; Anthony P. Bottino; Alan R. Stempel

(57) ABSTRACT

Disclosed are novel succinate derivative compounds of the formula(I)/(Ia):

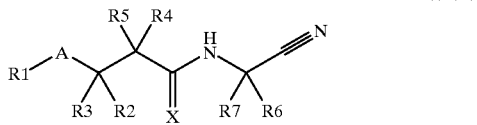

wherein R1, R2, R3, R4, R5, R6, R7, X and A are defined herein. The compounds are useful as inhibitors of cysteine proteases. Also disclosed are methods of using and methods of making such compounds.

27 Claims, No Drawings

SUCCINATE DERIVATIVE COMPOUNDS USEFUL AS CYSTEINE PROTEASE INHIBITORS

RELATED APPLICATION DATA

This application claims benefit to U.S. provisional application No. 60/146,647 filed Jul. 30, 1999.

TECHNICAL FIELD OF THE INVENTION

This invention relates to peptidyl cysteine protease inhibitors. The compounds are reversible inhibitors of the cysteine proteases S, K, F, L and B and are therefore useful in the treatment of autoimmune and other cathepsin related diseases. The invention also discloses processes for preparing such compounds and pharmaceutical compositions comprising them.

BACKGROUND OF THE INVENTION

Cathepsin S and cathepsin K are members of the papain family, within the papain superfamily of cysteine proteases. The papain family is the largest group of cysteine proteases and includes proteases such as cathepsins B, H, K, L, O and S. (A. J. Barrett et al., 1996, Perspectives in Drug Discovery and Design, 6, 1). The cysteine proteases have important roles in human biology and diseases including atherosclerosis, emphysema, osteoporosis, chronic inflammation and immune disorders (H. A. Chapman et al., 1997, Ann. Rev. Physiol., 59, 63). Cathepsin S plays a key role in regulating antigen presentation and immunity (H. A. Chapman, 1998, Current Opinion in Immunology, 10, 93; R. J. Riese et al., 1998, J. Clin. Invest., 101, 2351; R. J. Riese et al., 1996, Immunity, 4, 357). Cathepsin S deficient mice have impaired invariant chain degradation resulting in decreased antigen presentation and germinal center formation, and diminished susceptibility to collagen-induced arthritis indicating the therapeutic potential for a cathepsin S inhibitor (G. Shi et al., 1999, Immunity, 10, 197; T. Y. Nakagawa et al, 1999, Immunity, 10, 207).

The specificity of the immune response relies on processing of foreign protein and presentation of antigenic peptide at the cell surface. Antigenic peptide is presented bound to MHC Class II, a heterodimeric glycoprotein expressed in certain antigen presenting cells of hematopoietic lineage, such as B cells, macrophages and dendritic cells. Presentation of antigen to effector cells, such as T-cells, is a fundamental step in recognition of non-self and thus initiation of the immune response.

Recently MHC Class II heterodimers were shown to associate intracellularly with a third molecule designated invariant chain. Invariant chain facilitates Class II transport to the endosomal compartment and stabilizes the Class II protein prior to loading with antigen. Invariant chain interacts directly with Class II dimers in the antigen-binding groove and therefore must be proteolyzed and removed or antigen cannot be loaded or presented. Current research suggests that invariant chain is selectively proteolyzed by cathepsin S, which is compartmentalized with MHC Class II complexes within the cell. Cathepsin S degrades invariant chain to a small peptide, termed CLIP, which occupies the antigen-binding groove. CLIP is released from MHC Class II by the interaction of MHC Class II with HLA-DM, a MHC-like molecule thus freeing MHC Class II to associate with antigenic peptides. MHC Class II-antigen complexes are then transported to the cell surface for presentation to T-cells, and initiation of the immune response.

Cathepsin S, through proteolytic degradation of invariant chain to CLIP, provides a fundamental step in generation of an immune response. It follows that inhibition of antigen presentation via prevention of invariant chain degradation by cathepsin S could provide a mechanism for immuno-regulation. Control of antigen-specific immune responses has long been desirable as a useful and safe therapy for autoimmune diseases. Such diseases include Crohn's disease and arthritis, as well as other T-cell-mediated immune responses (C. Janeway and P. Travers, 1996, Immunobiology, The Immune System in Health and Disease, Chapter 12). Furthermore, cathepsin S, which has broad pH specificity, has been implicated in a variety of other diseases involving extracellular proteolysis, such as Alzheimer's disease (U. Muller-Ladner et al., 1996, Perspectives in Drug Discovery and Design, 6, 87) and atherosclerosis (G. K. Sukhova et al., 1998, J. Clin. Invest., 102, 576).

A cathepsin S inhibitor has been found to block the rise in IgE titers and eosinophil infiltration in the lung in a mouse model of pulmonary hypersensitivity, suggesting that cathepsin S may be involved in asthma (R. J. Riese et al., J. Clin. Investigation, 1998, 101, 2351).

Another cysteine protease, cathepsin F has been found in macrophages and is also involved in antigen processing. It has been postulated that cathepsin F in stimulated lung macrophages and possibly other antigen presenting cells could play a role in airway inflammation (G.-P. Shi et al., J. Exp. Med., 2000, 191, 1177).

Cathepsin K, another cysteine protease has been found to be highly expressed in osteoclasts and to degrade bone collagen and other bone matrix proteins. Inhibitors of cathepsin K have been shown to inhibit bone resorption in mice. Therefore, cathepsin K may play a role in osteoclastic bone resorption and cathepsin K inhibitors may be useful in the treatment of diseases involving bone resorption such as osteoporosis (F. Lazner et al., Human Molecular Genetics, 1999, 8, 1839).

Cysteine proteases are characterized by having a cysteine residue at the active site which serves as a nucleophile. The active site also contains a histidine residue. The imidazole ring on the histidine serves as a base to generate a thiolate anion on the active site cysteine, increasing its nucleophilicity. When a substrate is recognized by the protease, the amide bond to be cleaved is directed to the active site, where the thiolate attacks the carbonyl carbon forming an acyl-enzyme intermediate and cleaving the amide bond, liberating an amine. Subsequently, water cleaves the acyl-enzyme species regenerating the enzyme and liberating the other cleavage product of the substrate, a carboxylic acid.

Inhibitors of cysteine proteases contain a functionality that can react reversibly or irreversibly with the active site cysteine. Examples of reactive functionalities that have been described (D. Rasnick, 1996, Perspectives in Drug Discovery and Design, 6, 47) on cysteine protease inhibitors include peptidyl diazomethanes, epoxides, monofluoroalkanes and acyloxymethanes, which irreversibly alkylate the cysteine thiol. Other irreversible inhibitors include Michael acceptors such as peptidyl vinyl esters and other carboxylic acid derivatives (S. Liu et al., J. Med Chem., 1992, 35, 1067) and vinyl sulfones (J. T. Palmer et al., 1995, J. Med Chem., 38, 3193).

Reactive functionalities that form reversible complexes with the active site cysteine include peptidyl aldehydes (R. P. Hanzlik et al., 1991, Biochim. Biophys. Acta., 1073, 33), which are non-selective, inhibiting both cysteine and serine proteases as well as other nucleophiles. Peptidyl nitriles (R. P. Hanzlik et al., 1990, Biochim. Biophys. Acta., 1035, 62) are less reactive than aldehydes and therefore more selective for the more nucleophilic cysteine proteases. Various reactive ketones have also been reported to be reversible inhibitors of cysteine proteases (D. Rasnick, 1996, ibid). In addition to reacting with the nucleophilic cysteine of the active site, reactive ketones may react with water, forming a hemiketal which may act as a transition state inhibitor.

Examples of cathepsin S inhibitors have been reported. J. L. Klaus et al. (WO 9640737) described reversible inhibitors of cysteine proteases including cathepsin S, containing an ethylene diamine. In U.S. Pat. No. 5,776,718 to Palmer et al. there is disclosed in it's broadest generic aspect a protease inhibitor comprising a targeting group linked through a two carbon atom chain to an electron withdrawing group (EWG). The compounds of the present application are structurally distinct and thus excluded from the U.S. Pat. No. 5,776,718 patent with particular embodiments possessing unexpectedly greater activity than the closest compounds of the prior art. Other examples of cathepsin S inhibitors have been reported by E. T. Altmann et al, (WO 9924460, 1999) which describes dipeptide nitriles asserted to have activity as inhibitors of Cathepsins B, K, L and S. The WO publication does not disclose any compounds possessing a succinate structure.

Additional peptidyl nitriles have been reported as protease inhibitors. For example, both nitriles and ketoheterocycles are described by B. A. Rowe et al. (U.S. Pat. No. 5,714,471) as protease inhibitors useful in the treatment of neurodegenerative diseases. Peptidyl nitriles are reported by B. Malcolm et al. (WO 9222570) as inhibitors of picornavirus protease. B. J. Gour-Salin (Can. J. Chem., 1991, 69, 1288) and T. C. Liang (Arch. Biochim. Biophys., 1987, 252, 626) described peptidyl nitriles as inhibitors of papain A reversible inhibitor presents a more attractive therapy than irreversible inhibitors. Even compounds with high specificity for a particular protease can bind non-target enzymes. An irreversible compound could therefore permanently inactivate a non-target enzyme, increasing the likelihood of toxicity. Furthermore, any toxic effects resulting from inactivation of the target enzyme would be mitigated by reversible inhibitors, and could be easily remedied by modified or lower dosing. Finally, covalent modification of an enzyme by an irreversible inhibitor could potentially generate an antibody response by acting as a hapten.

In light of the above, there is a clear need for compounds which reversibly and selectively inhibit cysteine proteases such as cathepsin S, K, F, L and cathepsin B for indications in which these proteases exacerbate disease.

SUMMARY OF THE INVENTION

It is therefore an object of this invention to provide novel compounds according to the formulas (I) and (Ia) as described herein which reversibly inhibit the cysteine proteases cathepsin S, K, F, L and cathepsin B. It is a further object of the invention to provide methods for treating diseases and pathological conditions exacerbated by these cysteine proteases such as, but not limited, to rheumatoid arthritis, asthma and osteoporosis. It is yet a further object of the invention to provide novel processes for preparation of the above-mentioned novel compounds.

DETAILED DESCRIPTION OF THE PREFERRED EMBODIMENTS

The novel compounds of the invention are derivatives of succinamide and are therefore less peptidic in nature than many of the protease inhibitors described in the prior art. These compounds, then, may exhibit certain advantages over known peptidic like compounds. These advantages may include, for example, increased bioavailability, increased stability, increased half-life and decreased clearance rates.

A proposed mechanism of action of the cysteine protease inhibitors of this invention is that the inhibitors contain a functionality that can react (reversibly or irreversibly) with the active site cysteine. The reactive functionality is attached to a peptide or peptide mimic that can be recognized and accommodated by the region of the protease surrounding the active site. The nature of both the reactive functionality and the remaining portion of the inhibitor determine the degree of selectivity and potency toward a particular protease.

Given the similarity of the active sites in cysteine proteases, it may be anticipated that a given class of inhibitors might have activity against more that one cysteine protease. It may also be expected that due to structural differences between individual cysteine proteases, different compounds of the invention may have different inhibitory potencies against different cysteine proteases. Thus some of the compounds of the invention may also be expected to be most effective in treating diseases mediated by cysteine proteases that they inhibit most potently. The activity of particular compounds disclosed herein against cysteine proteases cathepsin S, K, F, L and cathepsin B may be determined by the screens described in the section entitled "Assessment of Biological Properties."

Accordingly, in the first generic aspect of the invention, there is provided compounds of formula (I):

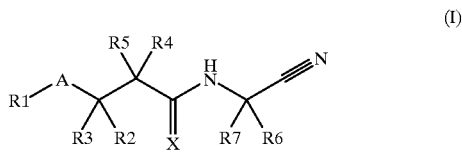

(I)

wherein:

A is —C(O)— or —CH(OR8)—;

R1 is alkyl, cycloalkyl, aryl, heterocyclyl, heteroaryl or amino wherein R1 is optionally substituted by one or more $R_a$;

$R_a$ is selected from the group consisting of alkyl, cycloalkyl, aryl, heterocyclyl, heteroaryl, alkoxy, aryloxy, alkanoyl, aroyl, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio arylthio, ureido wherein either nitrogen atom may be independently substituted by alkyl, aryl, heterocyclyl or heteroaryl, alkoxycarbonylamino, aryloxycarbonylamino, alkylcarbarnoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino; $R_a$ may be further optionally substituted by one or more $R_b$;

$R_b$ is selected from the group consisting of alkyl, cycloalkyl, aryl, heterocyclyl, heteroaryl, arylalkyl, alkoxy, aryloxy, arylalkoxy, alkanoyl, aroyl, amino wherein the nitrogen atom may be independently mono or di-substituted by alkyl, aryl, heterocyclyl or heteroaryl, halogen, hydroxy, oxo, carboxy, cyano, nitro, amidino and guanidino;

R2 is hydrogen, $OR_i$ or lower alkyl;

R3 is hydrogen or lower alkyl;

R4 is hydrogen or lower alkyl;

R5 is hydrogen, alkyl, cycloalkyl, aryl, heterocyclyl or heteroaryl, wherein R5 is optionally substituted by one or more $R_c$;

$R_c$ is selected from the group consisting of alkyl, cycloalkyl, aryl, heterocyclyl, heteroaryl, alkoxy, aryloxy, arylalkoxy, alkoxycarbonyl, aryloxycarbonyl, alkanoyl, aroyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio, arylthio, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, $R_c$ may be further optionally substituted by one or more $R_d$;

$R_d$ is selected from the group consisting of alkyl, cycloalkl, aryl, arylalkyl, alkoxy, aryloxy, arylalkoxy, alkanoyl, aroyl, amino, halogen, hydroxy, oxo, carboxy, cyano, nitro, amidino and guanidino;

R6 is hydrogen or lower alkyl said alkyl being optionally interrupted by 1 to two heteroatoms selected from the group consisting of N,O and S;

R7 is hydrogen, alkyl said alkyl being optionally interrupted by 1 to two heteroatoms selected from the group consisting of N,O and S, cycloalkyl, aryl, heterocyclyl, aryl, heteroaryl or cyano, wherein R7 is optionally substituted by one or more $R_e$;

$R_e$ is selected from the group consisting of alkyl, cycloalkyl, aryl, heterocyclyl, heteroaryl, alkoxy, aryloxy, arylalkoxy, alkanoyl, aroyl, alkoxycarbonyl, aryloxycarbonyl, alkanoyloxy, aroyloxy, heteroarylalkoxy, carbamoyl wherein the nitrogen atom may be independently mono or di-substituted by alkyl, aryl, heterocyclyl or heteroaryl, alkanoylamino, aroylamino, alkylcarbamoyl, arylcarbamoyl, alkylthio, arylthio, arylalkylthio, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, Re may be further optionally substituted by one or more $R_f$;

$R_f$ is selected from the group consisting of alkyl, cycloalkyl, aryl optionally substituted by one or more groups selected from halogen, methyl or methoxy, heterocyclyl, heteroaryl, alkoxy, aryloxy, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylcarbamoyl, arylcarbamoyl, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino;

or R6 and R7 together with the carbon they are attached form a 4 to 7 membered carbocyclic or heterocyclic ring, the carbocyclic or heterocyclic ring being optionally substituted with one or more $R_g$;

$R_g$ is selected from the group consisting of alkyl, cycloalkyl, aryl, heteroaryl selected from the group consisting of furanyl, thienyl, pyrrolyl, imidazolyl and pyridinyl, C1–5 alkanoyl, aroyl, C1–5 alkoxycarbonyl, aryloxycarbonyl, carbamoyl wherein the nitrogen atom may be independantly mono or disubstituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, thiazolyl, imidazolyl, pyridinyl, benzimidazolyl and quinolinyl, C1–5 alkanoylamino, aroylamino, C1–5 alkylthio, arylthio, C1–5 alkylsulfonylamino, arylsulfonylamino, C1–5 alkylaminosulfonyl, arylaminosulfonyl, amino wherein the nitrogen atom may be independently mono or disubstituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_g$ may be further optionally substituted by one or more $R_h$;

$R_h$ is selected from the group consisting of C1–5 alkyl, C3–6 cycloalkyl, aryl optionally substituted by one or more groups selected from halogen, lower alkyl or lower alkoxy, heterocyclyl selected from the group consisting of pyrrolidinyl, piperidinyl, morpholinyl, thiomorpholinyl, piperazinyl, indolinyl, pyranyl and thiopyranyl, heteroaryl selected from the group consisting of furanyl, thienyl pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl and quinoxalinyl, C1–5 alkoxy, aryloxy, amino wherein the nitrogen atom may be independently mono or di-substituted by alkyl, aryl, heterocyclyl selected from the group consisting of pyrrolidinyl, piperidinyl and morpholinyl, or heteroaryl selected from the group consisting of furanyl, thienyl, pyrrolyl and pyridinyl, halogen, hydroxy, oxo, carboxy, cyano, nitro, amidino and guanidino;

R8 is hydrogen, alkyl, cycloalkyl, cycloalkyl-alkyl or aryl-alkyl;

Ri is hydrogen or lower alkyl;

X is O or S and pharmaceutically acceptable salts, esters or tautomers thereof.

Preferred are compounds of the formula (I) wherein:

A is as defined above;

R1 is C1–8 allcyl, C3–7 cycloalkyl, aryl, heterocyclyl selected from the group consisting of pyrrolidinyl, piperidinyl, morpholinyl, thiomorpholinyl, piperazinyl, indolinyl, pyranyl and thiopyranyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrinmidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl and amino wherein R1 is optionally substituted by one or more $R_a$;

$R_a$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio, arylthio, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, pyrazolyl, isothiazolyl, oxadiazolyl, triazolyl, tetrazolyl, thiadiazolyl, pyridinyl, pyridazinyl, pyrimidiazinyl, indolyl, isoindolyl, benzofuranyl benzothienyl, benzimidazolyl, beithazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino; $R_a$ may be further optionally substituted by one or more $R_b$;

$R_b$ is selected from the group consisting of C1–8 alkyl, C3–6 cycloalkyl, aryl, C1–8 alkoxy, aryloxy, halogen, hydroxy, oxo, carboxy, cyano, nitro, amidino and guanidino;

R2 is hydrogen, $OR_i$ or C1–5 alkyl;

R3 is hydrogen or C1–5 alkyl;

R4 is hydrogen or C1–5 alkyl;

R5 is hydrogen, C1–8 alkyl, C3–7 cycloalkyl or aryl wherein R5 is optionally substituted by one or more $R_c$;

$R_c$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, alkanoyl, aroyl, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio, arylthio, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranul, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_c$ may be further optionally substituted by one or more $R_d$;

$R_d$ is selected from the group consisting of C1–8 alkyl, C3–6 cycloalkyl, aryl, arylalkyl, C1–8 alkoxy, aryloxy, arylalkoxy, aroyl, amino, halogen, hydroxy, oxo, carboxy, cyano, nitro, amidino and guanidino;

R7 is hydrogen, C1–8 alkyl said alkyl being optionally interrupted by 1 to two heteroatoms selected from the group consisting of N,O and S, C3–7 cycloalkyl, aryl or cyano, wherein R7 is optionally substituted by one or more $R_e$;

$R_e$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, heteroarylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio, arylthio, arylC1–8 alkylthio, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_e$ may be further optionally substituted by one or more $R_f$;

$R_f$ is selected from the group consisting of C1–8 alkyl, C3–7 cycloalkyl, aryl optionally substituted by one or more groups selected from halogen, methyl or methoxy, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio, arylthio, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino;

or R6 and R7 together with the carbon they are attached form a 4 to 7 membered carbocyclic or heterocyclic ring, the carbocyclic or heterocyclic ring being optionally substituted with one or more $R_g$;

$R_g$ is selected from the group consisting of alkyl, cycloalkyl, phenyl, heteroaryl selected from the group consisting of furanyl, thienyl and pyridinyl, C1–5 alkanoyl, aroyl, C1–5 alkoxycarbonyl, aryloxycarbonyl, carbamoyl wherein the nitrogen atom may be independantly mono or disubstituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, thiazolyl, imidazolyl, pyridinyl, benzimidazolyl and quinolinyl, C1–5 alkylthio wherein the sulfur atom may be oxidised to a sulfoxide or sulfone, arylthio wherein the sulfur atom may be oxidised to a sulfoxide or sulfone, C1–5 alkylaminosulfonyl, arylaminosulfonyl, halogen, hydroxy, oxo, carboxy and cyano, $R_g$ may be further optionally substituted by one or more $R_h$;

$R_h$ is selected from the group consisting of C1–5 alkyl, C3–6 cycloalkyl, aryl optionally substituted by one or more groups selected from halogen, C1–5 alkyl or C1–5 alkoxy, heterocyclyl selected from the group consisting of piperidinyl, morpholinyl and piperazinyl, heteroaryl selected from the group consisting of furanyl, thienyl pyrrolyl, imidazolyl, pyridinyl, pyrimidinyl, pyrazinyl, indolyl, benzimidazolyl, quinolinyl, isoquinolinyl, quinazolinyl, benzoxazolyl and quinoxalinyl, C1–5 alkoxy, aryloxy, amino wherein the nitrogen atom may be independently mono or di-substituted by alkyl, aryl, heterocyclyl selected from the group consisting of piperidinyl and morpholinyl or heteroaryl selected from the group consisting of furanyl, thienyl and pyridinyl, halogen, hydroxy, oxo, carboxy and cyano;

R8 is hydrogen, alkyl, cycloalkyl-alkyl or arylalkyl;

Ri is hydrogen or C1–8 alkyl and

X is O or S.

More preferred are compounds of the formula (I) as described immediately above and wherein:

A is as defined above;

R1 is C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl, indolinyl, pyranyl and thiopyranyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl or amino; wherein R1 is optionally substituted by one or more $R_a$;

$R_a$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl;, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, C1–5 alkoxycarbonyl, aryloxycarbonyl, C1–5 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthio, arylthio, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_a$ may be further optionally substituted by one or more $R_b$;

$R_b$ is selected from the group consisting of C1–5 alkyl, C3–6 cycloalkyl, aryl, C1–5 alkoxy, aryloxy, halogen, hydroxy, oxo, carboxy, cyano, nitro, amidino and guanidino;

R2 is hydrogen, $OR_i$ or C1–3 alkyl;

R3 is hydrogen or C1–3 alkyl;

R4 is hydrogen or C1–3 alkyl;

R5 is hydrogen, C1–5 aLkyl, C3–7 cycloalkyl or aryl wherein R5 is optionally substituted by one or more $R_c$;

$R_c$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthio, arylthio, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl or heteroaryl selected the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, amidino and guanidino, $R_c$ may be further optionally substituted by one or more $R_d$;

$R_d$ is selected from the group consisting of C1–5 alkyl, C3–6 cycloalkyl, aryl, arylalkyl, C1–5 alkoxy, aryloxy, arylC1–5alkoxy, aroyl, amino, halogen, hydroxy, oxo, carboxy, cyano, nitro, amidino and guanidino;

R6 is hydrogen or C1–8 alkyl said alkyl being optionally interrupted by 1 to two heteroatoms selected from the group consisting of N,O and S;

R7 is hydrogen, C1–5 alkyl said alkyl being optionally interrupted by 1 to two heteroatoms selected from the group consisting of N,O and S, C3–7 cycloalkyl, aryl or cyano, wherein R7 is optionally substituted by one or more $R_e$;

$R_e$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5alkoxy, heteroarylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthioarylthioarylC1–5 alkylthio, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_e$ may be further optionally substituted by one or more $R_f$;

$R_f$ is selected from the group consisting of C1–5 alkyl, C3–7 cycloalkyl, aryl optionally substituted by one or more groups selected from halogen, methyl or methoxy, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthio, arylthio, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino;

or R6 and R7 together with the carbon they are attached form a carbocyclic ring selected from the group consisting of cyclopropyl, cyclobutyl, cyclopentyl and cyclohexyl or a heterocyclic ring selected from the group consisting of pyrrolidinyl, piperidinyl, hexahydropyridazinyl, hexahydropyrimidinyl, piperazinyl, pyranyl, thiopyranyl, 1,2-thiazinanyl-1,1-dioxide, 1,2,6-thiadiazinanyl-1,1-dioxide, isothiazolidinyl-1,1-dioxide and imidazolidinyl-2,4-dione, the carbocyclic or heterocyclic ring being optionally substituted with one or more $R_g$;

$R_g$ is selected from the group consisting of alkyl, cycloalkyl, phenyl, heteroaryl selected from the group consisting of furanyl and thienyl, C1–3 alkanoyl, benzoyl, C1–3 alkoxycarbonyl, carbamoyl wherein the nitrogen atom may be independantly mono or disubstituted by C1–5 alkyl, phenyl, heterocyclyl selected from the group consisting of piperidinyl, morpholinyl and piperazinyl or heteroaryl selected from the group consisting of furanyl, thienyl and pyridinyl, C1–3 alkylthio wherein the sulfur atom may be oxidised to a sulfoxide or sulfone, phenylthio wherein the sulfur atom may be oxidised to a sulfoxide or sulfone, C1–5 alkylaminosulfonyl, phenylaminosulfonyl, halogen, hydroxy, carboxy and cyano, $R_g$ may be further optionally substituted by one or more $R_h$;

$R_h$ is selected from the group consisting of C1–3 alkyl, C5–6 cycloalkyl, phenyl optionally substituted by one or more groups selected from halogen, C1–3 alkyl and C1–3 alkoxy, piperidinyl, morpholinyl, piperazinyl, imidazolyl, pyridinyl, pyrimidinyl, pyrazinyl, benzimidazolyl, quinolinyl, isoquinolinyl, C1–3 alkoxy, amino wherein the nitrogen atom may be independently mono or di-substituted by C1–5 alkyl, phenyl, heterocyclyl selected from the group consisting of piperidinyl and morpholinyl or heteroaryl selected from the group consisting of furanyl, thienyl and pyridinyl, halogen, hydroxy, oxo and cyano.

R8 is hydrogen, C1–8 alkyl, C3–6 cycloalkyl-alkyl or aryl C1–3 alkyl; and

Ri is hydrogen or C1–5 alkyl.

Even more preferred are compounds of the formula (I) as desribed immediately above and wherein:

A is as defined above;

R1 is C1–5 alkyl, C3–7 cycloalkyl, phenyl, naphthyl, heterocyclyl selected from the group consisting of piperidinyl, morpholinyl, thiomorpholinyl, piperazinyl, pyranyl and thiopyranyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl or amino wherein R1 is optionally substituted by one or more $R_a$;

$R_a$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, quinolinyl and isoquinolinyl, C1–5 alkoxy, aryloxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl, naphthyl, heterocyclyl selected from the group consisting of pyrrolidinyl, piperidinyl, morpholinyl, piperazinyl and indolinyl or heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio, arylthio, ureido wherein either nitrogen atom may be independently substituted by alkyl or aryl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy, cyano and nitro, $R_a$ may be further optionally substituted by one or more $R_b$;
  $R_b$ is selected from the group consisting of C1–5 alkyl, C3–6 cycloalkyl, aryl, C1–5 alkoxy, aryloxy, halogen, hydroxy, oxo, carboxy and cyano;
R2 is hydrogen, $OR_i$ or methyl;
R3 is hydrogen or methyl;
R4 is hydrogen or methyl;
R5 is C1–5 alkyl, C3–7 cycloalkyl or phenyl wherein R5 is optionally substituted by one or more $R_c$;
  $R_c$ is selected from the group consisting of C1–3 alkyl, C3–6 cycloalkyl, phenyl, naphthyl, heterocyclyl selected from the group consisting of piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxy, aryloxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio, arylthio, ureido wherein either nitrogen atom may be independently substituted by C1–5 alkyl, phenyl, naphthyl, heterocyclyl selected from the group consisting of piperidinyl, morpholinyl and piperazinyl or heteroaryl selected the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 allylsulfonylamino, arylsulfonylamino, C1–5 alkylaminosulfonyl, arylaminosulfonyl, amino wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_c$ may be further optionally substituted by one or more $R_d$;
  $R_d$ is selected from the group consisting of C1–5 alkyl, C3–6 cycloalkyl, aryl, arylC1–5alkyl, C1–5 alkoxy, aryloxy, arylC1–3alkoxy, aroyl, amino, halogen, hydroxy, oxo, carboxy and cyano;
R6 is hydrogen or C1–5 alkyl said alkyl being optionally interrupted by 1 to two heteroatoms selected from the group consisting of N,O and S;
R7 is hydrogen, C1–5 alkyl said alkyl being optionally interrupted by 1 to two heteroatoms selected from the group consisting of N,O and S, C3–7 cycloalkyl, phenyl, naphthyl or cyano, wherein R7 is optionally substituted by one or more $R_e$;
  $R_e$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5alkoxy, heteroarylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio, arylthio, arylC1–5 alkylthio, ureido wherein either nitrogen atom may be independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_e$ may be further optionally substituted by one or more $R_f$;

$R_f$ is selected from the group consisting of C1–5 alkyl, C3–7 cycloalkyl, phenyl optionally substituted by one or more groups selected from halogen, methyl and methoxy, naphthyl optionally substituted by one or more groups selected from halogen, methyl and methoxy, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio, arylthio, ureido wherein either nitrogen atom may be independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano;

or R6 and R7 together with the carbon they are attached form a carbocyclic ring selected from the group consisting of cyclopropyl, cyclobutyl, cyclopentyl and cyclohexyl or a nheterocyclic ring selected from the group consisting of piperidinyl, hexahydropyridazinyl, hexahydropyrimidinyl, piperazinyl, pyranyl and thiopyranyl, the carbocyclic or heterocyclic ring being optionally substituted with one or more $R_g$;

$R_g$ is selected from the group consisting of C1–3 alkyl, C3–6 cycloalkyl, C1–3 alkanoyl, benzoyl, C1–3 alkoxycarbonyl, carbamoyl wherein the nitrogen atom may be independantly mono or disubstituted by C1–5 alkyl, phenyl, heterocyclyl selected from the group consisting of piperidinyl, morpholinyl and piperazinyl or heteroaryl selected from the group consisting of furanyl, thienyl and pyridinyl, halogen, hydroxy, carboxy and cyano, $R_g$ may be further optionally substituted by one or more $R_h$;

$R_h$ is selected from the group consisting of methyl, phenyl optionally substituted by one or more groups selected from halogen, methyl and methoxy, piperidinyl, morpholinyl, piperazinyl, pyridinyl, amino wherein the nitrogen atom may be independently mono or di-substituted by C1–3 aLkyl, phenyl, heterocyclyl selected from the group consisting of piperidinyl and morpholinyl or heteroaryl selected from the group consisting of furanyl, thienyl and pyridinyl, halogen, hydroxy, oxo and cyano;

R8 is hydrogen, C1–5 alkyl, C5–6 cycloalkyl-C1–3-alkyl or benzyl;

Ri is hydrogen or methyl; and

X is O.

Yet even more preferred are compounds of the formula (I) as described immediately above and wherein:

A is as defined above;

R1 is C1–5 alkyl, C3–6 cycloalkyl, phenyl, naphthyl, heterocyclyl selected from the group consisting of piperidinyl, morpholinyl, piperazinyl, pyranyl and thiopyranyl, heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl or amino, wherein R1 is optionally substituted by one or more $R_a$;

$R_a$ is selected from the group consisting of C1–3 alkyl, C3–6 cycloalkyl, phenyl, naphthyl, heterocyclyl selected from the group consisting of pyrrolidinyl, piperidinyl, morpholinyl and piperazinyl, heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, quinolinyl and isoquinolinyl, C1–3 alkoxy, phenoxy, C1–3 alkoxycarbonyl, aryloxycarbonyl, C1–5 alkanoyloxy, aroyloxy, carbamoyl wherein the nitrogen atom may be independently mono or di-substituted by C1–5 alkyl, phenyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio, arylthio, ureido wherein either nitrogen atom may be independently substituted by C1–5alkyl, phenyl or naphthyl, C1–5 alkoxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_a$ may be further optionally substituted by one or more $R_b$;

$R_b$ is selected from the group consisting of C1–3 alkyl, C5–6 cycloalkyl, aryl, C1–3 alkoxy, phenoxy, halogen, hydroxy, oxo, carboxy and cyano;

R2 is hydrogen or $OR_i$;

R3 is hydrogen;

R4 is hydrogen;

R5 is C1–5 alkyl, C3–6 cycloalkyl or phenyl, wherein R5 is optionally substituted by one or more $R_c$;

$R_c$ is selected from the group consisting of C1–3 alkyl, C3–6 cycloalkyl, phenyl, naphthyl, heterocyclyl selected from the group consisting of piperidinyl, morpholinyl and piperazinyl, heteroaryl selected from the group consisting of furanyl, thienyl, thiazolyl, imidazolyl, pyridinyl, indolyl, quinolinyl and isoquinolinyl, C1–5 alkoxy, phenoxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio, phenylthio, ureido wherein either nitrogen atom may be independently substituted by C1–3 alkyl, phenyl or heteroaryl selected the group consisting of furanyl, thienyl, pyrrolyl, oxazolyl, thiazolyl, imidazolyl, pyridinyl and indolyl, C1–5 alkoxycarbonylamino, C1–5 alkylcarbamoyloxy, arylcarbamoyloxy, C1–5 alkylsulfonylamino, arylsulfonylamino, amino wherein the nitrogen atom may be independently mono or di-substituted by C1–3 alkyl, phenyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, $R_c$ may be further optionally substituted by one or more $R_d$;

$R_d$ is selected from the group consisting of C1–5 alkyl, C5–6 cycloalkyl, phenyl, naphthyl, arylC1–3alkyl, C1–5 alkoxy, phenoxy, arylC1–3alkoxy, aroyl, amino, halogen, hydroxy, oxo, carboxy and cyano;

R6 is hydrogen or C1–3alkyl said alkyl being optionally interrupted by 1 to two heteroatoms selected from the group consisting of N,O and S;

R7 is hydrogen, C1–5 alkyl said alkyl being optionally interrupted by 1 to two heteroatoms selected from the group consisting of N,O and S, C3–6 cycloalkyl, phenyl or cyano, wherein R7 is optionally substituted by one or more $R_e$;

$R_e$ is selected from the group consisting of C1–3 alkyl, C3–6 cycloalkyl, phenyl, naphthyl, heterocyclyl selected from the group consisting of pyrrolidinyl, piperidinyl, morpholinyl and piperazinyl, heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxy, aryloxy, arylC1–3alkoxy, heteroarylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl or heteroaryl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, arylthio, arylC1–3alkylthio, ureido wherein either nitrogen atom may be independently substituted by C1–5 alkyl or phenyl, C1–5 alkoxycarbonylamino, C1–5 alkylsulfonylamino, arylsulfonylamino, amino wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, and indolyl, halogen, hydroxy, oxo, carboxy and cyano, $R_e$ may be further optionally substituted by one or more $R_f$;

$R_f$ is selected from the group consisting of C1–3 alkyl, C5–6 cycloalkyl, phenyl optionally substituted by one or more groups selected from halogen and methyl, heterocyclyl selected from the group consisting of pyrrolidinyl, piperidinyl, morpholinyl and piperazinyl, heteroaryl selected from the group consisting of furanyl, thienyl, pyrrolyl, oxazolyl, thiazolyl, imidazolyl, pyridinyl, pyrimidinyl, pyrazinyl and indolyl, C1–5 alkoxy, aryloxy, arylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl or aryl, C1–5 alkanoylamino, aroylamino, C1–5 alkylthio, arylthio, ureido wherein either nitrogen atom may be independently substituted by C1–5 alkyl or aryl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl or aryl, halogen, hydroxy, oxo, carboxy and cyano; or R6 and R7 together with the carbon they are attached form a carbocyclic ring selected from the group consisting of cyclopropyl, cyclobutyl, cyclopentyl and cyclohexyl or heterocyclic ring selected from the group consisting of piperidinyl, morpholinyl and thiomorpholinyl, the carbocyclic or heterocyclic ring being optionally substituted with one or more $R_g$;

$R_g$ is selected from the group consisting of C1–3 alkyl, C3–6 cycloalkyl, C1–3 alkanoyl, C1–3 alkoxycarbonyl and carbamoyl wherein the nitrogen atom may be independantly mono or disubstituted by C1–5 alkyl; $R_g$ may be further optionally substituted by one or more $R_h$;

$R_h$ is phenyl or amino wherein the nitrogen atom may be independently mono or di-substituted by C1–3 alkyl;

R8 is hydrogen or methyl;

Ri is hydrogen or methyl and and X is O.

Still yet even more preferred are compounds of the formula (I) as described immediately above and wherein:

A is as defined above;
R1 is C1–3 alkyl, C3–6 cycloalkyl, phenyl, naphthyl, heterocyclyl selected from the group consisting of piperidinyl, morpholinyl, piperazinyl, pyranyl and thiopyranyl; heteroaryl selected from the group consisting of furanyl, thienyl, pyrrolyl, oxazolyl, thiazolyl, imidazolyl, pyridinyl and indolyl or amino, wherein R1 is optionally substituted by one or more $R_a$;
  $R_a$ is selected from the group consisting of C1–3 alkyl, C5–6 cycloalkyl, phenyl, heterocyclyl selected from the group consisting of piperidinyl, morpholinyl and piperazinyl, heteroaryl selected from the group consisting of furanyl, thienyl, pyrrolyl, imidazolyl, tetrazolyl, pyridinyl, indolyl, benzofuranyl, benzothienyl, benzimidazolyl, benzthiazolyl, quinolinyl and isoquinolinyl, C1–3 alkoxy, C1–3 alkoxycarbonyl, aryloxycarbonyl, C1–5 alkanoyloxy, aroyloxy, carbamoyl wherein the nitrogen atom may be independently mono or di-substituted by C1–3 alkyl, phenyl or heteroaryl selected from the group consisting of pyrrolyl, imidazolyl, pyridinyl, indolyl, benzofuranyl, benzothienyl, benzimidazolyl and benzthiazolyl, C1–5 alkanoylamino, aroylamino, C1–3 alkylthio, arylthio, ureido wherein either nitrogen atom may be independently substituted by C1–3alkyl or phenyl, C1–5 alkylsulfonylamino, arylsulfonylamino, amino wherein the nitrogen atom may be independently mono or di-substituted by C1–3alkyl, phenyl, heterocyclyl selected from the group consisting of piperidinyl, morpholinyl and piperazinyl or heteroaryl selected from the group consisting of pyrrolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_a$ may be firer optionally substituted by one or more $R_b$;
    $R_b$ is selected from the group consisting of C1–3 alkyl, C5–6 cycloalkyl, C1–3 alkoxy, halogen and hydroxy;
R2 is hydrogen;
R3 and R4 are as defined immediately above;
R5 is C1–5 alkyl, C5–6 cycloalkyl or phenyl wherein R5 is optionally substituted by one or more $R_c$;
  $R_c$ is selected from the group consisting of C1–3 alkyl, C3–6 cycloalkyl, phenyl, naphthyl, 4-piperidinyl, 4-morpholinyl, piperazinyl, furanyl, thienyl, thiazolyl, imidazolyl, pyridinyl, indolyl, C1–5 alkoxy, phenoxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl or phenyl, C1–5 alkanoylamino, C1–3 alkylthio, ureido wherein either nitrogen atom may be independently substituted by C1–3 alkyl or phenyl, C1–5 alkoxycarbonylamino, C1–5 alkylsulfonylamino, arylsulfonylamino, amino wherein the nitrogen atom may be independently mono or di-substituted by C1–3 alkyl or phenyl, halogen, hydroxy, oxo, carboxy and cyano, $R_c$ may be further optionally substituted by one or more $R_d$;
    $R_d$ is selected from the group consisting of C1–5 alkyl, $C_{5-6}$ cycloalkyl, phenyl, benzyl, C1–5 alkoxy, phenoxy, benzyloxy, aroyl, halogen, hydroxy, oxo, carboxy and cyano;
R6 is hydrogen or C1–3alkyl said alkyl being optionally interrupted by 1 to two heteroatoms selected from the group consisting of N,O and S;

R7 is hydrogen, C1–5 alkyl said alkyl being optionally interrupted by 1 to two heteroatoms selected from the group consisting of N,O and S, phenyl or cyano, wherein R7 is optionally substituted by one or more $R_e$;
  $R_e$ is selected from the group consisting of C1–3 alkyl, C3–6 cycloalkyl, phenyl, naphthyl, furanyl, thienyl, thiazolyl, imidazolyl, pyridinyl, indolyl, C1–3 alkoxy, benzyloxy, pyridylC1–3alkoxy, thienylC1–3alkoxy, furanylC1–3alkoxy, C1–3 alkoxycarbonyl, phenoxyoxycarbonyl, C1–5 alkanoyloxy, aroyloxy, carbamoyl wherein the nitrogen atom may be independently mono or di-substituted by C1–3 alkyl or phenyl, C1–5 alkanoylamino, aroylamino, methylthio, benzylthio, ureido wherein either nitrogen atom may be independently substituted by C1–5 alkyl or phenyl, C1–3 alkoxycarbonylamino, amino wherein the nitrogen atom may be independently mono or di-substituted by C1–5 alkyl or phenyl, halogen, hydroxy, oxo, carboxy and cyano, $R_e$ may be further optionally substituted by one or more $R_f$;
    $R_f$ is selected from the group consisting of C1–3 alkyl, phenyl optionally substituted by one or more groups selected from the group consisting of halogen and methyl, heterocyclyl selected from the group consisting of piperidinyl, morpholinyl and piperazinyl, heteroaryl selected from the group consisting of furanyl, thienyl, pyrrolyl and pyridinyl, C1–3 alkoxy, aryloxy, benzyloxy, C1–5 alkoxycarbonyl, C1–5 alkanoyloxy, aroyloxy, carbamoyl wherein the nitrogen atom may be independently mono or di-substituted by C1–5 alkyl or phenyl, C1–5 alkanoylamino, aroylamino, C1–5 alkylthio, ureido wherein either nitrogen atom may be independently substituted by C1–5 alkyl or phenyl, C1–5 alkoxycarbonylamino, C1–5 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl or phenyl, halogen, hydroxy, oxo, carboxy and cyano;
or R6 and R7 together with the carbon they are attached form cyclopropyl or a heterocyclic ring selected from the group consisting of piperidinyl, pyranyl and thiopyranyl, the cyclopropyl or heterocyclic ring being optionally substituted with one or more $R_g$;
  $R_g$ is selected from the group consisting of methyl, benzyl, acetyl, benzoyl, benzyloxycarbonyl and ethoxycarbonyl;
R8 is hydrogen and
X is O.
Even much more preferred are compounds of the formula (I) as described immediately above and wherein:
A is as described above;
R1 is C3–6 cycloalkyl, phenyl, naphthyl, piperidinyl, morpholinyl, piperazinyl, pyranyl, thiopyranyl, furanyl, thienyl, pyrrolyl or amino, wherein R1 is optionally substituted by one or more $R_a$;
  $R_a$ is selected from the group consisting of C1–3 alkyl, C5–6 cycloalkyl, phenyl, furanyl, thienyl, pyrrolyl, imidazolyl, indolyl, benzofuranyl, benzothienyl, benzimidazolyl, benzthiazolyl, C1–3 alkoxy, C1–3 alkoxycarbonyl, carbamoyl wherein the nitrogen atom may be independently mono or di-substituted by C1–3 alkyl or phenyl, C1–5 alkanoylamino, aroylamino, ureido wherein either nitrogen atom may be independently substituted by C1–3alkyl or phenyl, C1–5 alkylsulfonylamino, arylsulfonylamino, amino wherein the nitrogen atom may be independently mono or di-substituted by C1–3alkyl or phenyl, halogen, hydroxy, oxo, carboxy and cyano, $R_a$ may be further optionally substituted by one or more $R_b$;

$R_b$ is selected from the group consisting of C1–3alkyl, C1–3alkoxy, halogen and hydroxy;

R2,R3 and R4 are as defined immediately above;

R5 is C1–5 alkyl, C5–6 cycloalkyl or phenyl, wherein R5 is optionally substituted by one or more groups of the formula $R_c$;

$R_c$ is selected from the group consisting of C1–3 alkyl, C3–6 cycloalkyl, phenyl, naphthyl, 4-piperidinyl, furanyl, thienyl, thiazolyl, imidazolyl, pyridinyl, indolyl, C1–3 alkoxy, C1–5 alkoxycarbonyl, C1–5 alkanoyloxy, benzoyloxy, carbamoyl wherein the nitrogen atom may be independently mono or di-substituted by C1–3 alkyl or phenyl, C1–5 alkanoylamino, C1–3 alkyithio, C1–3 alkoxycarbonylamino, C1–3 alkylsulfonylamino, amino wherein the nitrogen atom may be independently mono or di-substituted by C1–3 alkyl or phenyl, halogen, hydroxy, oxo, carboxy and cyano, $R_c$ may be further optionally substituted by one or more $R_d$;

$R_d$ is selected from the group consisting of C1–3 alkyl, phenyl, benzyl, C1–3 alkoxy, phenoxy, benzyloxy, benzoyl, halogen, hydroxy, oxo, carboxy and cyano;

wherein the configuration at the stereocenter defined by R4 and R5 and the carbon they are attached to is defined as L;

R6 is hydrogen or C1–2 alkyl said alkyl being optionally interrupted by 1 to two heteroatoms selected from the group consisting of N,O and S;

R7 is C1–5 alkyl said alkyl being optionally interrupted by 1 to two heteroatoms selected from the group consisting of N,O and S; phenyl or cyano wherein R7 is optionally substituted by one or more groups of the formula $R_e$;

$R_e$ is selected from the group consisting of methyl, C3–6 cycloalkyl, phenyl, naphthyl, furanyl, thienyl, thiazolyl, imidazolyl, pyridinyl, indolyl, C1–3 alkoxy, benzyloxy, pyridylC1–3alkoxy, thienylC1–3alkoxy, furanylC1–3alkoxy, C1–5 alkanoylamino, aroylamino, methylthio, benzylthio, C1–3 alkoxycarbonylamino, amino wherein the nitrogen atom may be independently mono or di-substituted by C1–5 alkyl or phenyl, halogen, hydroxy, oxo, carboxy and cyano, $R_e$ may be further optionally substituted by one or more $R_f$;

$R_f$ is selected from the group consisting of C1–3 alkyl, phenyl optionally substituted by one or more groups selected from halogen and methyl, C1–3 alkoxy, aryloxy, benzyloxy, C1–3 alkoxycarbonyl, carbamoyl wherein the nitrogen atom may be independently mono or di-substituted by C1–3 alkyl or phenyl, C1–5 alkanoylamino, aroylamino, amino wherein the nitrogen atom may be independently mono or di-substituted by C1–3 alkyl or phenyl, halogen, hydroxy, oxo, carboxy and cyano;

or R6 and R7 together with the carbon they are attached form cyclopropyl or a heterocyclic ring selected from the group consisting of piperidinyl and pyranyl, the cyclopropyl or heterocyclic ring being optionally substituted with one or more $R_g$.

$R_g$ is methyl;

$R_h$ is as described immediately above; and

X is O.

Yet even much more preferred are compounds of the formula (I) as described immediately above and wherein:

A is as described above;

R1 is cyclopropyl, cyclohexyl, phenyl, naphthyl, piperidinyl, morpholinyl, piperazinyl, pyranyl, thiopyranyl or amino wherein R1 is optionally substituted by one or more $R_a$;

$R_a$ is selected from the group consisting of C1–3 alkyl, C5–6 cycloalkyl, phenyl, furanyl, thienyl, pyrrolyl, imidazolyl, indolyl, benzofuranyl, benzothienyl, benzimidazolyl, benzthiazolyl, C1–3 alkoxy, C1–3 alkoxycarbonyl, carbamoyl wherein the nitrogen atom may be independently mono or di-substituted by C1–3 alkyl or phenyl, C1–5 alkanoylamino, aroylamino, C1–5 alkylsulfonylamino, arylsulfonylamino, amino wherein the nitrogen atom may be independently mono or di-substituted by C1–3 alkyl, halogen, hydroxy, oxo, carboxy and cyano, $R_a$ may be further optionally substituted by one or more $R_b$;

$R_b$ is selected from the group consisting of C1–3 alkoxy, halogen and hydroxy, R2,R3 and R4 are as described immediately above;

R5 is C1–5 alkyl or C5–6 cycloalkyl wherein R5 is optionally substituted by one or more $R_c$;

$R_c$ is selected from the group consisting of methyl, C3–6 cycloalkyl, phenyl, naphthyl, thienyl, imidazolyl, pyridinyl, indolyl, C1–4 alkoxy, C1–5 alkanoylamino, methylthio, halogen, hydroxy, oxo, carboxy and cyano, $R_c$ may be further optionally substituted by one or more $R_d$;

$R_d$ is selected from the group consisting of methyl, phenyl, benzyl, methoxy, phenoxy, benzyloxy, benzoyl, halogen and hydroxy;

R6 is as described immediately above;

R7 is C1–5 alkyl or phenyl, wherein R7 is optionally substituted by one or more $R_e$;

$R_e$ is selected from the group consisting of C3–6 cycloalkyl, phenyl, naphthyl, thienyl, imidazolyl, pyridinyl, indolyl, methoxy, benzyloxy, C1–3 alkanoylamino, methylthio wherein the sulfur atom may be oxidized to a sulfoxide or sulfone, benzylthio wherein the sulfur atom may be oxidized to a sulfoxide or sulfone, methoxycarbonylamino, amino wherein the nitrogen atom may be independently mono or di-substituted by C1–3 alkyl, halogen, hydroxy, carboxy and cyano, $R_e$ may be further optionally substituted by one or more $R_f$;

$R_f$ is selected from the group consisting of methyl, phenyl optionally substituted by one or more groups selected from halogen or methyl, methoxy, phenoxy, benzyloxy, methoxycarbonyl, amino wherein the nitrogen atom may be independently mono or di-substituted by C1–3 alkyl or phenyl, halogen, hydroxy and carboxy;

or R6 and R7 together with the carbon they are attached form a cyclopropyl ring; and $R_g$, $R_h$ and X are as described immediately above.

Penultimately preferred are compounds of the formula (I) as described immediately above and wherein:

A is as described above;

R1 is cyclopropyl, cyclohexyl, phenyl, naphthyl, piperidinyl, morpholinyl, piperazinyl, pyranyl or thiopyranyl, wherein R1 is optionally substituted by one or more $R_a$;

$R_a$ is selected from the group consisting of pyrrolyl, imidazolyl, indolyl, benzimidazolyl, methoxy, methoxycarbonyl, amino wherein the nitrogen atom may be independently mono or di-substituted by C1–3 alkyl, halogen, hydroxy and carboxy, $R_a$ may be further optionally substituted by one or more $R_b$;

$R_b$ is selected from the group consisting of methoxy, halogen and hydroxy;

R2,R3,R4 and R5 are as described immediately above;

$R_c$ is selected from the group consisting of methyl, C3–6 cycloalkyl, phenyl, naphthyl, C1–4 alkoxy, C1–3 alkanoylamino, methylthio, halogen, hydroxy, oxo, carboxy and cyano, $R_c$ may be further optionally substituted by one or more $R_d$;

$R_d$ is selected from the group consisting of methyl, phenyl, methoxy, halogen and hydroxy;

R6 is hydrogen;

R7 is as described immediately above;

$R_e$ is selected from the group consisting of C5–6 cycloalkyl, phenyl, naphthyl, thienyl, indolyl, methoxy, benzyloxy, methylthio, benzylthio, methoxycarbonylamino, halogen, hydroxy, carboxy and cyano, $R_e$ may be further optionally substituted by one or more $R_f$;

$R_f$ is selected from the group consisting of methyl, phenyl optionally substituted by halogen, methoxy, phenoxy, benzyloxy, methoxycarbonyl, halogen, hydroxy and carboxy; and $R_g$, $R_h$ and X are as described immediately above.

Ultimately preferred are compounds of the formula (I) wherein:

A is as described above;

R1 is 4-morpholinyl, 4pyranyl or phenyl;

R2,R4, $R_a$ and $R_b$ are as described immediately above;

R5 is C1–5 alkyl wherein R5 is optionally substituted by one or more $R_c$;

$R_c$ is selected from the group consisting of C3–6 cycloalkyl, phenyl and 2-naphthyl, $R_c$ may be further optionally substituted by one or more $R_d$;

$R_d$ is selected from the group consisting of methyl and halogen,

R6 and R7 are as described immediately above;

$R_e$ is selected from the group consisting of C5–6 cycloalkyl, phenyl, naphthyl, indolyl, benzyloxy, methylthio, benzylthiohalogen and carboxy, $R_e$ may be further optionally substituted by one or more $R_f$; and $R_f$ is selected from the group consisting of methyl, methoxy, methoxycarbonyl, halogen and hydroxy; and $R_g$, $R_h$ and X are as described immediately above.

In a second generic aspect of the invention, there are provided compounds of formula (Ia):

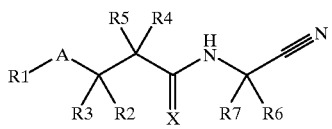

(Ia)

wherein:

A is —C(O)— or —CH(OR8)-;

R1 is alkyl, alkoxy, cycloalkyl, aryl, aryloxy, benzyloxy, heterocyclyl, heteroaryl or amino wherein R1 is optionally substituted by one or more Ra;

Ra is selected from the group consisting of a bond, alkyl, cycloalkyl, aryl, heterocyclyl, heteroaryl, alkoxy, aryloxy, alkanoyl, aroyl, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino; Ra may be further optionally substituted by one or more Rb;

$R_b$ is selected from the group consisting of alkyl, cycloalkyl, aryl, heterocyclyl, heteroaryl, arylalkyl, alkoxy, aryloxy, arylalkoxy, alkanoyl, aroyl, amino wherein the nitrogen atom may be independently mono or di-substituted by alkyl, aryl, acyl, heterocyclyl or heteroaryl, halogen, hydroxy, oxo, carboxy, cyano, nitro, amidino and guanidino;

R2 is hydrogen, $OR_j$ or lower alkyl;

R3 is hydrogen or lower alkyl;

R4 is hydrogen or lower alkyl;

R5 is hydrogen, alkyl, cycloalkyl, aryl, heterocyclyl or heteroaryl, wherein R5 is optionally substituted by one or more $R_c$;

$R_c$ is selected from the group consisting of a bond, alkyl, cycloalkyl, bicycloalkyl, aryl, indenyl, indanyl, dihydronaphthyl, tetrahydronaphthyl, heterocyclyl, heteroaryl, alkoxy, aryloxy, arylalkoxy, alkoxycarbonyl, aryloxycarbonyl, alkanoyl, aroyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, $R_c$ may be further optionally substituted by one or more $R_d$;

$R_d$ is selected from the group consisting of alkyl, cycloalkyl, aryl, arylalkyl, alkoxy, aryloxy, arylalkoxy, alkanoyl, aroyl, amino, halogen, hydroxy, oxo, carboxy, cyano, nitro, amidino and guanidino;

or R4 and R5 together with the carbon they are attached form a 3 to 7 membered carbocyclic ring optionally substituted with one or more $R_d$;

R6 is hydrogen or lower alkyl wherein one or more carbon atoms are optionally replaced by 1 to two heteroatoms selected from the group consisting of N,O and S;

R7 is hydrogen, alkyl wherein one or more carbon atoms are optionally replaced by 1 to two heteroatoms selected from the group consisting of N,O and S, cycloalkyl, aryl, heterocyclyl, heteroaryl or cyano, wherein R7 is optionally substituted by one or more $R_e$;

$R_e$ is selected from the group consisting of a bond alkyl, cycloalkyl, aryl, heterocyclyl, heteroaryl, alkoxy, aryloxy, arylalkoxy, alkanoyl, aroyl, alkoxycarbonyl, aryloxycarbonyl, alkanoyloxy, aroyloxy, heteroarylalkoxy, carbamoyl wherein the nitrogen atom may be independently mono or di-substituted by alkyl, aryl, heterocyclyl or heteroaryl, alkanoylamino, aroylamino, alkylcarbamoyl, arylcarbamoyl, alkylthio wherein the sulfur atom may be oxidized to a sulfoxide or sulfone, arylthio wherein the sulfur atom may be oxidized to a sulfoxide or sulfone, arylalkylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, $R_e$ may be further optionally substituted by one or more $R_f$;

$R_f$ is selected from the group consisting of alkyl, cycloalkyl, aryl optionally substituted by one or more groups selected from halogen, methyl or methoxy, heterocyclyl, heteroaryl, alkoxy, aryloxy, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylcarbamoyl, arylcarbamoyl, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino;

or R6 and R7 together with the carbon they are attached form a 3 to 7 membered carbocyclic or heterocyclic ring, the carbocyclic or heterocyclic ring being optionally substituted with one or more $R_g$;

$R_g$ is selected from the group consisting of a bond, alkyl, cycloalkyl, bicycloalkyl, benzyl, aryl, dihydronaphthyl, tetrahydronaphthyl, indenyl, indanyl, heterocyclyl selected from the group consisting of pyrrolidinyl, piperidinyl, morpholinyl, thiomorpholinyl, tetrahydropyranyl, tetrahydrothiopyranyl, indolinyl and piperazinyl, heteroaryl selected from the group consisting of furanyl, thienyl, pyrimidinyl, pyrrolyl, imidazolyl and pyridinyl, C1–5 alkanoyl, aroyl, C1–5 alkoxycarbonyl, aryloxycarbonyl, carbamoyl wherein the nitrogen atom may be independantly mono or disubstituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, thiazolyl, imidazolyl, pyridinyl, benzimidazolyl and quinolinyl, C1–5 alkanoylamino, aroylamino, C1–5 alkylthio, arylthio, C1–5 alkylsulfonylamino, arylsulfonylamino, C1–5 alkylaminosulfonyl, arylaminosulfonyl, amino wherein the nitrogen atom may be independently mono or disubstituted by alkyl, cycloalkyl, bicycloalkyl, aryl, aroyl, benzoyl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_g$ may be further optionally substituted by one or more $R_h$;

$R_h$ is selected from the group consisting of a bond, C1–5 alkyl, C3–7 cycloalkyl, aryl optionally substituted by one or more groups selected from halogen, lower alkyl or lower alkoxy, benzyl, benzyloxy, dihydronaphthyl, tertrabydronaphthyl, indenyl, indanyl, heterocyclyl selected from the group consisting of pyrrolidinyl, piperidinyl, morpholinyl, thiomorpholinyl, piperazinyl, indolinyl, tetrahydropyranyl and tetrahydrothiopyranyl, heteroaryl selected from the group consisting of furanyl, thienyl pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl and quinoxalinyl, C1–5 alkoxy, aryloxy, amino wherein the nitrogen atom may be independently mono or di-substituted by alkyl, aryl, heterocyclyl selected from the group consisting of pyrrolidinyl, piperidinyl and morpholinyl or heteroaryl selected from the group consisting of furanyl, thienyl, pyrrolyl and pyridinyl, halogen, hydroxy, oxo, carboxy, cyano, nitro, amidino and guanidino; $R_h$ may be further optionally substituted by one or more $R_i$;

$R_i$ is alkyl, hydroxy, oxo and halogen;

$R_j$ is hydrogen, alkyl, cycloalkyl;

R8 is hydrogen, alkyl, cycloalkyl, cycloalkyl-alkyl or arylalkyl;

X is O or S; and pharmaceutically acceptable salts, esters or tautomers thereof.

Preferred are compounds of the formula (Ia) wherein:

R1 is C1–8 alkyl, C3–7 cycloalkyl, aryl, heterocyclyl selected from the group consisting of pyrrolidinyl, piperidinyl, morpholinyl, thiomorpholinyl, 2-oxa-5-aza-bicyclo[2,2,1]heptanyl, piperazinyl, indolinyl, tetrahydropyranyl and tetrahydrothiopyranyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl and amino wherein R1 is optionally substituted by one or more $R_a$;

$R_a$ is selected from the group consisting of a bond, C1–8 alkyl, C3–7 cycloalkyl, aryl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, pyrazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino, guanidino; $R_a$ may be further optionally substituted by one or more $R_b$;

$R_b$ is selected from the group consisting of C1–8 alkyl, C3–6 cycloalkyl, aryl, heteroaryl, C1–8 alkoxy, aryloxy, alkanoyl, aroyl, amino wherein the nitrogen atom may be independently mono or di-substituted by alkyl, cycloalkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, pyridinyl, pyridazinyl, pyrimidinyl, pyrazinyl, indolyl, isoindolyl, benzofuranyl, benzothienyl, benzimidazolyl, benzthiazolyl, quinolinyl and isoquinolinyl, halogen, hydroxy, oxo, carboxy, cyano, nitro, amidino and guanidino;

R2 is hydrogen, $OR_j$ or C1–3 alkyl;

R3 is hydrogen or C1–5 alkyl;

R4 is hydrogen or C1–5 alkyl;

R5 is hydrogen, C1–8 alkyl, C3–7 cycloalkyl, aryl wherein R5 is optionally substituted by one or more $R_c$;

$R_c$ is selected from the group consisting of a bond, C1–8 alkyl, C3–7 cycloalkyl, bicycloalkyl, aryl, dihydronaphthyl, tetrahydronaphthyl, indenyl, indanyl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, alkanoyl, aroyl, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, C1–5aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_c$ may be further optionally substituted by one or more $R_d$;

$R_d$ is selected from the group consisting of C1–8 alkyl, C3–6 cycloalkyl, aryl, arylalkyl, C1–8 alkoxy, aryloxy, arylalkoxy, aroyl, amino, halogen, hydroxy, oxo, carboxy, cyano, nitro, amidino and guanidino;

R7 is hydrogen, C1–8 alkyl wherein one or more carbon atoms are optionally replaced by 1 to two heteroatoms selected from the group consisting of N,O and S, C3–7 cycloalkyl, aryl, heteroaryl or cyano, wherein R7 is optionally substituted by one or more $R_e$;

$R_e$ is selected from the group consisting of a bond, C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, heteroarylC1–8alkoxy wherein the heteroaryl is as hereinabove described in this paragraph, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, arylC1–8 alkylthio, ureido wherein either nitrogen atom may be independently substituted by aLkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_e$ may be further optionally substituted by one or more $R_f$;

$R_f$ is selected from the group consisting C1–8 alkyl, C3–7 cycloalkyl, aryl optionally substituted by one or more groups selected from the group consisting halogen, methyl and methoxy, heterocyclyl selected from the group consisting pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino, and guanidino;

or R6 and R7 together with the carbon they are attached form a 3 to 7 membered carbocyclic or heterocyclic ring, the carbocyclic or heterocyclic ring being optionally substituted with one or more $R_g$;

$R_g$ is selected from the group consisting of a bond, alkyl, cycloalkyl, bicycloalkyl, phenyl, naphthyl, benzyl, dihydronaphthyl, tetrahydronaphthyl, indenyl, indanyl, heterocyclyl selected from the group consisting of pyrrolidinyl, piperidinyl, morpholinyl, thiomorpholinyl, tetrahydropyranyl, tetrahydrothiopyranyl, indolinyl and piperazinyl, heteroaryl selected from the group consisting of furanyl, thienyl, pyrimidinyl and pyridinyl, C1–5alkanoyl, aroyl, C1–5alkoxycarbonyl, aryloxycarbonyl, carbamoyl wherein the nitrogen atom may be independantly mono or disubstituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, thiazolyl, imidazolyl, pyridinyl, benzimidazolyl and quinolinyl, amino wherein the nitrogen atom may be independently mono or di-substituted by C1–5 alkyl, C3–6 cycloalkyl, C7–8 bicycloalkyl, phenyl, benzyl, benzoyl or naphthoyl, C1–5 alkylthio wherein the sulfur atom may be oxidised to a sulfoxide or sulfone, arylthio wherein the sulfur atom may be oxidised to a sulfoxide or sulfone, C1–5 alkylaminosulfonyl, arylaminosulfonyl, halogen, hydroxy, oxo, carboxy and cyano, $R_g$ may be further optionally substituted by one or more $R_h$;

$R_h$ is selected from the group consisting of C1–5 alkyl, C3–7 cycloalkyl, aryl optionally substituted by one or more groups selected from halogen, C1–5 alkyl or C1–5 alkoxy, dihydronaphthyl, tertrahydronaphthyl, indenyl, indanyl, benzyl, benzyloxy, heterocyclyl selected from the group consisting of pyrrolidinyl, piperidinyl, morpholinyl, thiomorpholinyl, piperazinyl, indolinyl, tetrahydropyranyl and tetrahydrothiopyranyl, heteroaryl selected from the group consisting of furanyl, thienyl, pyrrolyl, imidazolyl, pyridinyl, pyrimidinyl, pyrazinyl, indolyl, benzimidazolyl, quinolinyl, isoquinolinyl, quinazolinyl, benzoxazolyl and quinoxalinyl, C1–5 alkoxy, aryloxy, amino wherein the nitrogen atom may be independently mono or di-substituted by alkyl, aryl, heterocyclyl selected from the group consisting of piperidinyl and morpholinyl, or heteroaryl selected from the group consisting of furanyl, thienyl and pyridinyl, halogen, hydroxy, oxo, carboxy and cyano; and R8 is hydrogen, alkyl, cycloalkyl-alkyl or arylalkyl;

$R_i$ is C1–8 alkyl, hydroxy, oxo and halogen $R_j$ is hydrogen or alkyl and

X is O.

More preferred are compounds of the formula (I) as described immediately above and wherein:

A is —C(O)—;

R1 is C1–5 alkyl, C3–6 cycloalkyl, phenyl, naphthyl, heterocyclyl selected from the group consisting of pyrrolidinyl, piperidinyl, morpholinyl, thiomorpholinyl, 2-oxa-5-aza-bicyclo[2,2,1]heptanyl, piperazinyl, tetrahydropyranyl and tetrahydrothiopyranyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl or amino, wherein R1 is optionally substituted by one or more $R_a$;

$R_a$ is selected from the group consisting of a bond, C1–3 alkyl, C3–6 cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, quinolinyl and isoquinolinyl, C1–3 alkoxy, phenoxy, C1–3 alkoxycarbonyl, aryloxycarbonyl, C1–5 alkanoyloxy, aroyloxy, carbamoyl wherein the nitrogen atom may be independently mono or di-substituted by C1–5 alkyl, phenyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio, arylthio, ureido wherein either nitrogen atom may be independently substituted by C1–5alkyl, phenyl or naphthyl; C1–5 alkoxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_a$ may be further optionally substituted by one or more $R_b$;

$R_b$ is selected from the group consisting of C1–3 alkyl, C5–6 cycloalkyl, aryl, heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–3 alkoxy, phenoxy, C1–8 alkanoyl, amino wherein the nitrogen atom may be independently mono or di-substituted by C1–5alkyl, C3–6 cycloalkyl, phenyl or naphthyl, halogen, hydroxy, oxo, carboxy and cyano;

R2 is hydrogen;
R3 is hydrogen;
R4 is hydrogen;
R5 is C1–5 alkyl, C3–6 cycloalkyl or phenyl, wherein R5 is optionally substituted by one or more $R_c$;

$R_c$ is selected from the group consisting of a bond, C1–3 alkyl, C3–6 cycloalkyl, phenyl, naphthyl, indenyl, indanyl, heterocyclyl selected from the group consisting of piperidinyl, morpholinyl and piperazinyl, heteroaryl selected from the group consisting of furanyl, thienyl, thiazolyl, imidazolyl, pyridinyl, indolyl, quinolinyl and isoquinolinyl, C1–5 alkoxy, phenoxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl or heteroaryl selected the group consisting of furanyl, thienyl, pyrrolyl, oxazolyl, thiazolyl, imidazolyl, pyridinyl and indolyl, C1–5 alkoxycarbonylamino, C1–5 alkylcarbamoyloxy, arylcarbamoyloxy, C1–5 alkylsulfonylamino, arylsulfonylamino, amino wherein the nitrogen atom may be independently mono or di-substituted by C1–3 alkyl, phenyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, $R_c$ may be further optionally substituted by one or more $R_d$;

$R_d$ is selected from the group consisting of C1–5 alkyl, C5–6 cycloalkyl, phenyl, naphthyl, arylC1–3alkyl, C1–5 alkoxy, phenoxy, arylC1–3alkoxy, aroyl, amino, halogen, hydroxy, oxo, carboxy and cyano;

R6 is hydrogen or C1–3alkyl wherein one or more carbon atoms are optionally replaced by 1 to two heteroatoms selected from the group consisting of N,O and S;

R7 is hydrogen, C1–5 alkyl wherein one or more carbon atoms are optionally replaced by 1 to two heteroatoms selected from the group consisting of N,O and S, C3–6 cycloalkyl, phenyl, naphthyl, heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl or cyano, wherein R7 is optionally substituted by one or more $R_e$;

$R_e$ is selected from the group consisting of C1–3 alkyl, C3–6 cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxy, aryloxy, arylC1–3alkoxy, heteroarylC1–3alkoxy wherein the heteroaryl is as hereinabove described in this paragraph, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl or heteroaryl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, arylthio wherein the sulfur atom may be oxidized to a sulfoxide or sulfone, arylC1–3alkylthio wherein the sulfur atom may be oxidized to a sulfoxide or sulfone, ureido wherein either nitrogen atom may be independently substituted by C1–5 alkyl or phenyl, C1–5 alkoxycarbonylamino, C1–5 alkylsulfonylamino, arylsulfonylamino, amino wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl and pyridinyl, indolyl, halogen, hydroxy, oxo, carboxy and cyano, $R_e$ may be further optionally substituted by one or more $R_f$;

$R_f$ is selected from the group consisting of C1–5 alkyl, C3–6 cycloalkyl, phenyl optionally substituted by one or more groups selected from halogen or methyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, pyrimidinyl, pyrazinyl and indolyl, C1–5 alkoxy, aryloxy, arylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl or aryl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl or aryl, C1–5 alkoxycarbonylamino, aryloxycarbonylamino, C1–5 alkylcarbamoyloxy, arylcarbamoyloxy, C1–5 alkylsulfonyloxy, arylsulfonylamino, C1–5 alkylaminosulfonyl, arylaminosulfonyl, amino wherein the nitrogen atom may be independently mono or di-substituted by C1–5 alkyl or aryl, halogen, hydroxy, oxo, carboxy and cyano; or R6 and R7 together with the carbon they are attached form a carbocyclic ring selected from the group consisting of cyclopropyl, cyclobutyl, cyclopentyl, cyclohexyl, cycloheptyl or heterocyclic ring selected from the group consisting of azetidinyl, pyrrolidinyl, piperidinyl, tetrahydropyranyl and tetrahydrothiopyranyl, the carbocyclic or heterocyclic ring being optionally substituted with one or more $R_g$;

$R_g$ is selected from the group consisting of a bond, C1–8 alkyl, C3–8 cycloalkyl, C7–8 bicycloalkyl, benzyl, dihydronaphthyl, tetrahydronaphthyl, indenyl, indanyl, heterocyclyl selected from the group consisting of pyrrolidinyl, piperidinyl, tetrahydropyranyl, tetrahydrothiopyranyl, piperazinyl and morpholinyl, heteroaryl selected from the group consisting of thienyl, pyrimidinyl and pyridinyl, C1–5 alkanoyl, C1–3 alkoxycarbonyl, carbamoyl wherein the nitrogen atom may be independantly mono or disubstituted by C1–5 alkyl and amino wherein the nitrogen atom may be independently mono or di-substituted by C1–5 alkyl, C3–6 cycloalkyl, C7–8 bicycloalkyl, phenyl, benzyl, benzoyl or naphthoyl, $R_g$ may be further optionally substituted by one or more $R_h$; and $R_h$ is selected from the group consisting of C1–8 alkyl, C3–8 cycloalkyl, phenyl, benzyl, benzyloxy, heterocyclyl selected from the group consisting of piperidinyl, indolinyl, tetrahydropyranyl and tetrahydrothiopyranyl, heteroaryl selected from the group consisting of thienyl, pyrrolyl, pyridinyl, pyrimidinyl, indolyl, benzimidazolyl, quinolinyl and isoquinolinyl, amino wherein the nitrogen atom may be independently mono or di-substituted by C1–3 alkyl, halogen, hydroxy, oxo, cyano and trifluoromethyl.

Even more preferred are compounds of the formula (Ia) as desribed immediately above and wherein:

R1 is C3–6 cycloalkyl, phenyl, naphthyl, pyrrolidinyl, piperidinyl, morpholinyl, thiomorpholinyl, piperazinyl, tetrahydropyranyl, furanyl, thienyl, pyrrolyl or amino, wherein R1 is optionally substituted by one or more $R_a$;

$R_a$ is selected from the group consisting of a bond, C1–3 alkyl, C5–6 cycloalkyl, phenyl, furanyl, thienyl, pyrrolyl, imidazolyl, indolyl, benzofuranyl, benzothienyl, benzimidazolyl, benzthiazolyl, C1–3 alkoxy, C1–3 alkoxycarbonyl, carbamoyl wherein the nitrogen atom may be independently mono or di-substituted by C1–3 alkyl or phenyl; C1–5alkoxycarbonylamino, C1–5 alkanoylamino, aroylamino, ureido wherein either nitrogen atom may be independently substituted by C1–3alkyl or phenyl; C1–5 alkylsulfonylamino, arylsulfonylamino, amino wherein the nitrogen atom may be independently mono or di-substituted by C1–3alkyl or phenyl, halogen, hydroxy, oxo, carboxy and cyano, $R_a$ may be further optionally substituted by one or more $R_b$;

$R_b$ is selected from the group consisting of C1–3alkyl, C1–3alkoxy, amino wherein the nitrogen atom may be independently mono or di-substituted by C1–3alkyl or phenyl halogen, oxo and hydroxy;

R5 is C1–5 alkyl, C3–6 cycloalkyl or phenyl, wherein R5 is optionally substituted by one or more groups of the formula $R_c$.

$R_c$ is selected from the group consisting of a bond, C1–3 alkyl, C3–6 cycloalkyl, C7–8 bicycloalkyl, phenyl, naphthyl, dihydronaphthyl, tetrahydronaphthyl, indenyl, indanyl, 4-piperidinyl, furanyl, thienyl, thiazolyl, imidazolyl, pyridinyl, indolyl, C1–3 alkoxy, C1–5 alkoxycarbonyl, C1–5 alkanoyloxy, benzoyloxy, carbamoyl wherein the nitrogen atom may be independently mono or di-substituted by C1–3 alkyl or phenyl, C1–5 alkanoylamino, C1–3 alkylthio wherein the sulfur atom may be oxidized to a sulfoxide or sulfone, C1–3 alkoxycarbonylamino, C1–3 alkylsulfonylamino, amino wherein the nitrogen atom may be independently mono or di-substituted by C1–3 alkyl or phenyl, halogen, hydroxy, oxo, carboxy and cyano, $R_c$ may be further optionally substituted by one or more $R_d$;

$R_d$ is selected from the group consisting of C1–3 alkyl, phenyl, benzyl, C1–3 alkoxy, phenoxy, benzyloxy, benzoyl, halogen, hydroxy, oxo, carboxy and cyano;

wherein the configuration at the stereo center defined by R4 and R5 and the carbon they are attached to is defined as L;

R6 is hydrogen or C1–2alkyl one or more carbon atoms are optionally replaced by 1 to two heteroatoms selected from the group consisting of N,O and S;

R7 is C1–5 alkyl said alkyl being optionally interrupted by 1 to two heteroatoms selected from the group consisting of N,O and S; phenyl, pyridinyl or cyano wherein R7 is optionally substituted by one or more groups of the formula $R_e$;

$R_e$ is selected from the group consisting of a bond, methyl, C3–6 cycloalkyl, phenyl, naphthyl, furanyl, thienyl, thiazolyl, imidazolyl, pyridinyl, pyrrolidinyl, piperidinyl, indolyl, C1–3 alkoxy, benzyloxy, pyridinylC1–3alkoxy, thienylC1–3alkoxy, furanylC1–3alkoxy, C1–5 alkanoylamino, aroylamino, methylthio wherein the sulfur atom may be oxidized to a sulfoxide or sulfone, benzylthio wherein the sulfur atom may be oxidized to a sulfoxide or sulfone, C1–3 alkoxycarbonylamino, amino wherein the nitrogen atom may be independently mono or di-substituted by C1–5 alkyl or phenyl, halogen, hydroxy, oxo, carboxy and cyano, $R_e$ may be further optionally substituted by one or more $R_f$;

$R_f$ is selected from the group consisting of C1–5 alkyl, C3–6 cycloalkyl, phenyl optionally substituted by one or more groups selected from halogen or methyl, C1–3 alkoxy, aryloxy, benzyloxy, C1–3 alkoxycarbonyl, carbamoyl wherein the nitrogen atom may be independently mono or di-substituted by C1–3 alkyl or phenyl, C1–5 alkanoylamino, aroylamino, amino wherein the nitrogen atom may be independently mono or di-substituted by C1–3 alkyl or phenyl, halogen, hydroxy, oxo, carboxy and cyano;

R6 and R7 together with the carbon they are attached form a carbocyclic ring selected from the group consisting of cyclopropyl, cyclopentyl, cyclohexyl and cycloheptyl or heterocyclic ring selected from the group consisting of pyrrolidinyl, piperidinyl and tetrahydropyranyl, the carbocyclic or heterocyclic ring being optionally substituted with one or more $R_g$;

$R_g$ is selected from the group consisting of a bond C1–8 alkyl, C3–8 cycloalkyl, C7–8 bicycloalkyl, benzyl, dihydronaphthyl, tetrahydronaphthyl, indanyl, heterocyclyl selected from the group consisting of piperidinyl, tetrahydropyranyl, and tetrahydrothiopyranyl, C1–5 alkanoyl, C1–3 alkoxycarbonyl, carbamoyl wherein the nitrogen atom may be independantly mono or disubstituted by C1–5 alkyl and amino wherein the nitrogen atom may be independently mono or di-substituted by C1–5 alkyl, C3–6 cycloalkyl, C7–8 bicycloalkyl, phenyl, benzyl, benzoyl or naphthoyl, $R_g$ may be further optionally substituted by one or more $R_h$; and $R_h$ is selected from the group consisting of C1–8 alkyl, C3–8 cycloalkyl, phenyl, benzyl, benzyloxy, heterocyclyl selected from the group consisting of piperidinyl, indolinyl, tetrahydropyranyl and tetrahydrothiopyranyl, heteroaryl selected from the group consisting of thienyl, pyridinyl, indolyl, pyrrolyl and benzimidazolyl, amino wherein the nitrogen atom may be independently mono or di-substituted by methyl, halogen, hydroxy, oxo, cyano and trifluoromethyl.

Yet even more preferred are compounds of the formula (Ia) as described immediately above and wherein:

R1 is cyclohexyl, phenyl, naphthyl, pyrrolidinyl, piperidinyl, morpholinyl, thiomorpholinyl, or amino wherein R1 is optionally substituted by one or more $R_a$;

$R_a$ is selected from the group consisting of a bond, C1–3 alkyl, C5–6 cycloalkyl, phenyl, furanyl, thienyl, pyrrolyl, imidazolyl, indolyl, benzofuranyl, benzothienyl, benzimidazolyl, benzthiazolyl, C1–3 alkoxy, C1–3 alkoxycarbonyl, carbamoyl wherein the nitrogen atom may be independently mono or di-substituted by C1–3 alkyl or phenyl, C1–5alkoxycarbonylamino, C1–5 alkanoylamino, aroylamino, C1–5 alkylsulfonylamino, arylsulfonylamino, amino wherein the nitrogen atom may be independently mono or di-substituted by C1–3 alkyl, halogen, hydroxy, oxo, carboxy and cyano, $R_a$ may be further optionally substituted by one or more $R_b$;

$R_b$ is selected from the group consisting of C1–3 alkoxy, halogen and hydroxy, R5 is C1–5 alkyl wherein R5 is optionally substituted by one or more $R_c$;

$R_c$ is selected from the group consisting of a bond, C3–6 cycloalkyl, C7–8 bicycloalkyl, phenyl, naphthyl, dihydronaphthyl, tetrahydronaphthyl, indanyl, thienyl, imidazolyl, pyridinyl, indolyl, C1–3 alkoxy, C1–5 alkanoylamino, methylthio, halogen, hydroxy, oxo, carboxy and cyano, $R_c$ may be further optionally substituted by one or more $R_d$;

$R_d$ is selected from the group consisting of C1–3 alkyl, phenyl, benzyl, methoxy, phenoxy, benzyloxy, benzoyl, halogen and hydroxy;

R7 is C1–5 alkyl or phenyl, wherein R7 is optionally substituted by one or more $R_e$;

$R_e$ is selected from the group consisting of a bond, C3–6 cycloalkyl, phenyl, naphthyl, thienyl, imidazolyl, pyrrolidinyl, piperidinyl, pyridinyl, indolyl, C1–5 alkoxy, benzyloxy, C1–3 alkanoylamino, metnylthio wherein the sulfur atom may be oxidized to a sulfoxide or sulfone, benzylthio wherein the sulfur atom may be oxidized to a sulfoxide or sulfone, methoxycarbonylamino, amino wherein the nitrogen atom may be independently mono or di-substituted by C1–5 alkyl, halogen, hydroxy, carboxy and cyano, $R_e$ may be further optionally substituted by one or more $R_f$;

$R_f$ is selected from the group consisting of C1–5 alkyl, C3–6 cycloalkyl, phenyl optionally substituted by one or more groups selected from halogen or methyl, methoxy, phenoxy, benzyloxy, methoxycarbonyl, amino wherein the nitrogen atom may be independently mono or di-substituted by C1–3 alkyl or phenyl, halogen, hydroxy and carboxy;

R6 and R7 together with the carbon they are attached form a carbocyclic ring selected from the group consisting of cyclopropyl and cyclohexyl or heterocyclic ring selected from the group consisting of pyrrolidinyl and piperidinyl, the carbocyclic or heterocyclic ring being optionally substituted with one or more $R_g$;

$R_g$ is selected from the group consisting of a bond, C1–8 alkyl, C3–8 cycloalkyl, C7–8 bicycloalkyl, benzyl, tetrahydronaphthyl, indanyl, heterocyclyl selected from the group consisting of tetrahydropyranyl and tetrahydrothiopyranyl, acetyl, methoxycarbonyl, carbamoyl wherein the nitrogen atom may be independantly mono or disubstituted by C1–3 alkyl and amino wherein the nitrogen atom may be independently mono or di-substituted by C1–5 alkyl, C3–6 cycloalkyl, benzyl or benzoyl, $R_g$ may be further optionally substituted by one or more $R_h$; and $R_h$ is selected from the group consisting of C1–8 alkyl, C3–7 cycloalkyl, phenyl, benzyl, benzyloxy, heterocyclyl selected from the group consisting of piperidinyl, tetrahydropyranyl and tetrahydrothiopyranyl, heteroaryl selected from the group consisting of thienyl, pyridinyl, indolyl and benzimidazolyl, amino, methylamino, dimethylamino, halogen, hydroxy, oxo, cyano and trifluoromethyl.

Still yet even more preferred are compounds of the formula (I) as described immediately above and wherein:

R1 is phenyl, naphthyl, pyrrolidinyl, thiomorpholinyl or morpholinyl, wherein R1 is optionally substituted by one or more $R_a$;

$R_a$ is selected from the group consisting of a bond, C1–3 alkyl, pyrrolyl, imidazolyl, indolyl, benzimidazolyl, methoxy, methoxycarbonyl, t-butoxycarbonylamino, C1–3 alkylsulfonylamino, amino wherein the nitrogen atom may be independently mono or di-substituted by C1–3 alkyl, halogen, hydroxy, cyano and carboxy, $R_a$ may be further optionally substituted by one or more $R_b$;

$R_b$ is selected from the group consisting of methoxy, halogen and hydroxy;

$R_c$ is selected from the group consisting of a bond, methyl, C3–6 cycloalkyl, C7–8 bicycloalkyl, phenyl, naphthyl, tetrahydronaphthyl, indanyl, C1–4 alkoxy, C1–3 alkanoylamino, methylthio, halogen, hydroxy, oxo, carboxy and cyano, $R_c$ may be further optionally substituted by one or more $R_d$;

$R_d$ is selected from the group consisting of C1–3 alkyl, phenyl, methoxy, halogen and hydroxy;

R6 is hydrogen;

$R_e$ is selected from the group consisting of a bond, C5–6 cycloalkyl, phenyl, C1–5 alkoxy, C1–5 alkylamino, pyrrolidinyl, piperidinyl, naphthyl, thienyl, indolyl, methoxy, benzyloxy, methylthio, benzylthio, methoxycarbonylamino, halogen, hydroxy, carboxy and cyano, $R_e$ may be further optionally substituted by one or more $R_f$; and $R_f$ is selected from the group consisting of C1–5 alkyl, C3–6 cycloalkyl, phenyl optionally substituted by halogen, methoxy, phenoxy, benzyloxy, methoxycarbonyl, halogen, hydroxy and carboxy.

R6 and R7 together with the carbon they are attached form a cyclopropyl ring or heterocyclic ring selected from the group consisting of pyrrolidinyl and piperidinyl, the cyclopropyl or heterocyclic ring being optionally substituted with one or more $R_g$;

$R_g$ is selected from the group consisting of a bond, C1–8 alkyl, C3–8 cycloalkyl, C7–8 bicycloalkyl, benzyl, α-tetrahydronaphthyl, α-indanyl, tetrahydropyranyl, tetrahydrothiopyranyl and amino wherein the nitrogen atom may be independently mono or di-substituted by C1–5 alkyl, C3–6 cycloalkyl, benzyl or benzoyl, $R_g$ may be further optionally substituted by one or more $R_h$; and $R_h$ is selected from the group consisting of C1–5 alkyl, C3–7 cycloalkyl, phenyl, benzyl, benzyloxy, tetrahydropyranyl, heteroaryl selected from the group consisting of thienyl, pyridinyl, indolyl, pyrrolyl and benzimidazolyl, halogen, hydroxy, oxo, cyano or trifluoromethyl, may be further substituted by $R_i$; and $R_i$ is C1–8 alkyl and halogen.

Even much more preferred are compounds of the formula (Ia) as described immediately above and wherein:

R1 is phenyl, morpholinyl, thiomorpholinyl or pyrrolidinyl, R1 is optionally substituted by one or more $R_a$;

$R_a$ is selected from the group consisting of C1–3 alkyl, methoxy, C1–3 alkylsulfonylamino, halogen, hydroxy, cyano and trifluoromethyl;

R5 is C1–3 alkyl wherein R5 is optionally substituted by one or more $R_c$;

$R_c$ is selected from the group consisting of C3–6 cycloalkyl, C7–8 bicycloalkyl, phenyl, naphthyl, β-tetrahydronaphthyl or β-indanyl, $R_c$ may be further optionally substituted by one or more $R_d$;

$R_d$ is selected from the group consisting of methyl, methoxy and halogen;

R7 is C1–5 alkyl wherein R7 is optionally substituted by one or more $R_e$;

$R_e$ is selected from the group consisting of phenyl, naphthyl, C1–5 alkoxy, C1–5 alkylamino, pyrrolidinyl and piperidinyl, $R_e$ may be further optionally substituted by one or more $R_f$; and $R_f$ is selected from the group consisting of C1–5 alkyl, C3–6 cycloalkyl, phenyl optionally substituted with halogen, halogen and hydroxy, or R6 and R7 together with the carbon they are attached form a cyclopropyl ring or heterocyclic ring selected from the group consisting of piperidinyl and pyrrolidinyl, the cyclopropyl or heterocyclic ring being optionally substituted with one or more $R_g$; and $R_g$ is selected from the group consisting of C1–8 alkyl, C3–8 cycloalkyl, C7–8 bicycloalkyl, benzyl, α-tetrahydronaphthyl, α-indanyl, tetrahydropyranyl, tetrahydrothiopyranyl and amino group wherein the nitrogen atom may be independently mono or disubstuituted by C1–5 alkyl or C3–6 cycloalkyl, $R_g$ may be further optionally substituted by one or more $R_h$; and $R_h$ is selected from the group consisting of C1–5 alkyl, C3–7 cycloalkyl, phenyl, benzyl, benzyloxy, thienyl, pyrrolyl, indolyl, pyridinyl, halogen, hydroxy, cyano and trifluoromethyl; $R_h$ may be further optionally substituted by one or more $R_i$; and $R_i$ is C1–5 alkyl and halogen.

Yet even much more preferred are compounds of the formula (Ia) as described immediately above and wherein:

R1 is 4-morpholinyl or pyrrolidinyl, wherein R1 is optionally substituted by one or more $R_a$;

$R_a$ is C1–3 alkylsulfonylamino;

R5 is C1–3 alkyl wherein R5 is optionally substituted by one or more $R_c$;

$R_c$ is selected from the group consisting of C5–6 cycloalkyl, C7–8 bicycloalkyl, β-tetrahydronaphthyl and β-indanyl, $R_c$ may be further optionally substituted by one or more $R_d$;

$R_d$ is selected from the group consisting of methyl, methoxy and halogen;

R7 is C1–5 alkyl wherein R7 is optionally substituted by one or more $R_e$;

$R_e$ is selected from the group consisting of C1–5 alkoxy, C1–5 alkylamino, pyrrolidinyl and piperidinyl, $R_e$ may be further optionally substituted by one or more $R_f$; and $R_f$ is selected from the group consisting of C1–5 alkyl, C3–6 cycloalkyl, phenyl optionally substituted with halogen, halogen and hydroxy, or R6 and R7 together with the carbon they are attached form heterocyclic ring selected from the group consisting of piperidinyl and pyrrolidinyl, the heterocyclic ring being optionally substituted with one or more $R_g$; and $R_g$ is selected from the group consisting of C1–8 alkyl, C3–8 cycloalkyl, C7–8 bicycloalkyl, benzyl, α-tetrahydronaphthyl, α-indanyl, tetrahydropyranyl and tetrahydrothiopyranyl; $R_g$ may be further optionally substituted by one or more $R_h$; and $R_h$ is selected from the group consisting of C1–5 alkyl, C3–7 cycloalkyl, phenyl, pyridinyl, indolyl, thienyl, halogen, hydroxy, cyano and trifluoromethyl; $R_h$ may be further optionally substituted by one or more $R_i$;

$R_i$ is selected from the group consisting of C1–3 alkyl and halogen.

Ultimately preferred are compounds of the formula (Ia) as described immediately above and wherein:

R1 is 4-morpholinyl;

R5 is C1–3 alkyl wherein R5 is optionally substituted by one or more $R_c$;

$R_c$ is selected from the group consisting of cyclohexyl, β-tetrahydronaphthyl and β-indanyl, $R_c$ may be further optionally substituted by one or more $R_d$;

$R_d$ is selected from the group consisting of methyl and halogen;

R7 is C1–5 alkyl wherein R7 is optionally substituted by one or more $R_e$;

$R_e$ is selected from the group consisting of C1–2 alkoxy and C1–2 alkylamino, $R_e$ may be further optionally substituted by one or more $R_f$;

$R_f$ is selected from the group consisting of C1–3 alkyl, phenyl, halogen and hydroxy;

or R6 and R7 together with the carbon they are attached form a heterocyclic ring selected from the group consisting of piperidinyl and pyrrolidinyl, the heterocyclic ring being optionally substituted with one or more $R_g$; and $R_g$ is selected from the group consisting of C1–5 alkyl, C3–8 cycloalkyl, C7–8 bicycloalkyl, benzyl and α-tetrahydronaphthyl; $R_g$ may be further optionally substituted by one or more $R_h$; and $R_h$ is C1–5 alkyl, C3–7 cycloalkyl, thienyl, pyridinyl, indolyl, halogen, hydroxy and trifluoromethyl; $R_h$ may be further optionally substituted by one or more $R_i$;

Ri is methyl.

The activity of particular compounds disclosed herein against cathepsin K may be determined without undue experimentation by one of ordinary skill in the art in view of the art, the guidance provided throughout this specification and by the art recognized methods referred to in the section entitled "Assessment of Biological Properties."

The following subgeneric aspect of the compounds of the formula (Ia) is postulated to possess Cathepsin K activity:

The broadest embodiment of the formula (Ia) as described hereinabove and wherein A is —C(O)—;

R1 is aryl or aryloxy wherein R1 is optionally substituted by one or more Ra;

R2 is hydrogen;

R3 is hydrogen;

R4 is hydrogen or lower alkyl;

R5 is alkyl optionally substituted by one or more $R_c$;

or R4 and R5 together with the carbon they are attached form a 3 to 7 membered carbocyclic ring optionally substituted with one or more $R_d$;

R6 is hydrogen or lower alkyl wherein one or more carbon atoms are optionally replaced by 1 to two heteroatoms selected from the group consisting of N,O and S;

R7 is hydrogen, alkyl wherein one or more carbon atoms are optionally replaced by 1 to two heteroatoms selected from the group consisting of N,O and S, cycloalkyl, aryl, heterocyclyl, heteroaryl or cyano, wherein R7 is optionally substituted by one or more $R_e$;

R6 and R7 together with the carbon they are attached form a carbocyclic ring selected from the group consisting of cyclopropyl, cyclobutyl, cyclopentyl, cyclohexyl, cycloheptyl or heterocyclic ring selected from the group consisting of azetidinyl, pyrrolidinyl, piperidinyl, tetrahydropyranyl and tetrahydrothiopyranyl, the carbocyclic or heterocyclic ring being optionally substituted with one or more $R_g$;

Preferred cathepsin K inhibitors are those as described immediately above and wherein:

R1 is naphthyl, benzyloxy or phenoxy wherein R1 is optionally substituted by one or more Ra;

R4 is hydrogen or lower alkyl;

R5 is lower alkyl optionally substituted by one or more $R_c$;

or R4 and R5 together with the carbon they are attached form a 5 to 6 membered carbocyclic ring optionally substituted with one or more $R_d$;

R6 is hydrogen or lower alkyl wherein one or more carbon atoms are optionally replaced by N;

R7 is lower alkyl wherein one or more carbon atoms are optionally replaced by heteroatoms selected from the group consisting of N and O, R7 is optionally substituted by one or more $R_e$;

R6 and R7 together with the carbon they are attached form a heterocyclic ring selected from the group consisting of pyrrolidinyl and piperidinyl each being optionally substituted with one or more $R_g$.

Most preferred cathepsin K inhibitors are those as described immediately above and wherein:

R4 is hydrogen or lower alkyl;

R5 is C1–4 alkyl optionally substituted by one or more $R_c$;

or R4 and R5 together with the carbon they are attached form a cyclohexyl ring optionally substituted with one or more $R_d$;

R7 is lower alkyl wherein one or more carbon atoms are optionally replaced by heteroatoms selected from the group consisting of N and O or benzyloxy;

R6 and R7 together with the carbon they are attached form pyrrolidinyl optionally substituted with one or more $R_g$.

The following are representative compounds of the invention:

4-Methyl-2-(2-morpholin-4-yl-2-oxo-ethyl)-pentanoic acid (2-benzyloxy-1-cyano-ethyl)-amide. MS: m/z=402 M+1;

N-(Benzyloxymethyl-cyano-methyl)-2-cyclohexylmethyl-4-morpholin-4-yl-4-oxo-butyramide;

N-(1-Cyano-3-phenyl-propyl)-2-cyclohexylmethyl-4-morpholin-4-yl-4-oxo-butyramide. MS: m/z=426 M+1;

4,4-Dimethyl-2-(2-morpholin-4-yl-2-oxo-ethyl)-pentanoic acid (2-benzyloxy-1-cyano-ethyl)-amide. MS: m/z=416 M+1;

4,4-Dimethyl-2-(2-morpholin-4-yl-2-oxo-ethyl)pentanoic acid (1-cyano-3-phenyl-propyl)-amide. MS: m/z=400 M+1;

2-(Morpholine-4-carbonyl)-cyclohexanecarboxylic acid (benzyloxymethyl-cyano-methyl)-amide;

N-(2-Benzyloxy-1-cyano-ethyl)-4-morpbolin-4-yl-2-naphthalen-2-ylmethyl-4-oxo-butyramide. MS: m/z=486 M+1;

N-[2-(4-Chloro-benzyloxy)-1-cyano-ethyl]-2-cyclohexylmethyl-4-morpholin-4-yl-4-oxo-butyramide. MS: m/z=477 M+1;

$N^1$-(Benzyloxymethyl-cyano-methyl)-$N^4$-[4-(5-chloro-H-benzoimidazol-2-yl)-phenyl]-2-cyclohexymethyl-succinamide;

$N^4$-[2-(4-Acetylamino-phenyl)-$N^1$-(2-benzyloxy)-1-cyano-ethyl]-2-cyclohexylmethyl-succinamide. MS: m/z=505 M+1;

N-(cyano-1-methyl-piperidin-4-yl)-2-cyclohexylmethyl-4-morpholin-4-yl-4-oxo-butyramide;

N-(cyano-cyclopropyl)-2-cyclohexylmethyl-4-morpholin-4-yl-4-oxo-butyramide;

N-(cyano-1-benzyl-pyrrolidin-3-ylcarbamoyl)-2-cyclohexylmethyl-4-morpholin-4-yl-4-oxo-butyramide;

4,4-Dimethyl-2-(2-morpholin-4-yl-2-oxo-ethyl)-pentanoic acid (4-cyano-1-propyl-piperidin-4-yl)-amide. MS: m/z=407 M+1;

4,4-Dimethyl-2-(2-morpholin-4-yl-2-oxo-ethyl)-pentanoic acid (1-benzyl-4-cyano-piperidin-4-yl)-amide. MS: m/z=455 M+1;

N-(1-Benzyl-4-cyano-piperidin-4-yl)-2-cyclohexylmethyl-4-morpholin-4-yl-4-oxo-butyramide. MS: m/z=481 M+1;

N-[1-(3-Benzyloxy-benzyl)-3-cyano-pyrrolidin-3-yl]-2-cyclohexylmethyl-4-morpholin-4-yl-4-oxo-butyramide. MS: m/z=573 M+1;

N-(3-Cyano-1-cyclohexylmethyl-pyrrolidin-3-yl)-2-cyclohexylmethyl-4-morpholin-4-yl-4-oxo-butyramide. MS: m/z=473 M+1;

N-[3-Cyano-1-(2,6-difluoro-benzyl)-pyrrolidin-3-yl]-2-cyclohexylmethyl-4-morpholin-4-yl-4-oxo-butyramide. MS: m/z 503 M+1;

N-[3-Cyano-1-(3,5-difluoro-benzyl)-pyrrolidin-3-yl]-2-cyclohexylmethyl-4-morpholin-4-yl-4-oxo-butyramide. MS: m/z=503 M+1;

N-[3-Cyano-1-(3-trifluoromethyl-benzyl)-pyrrolidin-3-yl]-2-cyclohexylmethyl-4-morpholin-4-yl-4-oxo-butyramide. MS: m/z=535 M+1;

N-(3-Cyano-1-cyclohexyl-pyrrolidin-3-yl)-2-cyclohexylmethyl-4-morpholin-4-yl-4-oxo-butyramide. MS: m/z=459 M+1;

4,4-Dimethyl-2-[2-(4-methyl-piperazin-1-yl)-2-oxo-ethyl]-pentanoic acid (3-cyano-1-cyclohexylmethyl-pyrrolidin-3-yl)-amide. MS: m/z=460 M+1;

4,4-Dimethyl-2-(2-morpholin-4-yl-2-oxo-ethyl)-pentanoic acid (3-cyano-1-cyclohexylmethyl-pyrrolidin-3-yl)-amide. MS: m/z=447 M+1;

4,4-Dimethyl-2-(2-oxo-2-piperidin-1-yl-ethyl)-pentanoic acid (3-cyano-1-cyclohexylmethyl-pyrrolidin-3-yl)-amide. MS: m/z=445 M+1;

4,4-Dimethyl-2-(2-oxo-2-thiomorpholin-4-yl-ethyl)-pentanoic acid (3-cyano-1-cyclohexylmethyl-pyrrolidin-3-yl)-amide. MS: m/z=463 M+1;

N-(3-cyano-1-(3,3-dimethyl-butyl)pyrrolidin-3-ylcarbamoyl)-2-cyclohexylmethyl-4-morpholin-4-yl-4-oxo-butyramide;

N-(3-Cyano-1-isopropyl-pyrrolidin-3-yl)-2-cyclohexylmethyl-4-morpholin-4-yl-4-oxo-butyramide. MS: m/z=419 M+1;

N-(3-Cyano-1-methyl-pyrrolidin-3-yl)-2-cyclohexylmethyl-4-morpholin-4-yl-4-oxo-butyramide. MS: m/z=391 M+1;

N-[3-Cyano-1-(1-ethyl-propyl)-pyrrolidin-3-yl]-2-cyclohexylmethyl-4-morpholin-4-yl-4-oxo-butyramide. MS: m/z=447 M+1;

N-(3-Cyano-1-isobutyl-pyrrolidin-3-yl)-2-cyclohexylmethyl-4-morpholin-4-yl-4-oxo-butyramide. MS: m/z=433 M+1;

N-(3-Cyano-1-cyclopropylmethyl-pyrrolidin-3-yl)-2-cyclohexylmethyl-4-morpholin-4-yl-4-oxo-butyramide. MS: m/z=431 M+1;

N-(3-Cyano-1-phenethyl-pyrrolidin-3-yl)-2-cyclohexyhnethyl-4-morpholin-4-yl-4-oxo-butyramide. MS: m/z=481 M+1;

N-(3-Cyano-1-methyl-piperidin-3-yl)-2-cyclohexylmethyl-4-morpholin-4-yl-4-oxo-butyramide. MS: m/z=405 M+1;

N-[3-Cyano-1-(4-methyl-cyclohexyl)-pyrrolidin-3-yl]-2-cyclohexylmethyl-4-morpholin-4-yl-4-oxo-butyramide. MS: m/z=473 M+1;

N-(3-Cyano-1-propyl-pyrrolidin-3-yl)-2-cyclohexylmethyl-4-morpholin-4-yl-4-oxo-butyramide. MS: m/z=419 M+1;

N-(3-Cyano-1-cyclopentyl-pyrrolidin-3-yl)-2-cyclohexylmethyl-4-morpholin-4-yl-4-oxo-butyramide. MS: m/z=445 M+1;

N-(1-cyano-3-piperidin-1-yl-propyl)-2-cyclohexylmethyl-4-morpholin-4-yl-4-oxo-butyramide;

(4R)-N-(3-Cyano-1-cyclohexyl-pyrrolidin-3-yl)-2-(1-methyl-cyclohexylmethyl)-4-morpholin-4-yl-4-oxo-butyramide;

N-[1-Cyano-3-(cyclohexyl-ethyl-amino)-propyl]-2-cyclohexylmethyl-4-morpholin-4-yl-4-oxo-butyramide. MS: m/z=475 M+1;

N-[3-(Benzyl-isopropyl-amino)-1-cyano-propyl]-2-cyclohexylmethyl-4-morpholin-4-yl-4-oxo-butyramide. MS: m/z=497 M+1;

N-[3-Cyano-1-(1H-indol-2-ylmethyl)-pyrrolidin-3-yl]-2-cyclohexylmethyl-4-morpholin-4-yl-4-oxo-butyramide;

$N^4$-Carbamoylmethyl-$N^1$-(3-cyano-1-cyclohexyl-pyrrolidin-3-yl)-2-cyclohexylmethyl-$N^4$-methyl-succinamide;

N-(3-Cyano-1-cycloheptyl-pyrrolidin-3-yl)-2-cyclohexylmethyl-4-morpholin-4-yl-4-oxo-butyramide. MS: m/z=473 M+1;

N-[3-Cyano-1-(1,2,3,4-tetrahydro-naphthalen-1-yl)-pyrrolidin-3-yl]-2-cyclohexylmethyl-4-morpholin-4-yl-4-oxo-butyramide. MS: m/z=507 M+1;

N-(1-Bicyclo[2.2.1]hept-2-yl-3-cyano-pyrrolidin-3-yl)-2-cyclohexylmethyl-4-morpholin-4-yl-4-oxo-butyramide. MS: m/z=471 M+1;

N-(4-Cyano-1-propyl-piperidin-4-yl)-2-cyclohexylmethyl-4-morpholin-4-yl-4-oxo-butyramide. MS: m/z=433 M+1;

N-(1-Benzyl-4-cyano-piperidin-4-yl)-2-cyclohexylmethyl-4-morpholin-4-yl-4-oxo-butyramide. MS: m/z=487 M+1;

N-[3-Cyano-1-(tetrahydro-pyran-4-yl)-pyrrolidin-3-yl]-2-cyclohexylmethyl-4-morpholin-4-yl-4-oxo-butyramide, MS: m/z 461=M+1;

N-[3-Cyano-1-(tetrahydro-thiopyran-4-yl)-pyrrolidin-3-yl]-2-cyclohexylmethyl-4-morpholin-4-yl-4-oxo-butyramide, MS: m/z 477=M+1;

N-[3-Cyano-1-(tetrahydro-thiopyran-4-yl)-pyrrolidin-3-yl]-2-cyclohexylmethyl-4-morpholin-4-yl-4-oxo-butyramide, MS: m/z 477=M+1;

N-[3-Cyano-1-(2-phenyl-benzyl)-pyrrolidin-3-yl]-2-cyclohexylmethyl-4-morpholin-4-yl-4-oxo-butyramide; MS, m/z 543=M+1;

N-[3-Cyano-1-(3-phenyl-benzyl)-pyrrolidin-3-yl]-2-cyclohexylmethyl-4-morpholin-4-yl-4-oxo-butyramide; MS, m/z 543=M+1;

N-{1-[(benzyl-methyl-amino)-methyl]-1-cyano-3-phenyl-propyl}-2-cyclohexylmethyl-4-morpholin-4-yl-4-oxo-butyramide;

N-(4-Cyano-1,2-dimethyl-piperidin-4-yl)-2-cyclohexylmethyl-4-morpholin-4-yl-4-oxo-butyramide;

(4R)-N-(3-Cyano-1-cyclohexyl-pyrrolidin-3-yl)-2-(4-methyl-cyclohexylmethyl)-4-morpholin-4-yl-4-oxo-butyramide;

N-(3-Cyano-1-cyclohexyl-pyrrolidin-3-yl)-4-morpholin-4-yl-4-oxo-2-(trans-4-phenyl-cyclohexylmethyl)-butyramide;

2-Bicyclo[4.1.0]hept-7-ylmethyl-N-(3-cyano-1-cyclohexyl-pyrrolidin-3-yl)-4-morpholin-4-yl-4-oxo-butyramide;

2-Bicyclo[4.1.0]hept-7-ylmethyl-N-(4-cyano-1-methyl-piperidin-4-yl)-4-morpholin-4-yl-4-oxo-butyramide;

N-(3-Cyano-1-cyclohexyl-pyrrolidin-3-yl)-4-morpholin-4-yl-4-oxo-2-(1,2,3,4-tetrahydro-naphthalen-2-ylmethyl)-butyramide; MS, m/z 507=M+1;

N-(3-Cyano-1-cyclohexyl-pyrrolidin-3-yl)-2-indan-2-ylmethyl-4-morpholin-4-yl-4-oxo-butyramide; MS, m/z 493=M+1;

N-(3-Cyano-1-cyclohexyl-pyrrolidin-3-yl)-2-cyclopentylmethyl-4-morpholin-4-yl-4-oxo-butyramide; MS, m/z 445=M+1;

[2-Cyano-2-(2-cyclohexylmethyl-4-morpholin-4-yl-4-oxo-butyrylamino)-ethyl]-carbamic acid tert-butyl ester;

N-{Cyano-[(cyclohexyl-ethyl-amino)-methyl]-methyl}-2-cyclohexylmethyl-4-morpholin-4-yl-4-oxo-butyramide;

N-{Cyano-[(dibenzylamino)-methyl]-methyl}-2-cyclohexylmethyl-4-morpholin-4-yl-4-oxo-butyramide;
N-{[(Benzyl-ethyl-amino)-methyl]-cyano-methyl}-2-cyclohexylmethyl-4-morpholin-4-yl-4-oxo-butyramide;
N-(Cyano-piperidin-1-ylmethyl-methyl)-2-cyclohexylmethyl-4-morpholin-4-yl-4-oxo-butyramide;
{1-[3-(1-Benzyl-3-cyano-pyrrolidin-3-yl carbamoyl)-4-cyclohexyl-butyryl]-pyrrolidin-3-yl}-carbamic acid tert-butyl ester. MS: m/z=566.5 M+1;
{1-[3-(3-Cyano-1-cyclohexyl-pyrrolidin-3-yl carbamoyl)-4-cyclohexyl-butyryl]-pyrrolidin-3-yl}-carbamic acid tert-butyl ester. MS: m/z=558.6 M+1;
N-(1-Benzyl-3-cyano-pyrrolidin-3-yl)-2-cyclohexylmethyl-4-(3-dimethylamino-pyrrolidin-1-yl)-4-oxo-butyramide. MS: m/z=494.5 M+1;
N-(1-Benzyl-3-cyano-pyrrolidin-3-yl)-2-cyclohexylmethyl-4-(3-methanesulfonylamino-pyrrolidin-1-yl)-4-oxo-butyramide. MS: m/z=544.4 M+1;
N-(3-Cyano-1-cyclohexyl-pyrrolidin-3-yl)-2-cyclohexylmethyl-4-(3-methanesulfonylamino-pyrrolidin-1-yl)-4-oxo-butyramide. MS: m/z=536.4 M+1;
N-[(3S)-3-Cyano-1-trans-(4-ethyl-cyclohexyl)-pyrrolidin-3-yl]-(2R)-2-cyclohexylmethyl-4-morpholin-4-yl-4-oxo-butyramide;
N-[(3R)-3-Cyano-1-trans-(4ethyl-cyclohexyl)-pyrrolidin-3-yl]-(2R)-2-cyclohexylmethyl-4-morpholin-4-yl-4-oxo-butyramide;
N-[(3S)-3-Cyano-1-cis-(4-ethyl-cyclohexyl)-pyrrolidin-3-yl]-(2R)-2-cyclohexylmethyl-4-morpholin-4-yl-4-oxo-butyramide;
N-[(3R)-3-Cyano-1-cis-(4-ethyl-cyclohexyl)-pyrrolidin-3-yl]-(2R)-2-cyclohexylmethyl-4-morpholin-4-yl-4-oxo-butyramide;
N-[(3S)-3-Cyano-1-trans-(4isopropyl-cyclohexyl)-pyrrolidin-3-yl]-(2R)-2-cyclohexylmethyl-4-morpholin-4-yl-4-oxo-butyramide;
N-[(3R)-3-Cyano-1-trans-(4-isopropyl-cyclohexyl)-pyrrolidin-3-yl]-(2R)-2-cyclohexylmethyl-4-morpholin-4-yl-4-oxo-butyramide;
N-[(3S)-3-Cyano-1cis-(4-isopropyl-cyclohexyl)-pyrrolidin-3-yl]-(2R)-2-cyclohexylmethyl-4-morpholin-4-yl-4-oxo-butyramide;
N-[(3R)-3-Cyano-1-cis-(4-isopropyl-cyclohexyl)-pyrrolidin-3-yl]-(2R)-2-cyclohexylmethyl-4-morpholin-4-yl-4-oxo-butyramide;
N-[1-trans-(4tert-Butyl-cyclohexyl)-(3S)-3-cyano-pyrrolidin-3-yl]-(2R)-2-cyclohexylmethyl-4-morpholin-4-yl-4-oxo-butyramide;
N-[1-trans-(4-tert-Butyl-cyclohexyl)-(3R)-3-cyano-pyrrolidin-3-yl]-(2R)-2-cyclohexylmethyl-4-morpholin-4-yl-4-oxo-butyramide;
N-[1-cis-(4-tert-Butyl-cyclohexyl)-(3S)-3-cyano-pyrrolidin-3-yl]-(2R)-2-cyclohexylmethyl-4-morpholin-4-yl-4-oxo-butyramide;
N-[1-cis-(4-tert-Butyl-cyclohexyl)-(3R)-3-cyano-pyrrolidin-3-yl]-(2R)-2-cyclohexylmethyl-4-morpholin-4-yl-4-oxo-butyramide; N-[(3S)-3-cyano-1-cis-(3-methyl-cyclohexyl)-pyrrolidin-3-yl]-(2R)-2-cyclohexylmethyl-4-morpholin-4-yl-4-oxo-butyramide;
N-[(3R)-3-cyano-1-cis-(3-methyl-cyclohexyl)-pyrrolidin-3-yl]-(2R)-2-cyclohexylmethyl-4-morpholin-4-yl-4-oxo-butyramide;
N-[(3S)-3-cyano-1-trans-(3-methyl-cyclohexyl)-pyrrolidin-3-yl]-(2R)-2-cyclohexylmethyl-4-morpholin-4-yl-4-oxo-butyramide;
N-[(3R)-3-cyano-1-trans-(3-methyl-cyclohexyl)-pyrrolidin-3-yl]-(2R)-2-cyclohexylmethyl-4-morpholin-4-yl-4-oxo-butyramide;
N-[(3S)-3-Cyano-1-(3,3-dimethyl-cyclohexyl)-pyrrolidin-3-yl]-(2R)-2-cyclohexylmethyl-4-morpholin-4-yl-4-oxo-butyramide;
N-[(3R)-3-Cyano-1-(3,3-dimethyl-cyclohexyl)-pyrrolidin-3-yl]-(2R)-2-cyclohexylmethyl-4-morpholin-4-yl-4-oxo-butyramide;
N-[(3S)-3-Cyano-1-cis-(3-isopropyl-cyclohexyl)-pyrrolidin-3-yl]-(2R)-2-cyclohexylmethyl-4-morpholin-4-yl-4-oxo-butyramide;
N-[(3R)-3-Cyano-1-cis-(3-isopropyl-cyclohexyl)-pyrrolidin-3-yl]-(2R)-2-cyclohexylmethyl-4-morpholin-4-yl-4-oxo-butyramide;
N-[(3S)-3-Cyano-1-trans-(3-isopropyl-cyclohexyl)-pyrrolidin-3-yl]-(2R)-2-cyclohexylmethyl-4-morpholin-4-yl-4-oxo-butyramide;
N-[(3R)-3-Cyano-1-trans-(3-isopropyl-cyclohexyl)-pyrrolidin-3-yl]-(2R)-2-cyclohexylmethyl-4-morpholin-4-yl-4-oxo-butyramide;
N-[(3S)-3-Cyano-1-cis-(2-methyl-cyclohexyl)-pyrrolidin-3-yl]-(2R)-2-cyclohexylmethyl-4-morpholin-4-yl-4-oxo-butyramide;
N-[(3R)-3-Cyano-1-cis-(2-methyl-cyclohexyl)-pyrrolidin-3-yl]-(2R)-2-cyclohexylmethyl-4-morpholin-4-yl-4-oxo-butyramide;
N-[(3S)-3-Cyano-1-trans-(2-methyl-cyclohexyl)-pyrrolidin-3-yl]-(2R)-2-cyclohexylmethyl-4-morpholin-4-yl-4-oxo-butyramide;
N-[(3R)-3-Cyano-1-trans-(2-methyl-cyclohexyl)-pyrrolidin-3-yl]-(2R)-2-cyclohexylmethyl-4-morpholin-4-yl-4-oxo-butyramide;
N-[(3S)-3-Cyano-1-cis-(2-ethyl-cyclohexyl)-pyrrolidin-3-yl]-(2R)-2-cyclohexylmethyl-4-morpholin-4-yl-4-oxo-butyramide;
N-[(3R)-3-Cyano-1-cis-(2-ethyl-cyclohexyl)-pyrrolidin-3-yl]-(2R)-2-cyclohexylmethyl-4-morpholin-4-yl-4-oxo-butyramide;
N-[(3S)-3-Cyano-1-trans-(2-ethyl-cyclohexyl)-pyrrolidin-3-yl]-(2R)-2-cyclohexylmethyl-4-morpholin-4-yl-4-oxo-butyramide;
N-[(3R)-3-Cyano-1-trans-(2-ethyl-cyclohexyl)-pyrrolidin-3-yl]-(2R)-2-cyclohexylmethyl-4-morpholin-4-yl-4-oxo-butyramide;
N-[(3S)-3-Cyano-1-(2,2-dimethyl-cyclohexyl)-pyrrolidin-3-yl]-(2R)-2-cyclohexylmethyl-4-porpholin-4-yl-4-oxo-butyramide;
N-[(3R)-3-Cyano-1-(2,2-dimethyl-cyclohexyl)-pyrrolidin-3-yl]-(2R)-2-cyclohexylmethyl-4-morpholin-4-y)-4-oxo-butyramide;
N-[(3S)-3-Cyano-1-(4,4-dimethyl-cyclohexyl)-pyrrolidin-3-yl]-(2R)-2-cyclohexylmethyl-4-morpholin-4-yl-4-oxo-butyramide;
N-[(3R)-3-Cyano-1-(4,4-dimethyl-cyclohexyl)-pyrrolidin-3-yl]-(2R)-2-cyclohexylmethyl-4-morpholin-4yl-4-oxo-butyramide;
N-[(3S)-3-Cyano-1-(2-methyl-2-phenyl-propyl)-pyrrolidin-3-yl]-(2R)-2-cyclohexylmethyl-4-morpholin-4-yl-4-oxo-butyramide;
N-[(3R)-3-Cyano-1-(2-methyl-2-phenyl-propyl)-pyrrolidin-3-yl]-(2R)-2-cyclohexylmethyl-4-morpholin-4-yl-4-oxo-butyramide;
N-[(S)-Cyano-methyl-phenyl-methyl]-(2R)-2-cyclohexylmethyl-4-morpholin-4-yl-4-oxo-butyramide;
N-[(R)-Cyano-methyl-phenyl-methyl]-(2R)-2-cyclohexylmethyl-4-morpholin-4-yl-4-oxo-butyramide;
N-[(S)-Cyano-methyl-pyridin-4-yl-methyl]-(2R)-2-cyclohexylmethyl-4-morpholin-4-yl-4-oxo-butyramide;
N-[(R)-Cyano-methyl-pyridin-4-yl-methyl]-(2R)-2-cyclohexylmethyl-4-morpholin-4-yl-4-oxo-butyramide;

N-[(3S)-3-Cyano-1-indan-2-ylmethyl-pyrrolidin-3-yl]-(2R)-2-cyclohexylmethyl-4-morpholin-4-yl-4-oxo-butyramide;

N-[(3R)-3-Cyano-1-indan-2-ylmethyl-pyrrolidin-3-yl]-(2R)-2-cyclohexylmethyl-4-morpholin-4-yl-4-oxo-butyramide;

N-[(3S)-3-Cyano-1-(5-methyl-thiophen-2-ylmethyl)-pyrrolidin-3-yl]-(2S)-2-cyclohexylmethyl-4-morpholin-4-yl-4-oxo-butyramide;

N-[(3S)-3-Cyano-1-(5-methyl-thiophen-2-ylmethyl)-pyrrolidin-3-yl]-(2S)-2-cyclohexylmethyl-4-morpholin-4-yl-4-oxo-butyramide;

N-[(3S)-3-Cyano-pyrrolidin-3-yl]-(2R)-2-cyclohexylmethyl-4-morpholin-4-yl-4-oxo-butyramide;

N-[(3R)-3-Cyano-pyrrolidin-3-yl]-(2R)-2-cyclohexylmethyl-4-morpholin-4-yl-4-oxo-butyramide and the pharmaceutically acceptable salts, esters or tautomers thereof.

Of the aforementioned compounds, preferred are the following:

4-Methyl-2-(2-morpholin-4-yl-2-oxo-ethyl)-pentanoic acid (2-benzyloxy-1-cyano-ethyl)-amide. MS: m/z=402 M+1;

N-(Benzyloxymethyl-cyano-methyl)-2-cyclohexylmethyl-4-morpholin-4-yl-4-oxo-butyramide;

N-(1-Cyano-3-phenyl-propyl)-2-cyclohexylmethyl-4-morpholin-4-yl-4-oxo-butyramide. MS: m/z=426 M+1;

4,4-Dimethyl-2-(2-morpholin-4-yl-2-oxo-ethyl)-pentanoic acid (2-benzyloxy-1-cyano-ethyl)-amide. MS: m/z=416 M+1;

4,4-Dimethyl-2-(2-morpholin-4-yl-2-oxo-ethyl)-pentanoic acid (1-cyano-3-phenyl-propyl)-amide. MS: m/z=400 M+1;

N-(2-Benzyloxy-1-cyano-ethyl)-4-morpholin-4-yl-2-naphthalen-2-ylmethyl-4-oxo-butyramide. MS: m/z=486 M+1;

N-[2-(4-Chloro-benzyloxy)-1-cyano-ethyl]-2-cyclohexylmethyl-4-morpholin-4-yl-4-oxo-butyramide. MS: m/z=477 M+1;

N-(cyano-methyl-piperidin-4-yl)-2-cyclohexylmethyl-4-morpholin-4-yl-4-oxo-butyramide;

N-(cyano-cyclopropyl)-2-cyclohexylmethyl-4-morpholin-4-yl-4-oxo-butyramide;

N-(cyano-1-benzyl-pyrrolidin-3-ylcarbamoyl)-2-cyclohexylmethyl-4-morpholin-4-yl-4-oxo-butyramide;

N-(1-Benzyl-4-cyano-piperidin-4-yl)-2-cyclohexylmethyl-4-morpholin-4-yl-4-oxo-butyramide. MS: m/z=481 M+1;

N-[1-(3-Benzyloxy-benzyl)-3-cyano-pyrrolidin-3-yl]-2-cyclohexylmethyl-4-morpholin-4-yl-4-oxo-butyramide. MS: m/z=573 M+1;

N-(3-Cyano-1-cyclohexylmethyl-pyrrolidin-3-yl)-2-cyclohexylmethyl-4-morpholin-4-yl-4-oxo-butyramide. MS: m/z=473 M+1;

N-[3-Cyano-1-(2,6-difluorobenzyl)-pyrrolidin-3-yl]-2-cyclohexylmethyl-4-morpholin-4-yl-4-oxo-butyramide. MS: m/z=503 M+1;

N-[3-Cyano-1-(3,5-difluoro-benzyl)-pyrrolidin-3-yl]-2-cyclohexylmethyl-4-morpholin-4-yl-4-oxo-butyramide. MS: m/z=503 M+1;

N-[3-Cyano-1-(3-trifluoromethyl-benzyl)-pyrrolidin-3-yl]-2-cyclohexylmethyl-4-morpholin-4-yl-4-oxo-butyramide. MS: m/z=535 M+1;

N-(3-Cyano-1-cyclohexyl-pyrrolidin-3-yl)-2-cyclohexylmethyl-4-morpolin-4-yl-4-oxo-butyramide. MS: m/z=459 M+1;

4,4-Dimethyl-2-(2-morpholin-4-yl-2-oxo-ethyl)-pentanoic acid (3-cyano-1-cyclohexylmethyl-pyrrolidin-3-yl)-amide. MS: m/z=447 M+1;

4,4-Dimethyl-2-(2-oxo-2-thiomorpholin-4-yl-ethyl)-pentanoic acid (3-cyano-1-cyclohexylmethyl-pyrrolidin-3-yl)-amide. MS: m/z=463 M+1;

N-(3-cyano-1-(3,3-dimethyl-butyl)-pyrrolidin-3-ylcarbamoyl)-2-cyclohexylmethyl-4-morpholin-4-yl-4-oxo-butyramide;

N-(3-Cyano-1-isopropyl-pyrrolidin-3-yl)-2-cyclohexylmethyl-4-morpholin-4-yl-4-oxo-butyramide. MS: m/z=419 M+1;

N-(3-Cyano-1-methyl-pyrrolidin-3-yl)-2-cyclohexylmethyl-4-morpholin-4-yl-4-oxo-butyramide. MS: m/z=391 M+1;

N-[3-Cyano-1-(1-ethyl-propyl)-pyrrolidin-3-yl]-2-cyclohexylmethyl-4-morpholin-4-yl-4-oxo-butyramide. MS: m/z=447 M+1;

N-(3-Cyano-1-isobutyl-pyrrolidin-3-yl)-2-cyclohexylmethyl-4-morpholin-4-yl-4-oxo-butyramide. MS: m/z=433 M+1;

N-(3-Cyano-1-cyclopropylmethyl-pyrrolidin-3-yl)-2-cyclohexylmethyl-4-morpholin-4-yl-4-oxo-butyramide. MS: m/z=431 M+1;

N-(3-Cyano-1-phenethyl-pyrrolidin-3-yl)-2-cyclohexylmethyl-4-morpholin-4-yl-4-oxo-butyramide. MS: m/z=481 M+1;

N-(3-Cyano-1-methyl-piperidin-3-yl)-2-cyclohexylmethyl-4-morpholin-4-yl-4-oxo-butyramide. MS: m/z=405 M+1;

N-[3-Cyano-1-(4-methyl-cyclohexyl)-pyrrolidin-3-yl]-2-cyclohexylmethyl-4-morpholin-4-yl-4-oxo-butyramide. MS: m/z=473 M+1;

N-(3-Cyano-1-propyl-pyrrolidin-3-yl)-2-cyclohexylmethyl-4-morphoin-4-yl-4-oxo-butyramide. MS: m/z=419 M+1;

N-(3-Cyano-1-cyclopentyl-pyrrolidin-3-yl)-2-cyclohexylmethyl-4-morpholin-4-yl-4-oxo-butyramide. MS: m/z=445 M+1;

(4R)-N-(3-Cyano-1-cyclohexyl-pyrrolidin-3-yl)-2-(1-methyl-cyclohexylmethyl)-4-morpholin-4-yl-4-oxo-butyramide;

N-[1-Cyano-3-(cyclohexyl-ethyl-amino)-propyl]-2-cyclohexylmethyl-4-morpholin-4-yl-4-oxo-butyramide. MS: m/z=475 M+1;

N-[3-(Benzyl-isopropyl-amino)-1-cyano-propyl]-2-cyclohexylmethyl-4-morpholin-4-yl-4-oxo-butyramide. MS: m/z=497 M+1;

N-[3-Cyano-1-(1H-indol-2-ylmethyl)-pyrrolidin-3-yl]-2-cyclohexylmethyl-4-morpholin-4-yl-4-oxo-butyramide;

$N^4$-Carbamoylmethyl-$N^1$-(3-cyano-1-cyclohexyl-pyrrolidin-3-yl)-2-cyclohexylmethyl-$N^4$-methyl-succinamide;

N-(3-Cyano-1-cycloheptyl-pyrrolidin-3-yl)-2-cyclohexylmethyl-4-morpholin-4-yl-4-oxo-butyramide. MS: m/z=473 M+1;

N-[3-Cyano-1-(1,2,3,4-tetrahydro-naphthalen-1-yl)-pyrrolidin-3-yl]-2-cyclohexylmethyl-4-morpholin-4-yl-4-oxo-butyramide. MS: m/z=507 M+1;

N-(1-Bicyclo[2.2.1]hept-2-yl-3-cyano-pyrrolidin-3-yl)-2-cyclohexylmethyl-4-morpholin-4-yl-4-oxo-butyramide. MS: m/z=471 M+1;

N-(4-Cyano-1-propyl-piperidin-4-yl)-2-cyclohexylmethyl-4-morpholin-4-yl-4-oxo-butyramide. MS: m/z=433 M+1;

N-(1-Benzyl-4-cyano-piperidin-4-yl)-2-cyclohexylmethyl-4-morpholin-4-yl-4-oxo-butyramide. MS: m/z=487 M+1;

N-[3-Cyano-1-(tetrahydro-pyran-4-yl)-pyrrolidin-3-yl]-2-cyclohexylmethyl-4-morpholin-4-yl-4-oxo-butyramide, MS: m/z 461=M+1;

N-[3-Cyano-1-(tetrahydro-thiopyran-4-yl)-pyrrolidin-3-yl]-2-cyclohexylmethyl-4-morpholin-4-yl-4-oxo-butyramide, MS: m/z 477=M+1;

N-[3-Cyano-1-(tetrahydro-thiopyran-4-yl)-pyrrolidin-3-yl]-2-cyclohexylmethyl-4-morpholin-4-yl-4-oxo-butyramide, MS: m/z 477=M+1;

N-[3-Cyano-1-(2-phenyl-benzyl)-pyrrolidin-3-yl]-2-cyclohexylmethyl-4-morpholin-4-yl-4-oxo-butyramide; MS, m/z 543=M+1;

N-[3-Cyano-1-(3-phenyl-benzyl)-pyrrolidin-3-yl]-2-cyclohexylmethyl-4-morpholin-4-yl-4-oxo-butyramide; MS, m/z 543=M+1;

(4R)-N-(3-Cyano-1-cyclohexyl-pyrrolidin-3-yl)-2-(4-methyl-cyclohexylmethyl)-4-morpholin-4-yl-4-oxo-butyramide;

2-Bicyclo[4.1.0]hept-7-ylmethyl-N-(3-cyano-1-cyclohexyl-pyrrolidin-3-yl)-4-morpholin-4-yl-4-oxo-butyramide;

2-Bicyclo[4.1.0]hept-7-ylmethyl-N-(4-cyano-1-methyl-piperidin-4-yl)-4-morpholin-4-yl-4-oxo-butyramide;

N-(3-Cyano-1-cyclohexyl-pyrrolidin-3-yl)-4-morpholin-4-yl-4-oxo-2-(1,2,3,4-tetrahydro-naphthalen-2-ylmethyl)-butyramide; MS, m/z 507=M+1;

N-(3-Cyano-1-cyclohexyl-pyrrolidin-3-yl)-2-indan-2-ylmethyl-4-morpholin-4-yl-4-oxo-butyramide; MS, m/z 493=M+1;

N-(3-Cyano-1-cyclohexyl-pyrrolidin-3-yl)-2-cyclopentylmethyl-4-morpholin-4-yl-4-oxo-butyramide; MS, m/z 445=M+1;

[2-Cyano-2-(2-cyclohexylmethyl-4-morpholin-4-yl-4-oxo-butyrylamino)-ethyl]-carbamic acid tert-butyl ester;

N-{Cyano-[(cyclohexyl-ethyl-amino)-methyl]-methyl}-2-cyclohexylmethyl-4-morpholin-4-yl-4-oxo-butyramide;

N-{Cyano-[(dibenzylamino)-methyl]-methyl}-2-cyclohexylmethyl-4-morpholin-4-yl-4-oxo-butyramide;

N-{[(Benzyl-ethyl-amino)-methyl]-cyano-methyl}-2-cyclohexylmethyl-4-morpholin-4-yl-4-oxo-butyramide;

N-(Cyano-piperidin-1-ylmethyl-methyl)-2-cyclohexylmethyl-4-morpholin-4-yl-4-oxo-butyramide;

{1-[3-(1-Benzyl-3-cyano-pyrrolidin-3-yl carbamoyl)-4-cyclohexyl-butyryl]-pyrrolidin-3-yl}-carbamic acid tert-butyl ester. MS: m/z=566.5 M+1;

{1-[3-(3-Cyano-1-cyclohexyl-pyrrolidin-3-yl carbamoyl)-4-cyclohexyl-butyryl]-pyrrolidin-3-yl}-carbamic acid tert-butyl ester. MS: m/z=558.6 M+1;

N-(1-Benzyl-3-cyano-pyrrolidin-3-yl)-2-cyclohexylmethyl-4-(3-dimethylamino-pyrrolidin-1-yl)-4-oxo-butyramide. MS: m/z=494.5 M+1;

N-(1-Benzyl-3-cyano-pyrrolidin-3-yl)-2-cyclohexylmethyl-4-(3-methanesulfonylamino-pyrrolidin-1-yl)-4-oxo-butyramide. MS: m/z=544.4 M+1;

N-(3-Cyano-1-cyclohexyl-pyrrolidin-3-yl)-2-cyclohexylmethyl-4-(3-methanesulfonylamino-pyrrolidin-1-yl)-4-oxo-butyramide. MS: m/z=536.4 M+1;

N-[(3S)-3-Cyano-1-trans-(4-ethyl-cyclohexyl)-pyrrolidin-3-yl]-(2R)-2-cyclohexylmethyl-4-morpholin-4-yl-4-oxo-butyramide;

N-[(3R)-3-Cyano-1-trans-(4-ethyl-cyclohexyl)-pyrrolidin-3-yl]-(2R)-2-cyclohexylmethyl-4-morpholin-4-yl-4-oxo-butyramide;

N-[(3S)-3-Cyano-1-cis-(4-ethyl-cyclohexyl)-pyrrolidin-3-yl]-(2R)-2-cyclohexylmethyl-4-morpholin-4-yl-4-oxo-butyramide;

N-[(3R)-3-Cyano-1-cis-(4-ethyl-cyclohexyl)-pyrrolidin-3-yl]-(2R)-2-cyclohexylmethyl-4-morpholin-4-yl-4-oxo-butyramide;

N-[(3S)-3-Cyano-1-trans-(4-isopropyl-cyclohexyl)-pyrrolidin-3-yl]-(2R)-2-cyclohexylmethyl-4-morpholin-4-yl-4-oxo-butyramide;

N-[(3R)-3-Cyano-1-trans-(4-isopropyl-cyclohexyl)-pyrrolidin-3-yl]-(2R)-2-cyclohexylmethyl-4-morpholin-4-yl-4-oxo-butyramide;

N-[(3S)-3-Cyano-1-cis-(4-isopropyl-cyclohexyl)-pyrrolidin-3-yl]-(2R)-2-cyclohexylmethyl-4-morpholin-4-yl-4-oxo-butyramide;

N-[(3R)-3-Cyano-1-cis-(4-isopropyl-cyclohexyl)-pyrrolidin-3-yl]-(2R)-2-cyclohexylmethyl-4-morpholin-4yl-4-oxo-butyramide;

N-[1-trans-(4-tert-Butyl-cyclohexyl)-(3S)-3-cyano-pyrrolidin-3-yl]-(2R)-2-cyclohexylmethyl-4-morpholin-4-yl-4-oxo-butyramide;

N-[1-trans-(4-tert-Butyl-cyclohexyl)-(3R)-3-cyano-pyrrolidin-3-yl]-(2R)-2-cyclohexylmethyl-4-mozpholin-4-yl-4-oxo-butyramide;

N-[1-cis-(4-tert-Butyl-cyclohexyl)-(3S)-3-cyano-pyrrolidin-3-yl]-(2R)-2-cyclohexylmethyl-4-morpholin-4-yl-4-oxo-butyramide;

N-[1-cis-(4-tert-Butyl-cyclohexyl)-(3R)-3-cyano-pyrrolidin-3-yl]-(2R)-2-cyclohexylmethyl-4-morpholin-4-yl-4-oxo-butyramide;

N-[(3S)-3-cyano-1-cis-(3-methyl-cyclohexyl)-pyrrolidin-3-yl]-(2R)-2-cyclohexylmethyl-4-morbolin-4-yl-4-oxo-butyramide;

N-[(3R)-3-cyano-1-cis-(3-methyl-cyclohexyl)-pyrrolidin-3-yl]-(2R)-2-cyclohexylmethyl-4-morpholin-4-yl-4-oxo-butyramide;

N-[(3S)-3-cyano-1-trans-(3-methyl-cyclohexyl)-pyrrolidin-3-yl]-(2R)-2-cyclohexylmethyl-4-morpholin-4-yl-1-oxo-butyramide;

N-[(3R)-3-cyano-1-trans-(3-methyl-cyclohexyl)-pyrrolidin-3-yl]-(2R)-2-cyclohexylmethyl-4-morpholin-4-yl-4-oxo-butyramide;

N-[(3S)-3-Cyano-1-(3,3-dimethyl-cyclohexyl)-pyrrolidin-3-yl]-(2R)-2-cyclohexylmethyl-4-morpholin-4-yl-4-oxo-butyramide;

N-[(3R)-3-Cyano-1-(3,3-dimethyl-cyclohexyl)pyrrolidin-3-yl]-(2R)-2-cyclohexylmetbyl-4-morpbolin-4yl-4-oxo-butyramide;

N-[(3S)-3-Cyano-1-cis-(3-isopropyl-cyclohexyl)-pyrrolidin-3-yl]-(2R)-2-cyclohexylmethyl-4-morpholin-4-yl-4-oxo-butyramide;

N-[(3R)-3-Cyano-1-cis-(3-isopropyl-cyclohexyl)-pyrrolidin-3-yl]-(2R)-2-cyclohexylmethyl-4-morpholin-4-yl-4-oxo-butyramide;

N-[(3S)-3-Cyano-1-trans-(3-isopropyl-cyclohexyl)-pyrrolidin-3-yl]-(2R)-2-cyclohexylmethyl-4-morpholin-4-yl-4-oxo-butyramide;

N-[(3R)-3-Cyano-1-trans-(3-isopropyl-cyclohexyl)-pyrrolidin-3-yl]-(2R)-2-cyclohexylmethyl-4-morpholin-4-yl-4-oxo-butyramide;

N-[(3S)-3-Cyano-1-cis-(2-methyl-cyclohexyl)-pyrroidin-3-yl]-(2R)-2-cyclohexylmethyl-4-morpholin-4-yl-4-oxo-butyramide;

N-[(3R)-3-Cyano-1-cis-(2-methyl-cyclohexyl)-pyrrolidin-3-yl]-(2R)-2-cyclohexylmetbyl-4-morpholin-4-yl-4-oxo-butyramide;

N-[(3S)-3-Cyano-1-trans-(2-methyl-cyclohexyl)-pyrrolidin-3-yl]-(2R)-2-cyclohexylmethyl-4-morpholin-4yl-4-oxo-butyramide;

N-[(3R)-3-Cyano-1-trans-(2-methyl-cyclohexyl)-pyrrolidin-3-yl]-(2R)-2-cyclohexylmethyl-4-morpholin-4-yl-4-oxo-butyramide;

N-[(3S)-3-Cyano-1-cis-(2-ethyl-cyclohexyl)-pyrrolidin-3-yl]-(2R)-2-cyclohexylmethyl-4-morpholin-4-yl-4-oxo-butyramide;

N-[(3R)-3-Cyano-1-cis-(2-ethyl-cyclohexyl)-pyrrolidin-3-yl]-(2R)-2-cyclohexylmethyl-4-morpholin-4-yl-4-oxo-butyramide;

N-[(3S)-3-Cyano-1-trans-(2-ethyl-cyclohexyl)-pyrrolidin-3-yl]-(2R)-2-cyclohexylmethyl-4-morpholin-4-yl-4-oxo-butyramide;

N-[(3R)-3-Cyano-1-trans-(2-ethyl-cyclohexyl)-pyrrolidin-3-yl]-(2R)-2-cyclohexylmethyl-4-morpholin-4-yl-4-oxo-butyramide;

N-[(3S)-3-Cyano-1-(2,2-dimethyl-cyclohexyl)-pyrrolidin-3-yl]-(2R)-2-cyclohexylmethyl-4-morpholin-4-yl-4-oxo-butyramide;

N-[(3R)-3-Cyano-1-(2,2-dimethyl-cyclohexyl)-pyrrolidin-3-yl]-(2R)-2-cyclohexylmethyl-4-morpholin-4-yl-4-oxo-butyramide;

N-[(3S)-3-Cyano-1-(4,4-dimethyl-cyclohexyl)-pyrrolidin-3-yl]-(2R)-2-cyclohexylmethyl-4-morpholin-4-yl-4-oxo-butyramide;

N-[(3R)-3-Cyano-1-(4,4-dimethyl-cyclohexyl)-pyrrolidin-3-yl]-(2R)-2-cyclohexylmethyl-4-morpholin-4-yl-4-oxo-butyramide;

N-[(3S)-3-Cyano-1-(2-methyl-2-phenyl-propyl)-pyrrolidin-3-yl]-(2R)-2-cyclohexylmethyl-4-morpholin-4-yl-4-oxo-butyramide;

N-[(3R)-3-Cyano-1-(2-methyl-2-phenyl-propyl)-pyrrolidin-3-yl]-(2R)-2-cyclohexylmethyl-4-morpholin-4-yl-4-oxo-butyramide;

N-[(3S)-3-Cyano-1-indan-2-ylmethyl-pyrrolidin-3-yl]-(2R)-2-cyclohexylmethyl-4-morpholin-4-yl-4-oxo-butyramide;

N-[(3R)-3-Cyano-1-indan-2-ylmethyl-pyrrolidin-3-yl]-(2R)-2-cyclohexylmethyl-4-morpholin-4-yl-4-oxo-butyramide;

N-[(3S)-3-Cyano-1-(5-methyl-thiophen-2-ylmethyl)-pyrrolidin-3-yl]-(2S)-2-cyclohexylmethyl-4-morpholin-4-yl-4-oxo-butyramide;

N-[(3S)-3-Cyano-1-(5-methyl-thiophen-2-ylmethyl)-pyrrolidin-3-yl]-(2S)-2-cyclohexylmethyl-4-morpholin-4-yl-4-oxo-butyramide;

N-[(3S)-3-Cyano-pyrrolidin-3-yl]-(2R)-2-cyclohexylmethyl-4-morpholin-4-yl-4-oxo-butyramide and N-[(3R)-3-Cyano-pyrrolidin-3-yl]-(2R)-2-cyclohexylmethyl-4-morpholin-4-yl-4-oxo-butyramide.

Of the above-listed preferred compounds, the following are more preferred compounds of the invention:

N-(Benzyloxymethyl-cyano-methyl)-2-cyclohexylmethyl-4-morpholin-4-yl-4-oxo-butyramide;

N-[2-(4-Chloro-benzyloxy)-1-cyano-ethyl]-2-cyclohexylmethyl-4-morpholin-4-yl-4-oxo-butyramide. MS: m/z=477 M+1;

N-(cyano-1-benzyl-pyrrolidin-3-ylcarbanoyl)-2-cyclohexylmethyl-4-morpholin-4-yl-4-oxo-butyramide;

N-(3-Cyano-1-cyclohexylmethyl-pyrrolidin-3-yl)-2-cyclohexylmethyl-4-morpholin-4-yl-4-oxo-butyramide. MS: m/z=473 M+1;

N-[3-Cyano-1-(2,6-difluoro-benzyl)-pyrrolidin-3-yl]-2-cyclohexylmethyl-4-morpholin-4-yl-4-oxo-butyramide. MS: m/z=503 M+1;

N-[3-Cyano-1-(3,5-difluoro-benzyl)-pyrrolidin-3-yl]-2-cyclohexylmethyl-4-morpholin-4-yl-4-oxo-butyramide. MS: m/z=503 M+1;

N-[3-Cyano-1-(3-trifluoromethyl-benzyl)-pyrrolidin-3-yl-2-cyclohexylmethyl-4-morpholin-4-yl-4-oxo-butyramide. MS: m/z=535 M+1;

N-(3-Cyano-1-cyclohexyl-pyrrolidin-3-yl)-2-cyclohexylmethyl-4-morpholin-4-yl-4-oxo-butyramide. MS: m/z=459 M+1;

N-(3-cyano-1-(3,3-dimethyl-butyl)-pyrrolidin-3-ylcarbamoyl)-2-cyclohexylmethyl-4-morpholin-4-yl-4-oxo-butyramide;

N-(3-Cyano-1-isopropyl-pyrrolidin-3-yl)-2-cyclohexylmetbyl-4-morpholin-4-yl-4-oxo-butyramide. MS: m/z=419 M+1;

N-(3-Cyano-1-isobutyl-pyrrolidin-3-yl)-2-cyclohexylmethyl-4-morpholin-4-yl-4-oxo-butyramide. MS: m/z=433 M+1;

N-(3-Cyano-1-cyclopropylmethyl-pyrrolidin-3-yl)-2-cyclohexylmethyl-4-morpholin-4-yl-4-oxo-butyramide. MS: m/z=431 M+1;

N-(3-Cyano-1-phenethyl-pyrrolidin-3-yl)-2-cyclohexyhmethyl-4-morpholin-4-yl-4-oxo-butyramide. MS: m/z=481 M+1;

N-(3-Cyano-1-methyl-piperidin-3-yl)-2-cyclohexylmethyl-4-morpholin-4-yl-4-oxo-butyramide. MS: m/z=405 M+1;

N-[3-Cyano-1-(4-methyl-cyclohexyl)-pyrrolidin-3-yl]-2-cyclohexylmethyl-4-morpholin-4-yl-4-oxo-butyramide. MS: m/z=473 M+1;

N-(3-Cyano-1-propyl-pyrrolidin-3-yl)-2-cyclohexylmethyl-4-morpholin-4-yl-4-oxo-butyramide. MS: m/z=419 M+1;

N-(3-Cyano-1-cyclopentyl-pyrrolidin-3-yl)-2-cyclohexylmethyl-4-morpholin-4-yl-4-oxo-butyramide. MS: m/z=445 M+1;

N-[3-Cyano-1-(1H-indol-2-ylmethyl)-pyrrolidin-3-yl]-2-cyclohexylmethyl-4-morpholin-4-yl-4-oxo-butyramide;

N-(3-Cyano-1-cycloheptyl-pyrrolidin-3-yl)-2-cyclohexylmethyl-4-morpholin-4-yl-4-oxo-butyramide. MS: m/z=473 M+1;

N-[3-Cyano-1-(1,2,3,4-tetrahydro-naphthalen-1-yl)-pyrrolidin-3-yl]-2-cyclohexylmethyl-4-morpholin-4-yl-4-oxo-butyramide. MS: m/z=507 M+1;

N-(1-Bicyclo[2.2.1]hept-2-yl-3-cyano-pyrrolidin-3-yl)-2-cyclohexylmethyl-4-morpholin-4-yl-4-oxo-butyramide. MS: m/z=471 M+1;

N-[3-Cyano-1-(tetrahydro-pyran-4-yl)-pyrrolidin-3-yl]-2-cyclohexylmethyl-4-morpholin-4-yl-4-oxo-butyramide, MS: m/z 461=M+1;

N-[3-Cyano-1-(tetrahydro-thiopyran-4-yl)-pyrrolidin-3-yl]-2-cyclohexylmethyl-4-morpholin-4-yl-4-oxo-butyramide, MS: m/z 477=M+1;

N-[3-Cyano-1-(tetrabydro-thiopyran-4-yl)-pyrrolidin-3-yl]-2-cyclohexylmethyl-4-morpholin-4-yl-4-oxo-butyramide, MS: m/z 477=M+1;

(4R)-N-(3-Cyano-1-cyclohexyl-pyrrolidin-3-yl)-2-(4-methyl-cyclohexylmethyl)-4-morpholin-4-yl-4-oxo-butyramide;

2-Bicyclo[4.1.0]hept-7-ylmethyl-N-(3-cyano-1-cyclohexyl-pyrrolidin-3-yl)-4-morpholin-4-yl-4-oxo-butyramide;

N-(3-Cyano-1-cyclohexyl-pyrrolidin-3-yl)-4-morpholin-4-yl-4-oxo-2-(1,2,3,4-tetrahydro-naphthalen-2-ylmethyl)-butyramide; MS, m/z 507=M+1;

N-(3-Cyano-1-cyclohexyl-pyrrolidin-3-yl)-2-indan-2-ylmethyl-4-morpholin-4-yl-4-oxo-butyramide; MS, m/z 493=M+1;

N-(3-Cyano-1-cyclohexyl-pyrrolidin-3-yl)-2-cyclopentylmethyl-4-morpholin-4-yl-4-oxo-butyramide; MS, m/z 445=M+1;

N-{Cyano-[(cyclohexyl-ethyl-amino)-methyl]-methyl}-2-cyclohexylmethyl-4-morpholin-4-yl-4-oxo-butyramide;

N-(Cyano-piperidin-1-ylmethyl-methyl)-2-cyclohexylmethyl-4-morpholin-4-yl-4-oxo-butramide;

N-[(3S)-3-Cyano-1-trans-(4-ethyl-cyclohexyl)-pyrrolidin-3-yl]-(2R)-2-cyclohexylmethyl-4-morpholin-4-yl-4-oxo-butyramide;

N-[(3S)-3-Cyano-1-cis-(4-ethyl-cyclohexyl)-pyrrolidin-3-yl]-(2R)-2-cyclohexylmethyl-4-morpholin-4-yl-4-oxo-butyramide;

N-[(3S)-3-Cyano-1-trans-(4-isopropyl-cyclohexyl)-pyrrolidin-3-yl]-(2R)-2-cyclohexylmethyl-4-morpholin-4-yl-4-oxo-butyramide;

N-[(3S)-3-Cyano-1-cis-(4-isopropyl-cyclohexyl)-pyrrolidin-3-yl]-(2R)-2-cyclohexylmethyl-4-morpholin-4-yl-4-oxo-butyramide;

N-[1-trans-(4-tert-Butyl-cyclohexyl)-(3S)-3-cyano-pyrrolidin-3-yl]-(2R)-2-cyclohexylmethyl-4-morpholin-4-yl-4-oxo-butyramide;

N-[(3S)-3-cyano-1-cis-(3-methyl-cyclohexyl)-pyrrolidin-3-yl]-(2R)-2-cyclohexylmethyl-4-morpholin-4-yl-4-oxo-butyramide;

N-[(3S)-3-cyano-1-trans-(3-methyl-cyclohexyl)-pyrrolidin-3-yl]-(2R)-2-cyclohexylmethyl-4-morpholin-4-yl-4-oxo-butyramide;

N-[(3R)-3-cyano-1-trans-(3-methyl-cyclohexyl)-pyrrolidin-3-yl]-(2R)-2-cyclohexylmethyl-4-morpholin-4-yl-4-oxo-butyramide;

N-[(3S)-3-Cyano-1-(3,3-methyl-cyclohexyl)-pyrrolidin-3-yl]-(2R)-2-cyclohexylmethyl-4-morpholin-4-yl-4-oxo-butyramide;

N-[(3R)-3-Cyano-1-(3,3-dimethyl-cyclohexyl)-pyrrolidin-3-yl]-(2R)-2-cyclohexylmethyl-4-morpholin-4-yl-4-oxo-butyramide;

N-[(3S)-3-Cyano-1-cis-(3-isopropyl-cyclohexyl)-pyrrolidin-3-yl]-(2R)-2-cyclohexylmethyl-4-morpholin-4-yl-4-oxo-butyramide;

N-[(3S)-3-Cyano-1-trans-(3-isopropyl-cyclohexyl)-pyrrolidin-3-yl]-(2R)-2-cyclohexylmethyl-4-morpholin-4yl-4-oxo-butyramide;

N-[(3R)-3-Cyano-1-trans-(3-isopropyl-cyclohexyl)-pyrrolidin-3-yl]-(2R)-2-cyclohexylmethyl-4-morpholin-4-yl-4-oxo-butyramide;

N-[(3S)-3-Cyano-1-cis-(2-methyl-cyclohexyl)-pyrrolidin-3-yl]-(2R)-2-cyclohexylmethyl-4-morpholin-4-yl-4-oxo-butyramide;

N-[(3S)-3-Cyano-1-trans-(2-methyl-cyclohexyl)-pyrrolidin-3-yl]-(2R)-2-cyclohexylmethyl-4-morpholin-4-yl-4-oxo-butyramide;

N-[(3S)-3-Cyano-1-cis-(2-ethyl-cyclohexyl)-pyrrolidin-3-yl]-(2R)-2-cyclohexylmethyl-4-morpholin-4-yl-4-oxo-butyramide;

N-[(3S)-3-Cyano-1-trans-(2-ethyl-cyclohexyl)-pyrrolidin-3-yl]-(2R)-2-cyclohexylmethyl-4-morpholin-4-yl-4-oxo-butyramide;

N-[(3S)-3-Cyano-1-(2,2-dimethyl-cyclohexyl)-pyrrolidin-3-yl]-(2R)-2-cyclohexylmethyl-4-morpholin-4-yl-4-oxo-butyramide;

N-[(3S)-3-Cyano-1-(4,4-dimethyl-cyclohexyl)-pyrrolidin-3-yl]-(2R)-2-cyclohexylmethyl-4-morpholin-4-yl-4-oxo-butyramide;

N-[(3S)-3-Cyano-1-(2-methyl-2-phenyl-propyl)-pyrrolidin-3-yl]-(2R)-2-cyclohexylmethyl-4-morpholin-4-yl-4-oxo-butyramide;

N-[(3R)-3-Cyano-1-(2-methyl-2-phenyl-propyl)-pyrrolidin-3-yl]-(2R)-2-cyclohexylmethyl-4-morpholin-4-yl-4-oxo-butyramide;

N-[(3S)-3-Cyano-1-indan-2-ylmethyl-pyrrolidin-3-yl]-(2R)-2-cyclohexylmethyl-4-morpholin-4-yl-4-oxo-butyramide and N-[(3S)-3-Cyano-1-(5-methyl-thiophen-2-ylmethyl)-pyrrolidin-3-yl]-(2S)-2-cyclohexylmethyl-4-morpholin-4-yl-4-oxo-butyramide.

Of the above-listed more preferred compounds, the following are most preferred compounds of the invention:

N-(cyano-1-benzyl-pyrrolidin-3-ylcarbamoyl)-2-cyclohexylmethyl-4-morpholin-4-yl-4-oxo-butyramide;

N-(3-Cyano-1-cyclohexyl-pyrrolidin-3-yl)-2-cyclohexylmethyl-4-morpholin-4-yl-4-oxo-butyramide. MS: m/z=459 M+1;

N-(3-Cyano-1-cyclopropylmethyl-pyrrolidin-3-yl)-2-cyclohexylmethyl-4-morpholin-4-yl-4-oxo-butyramide. MS: m/z=431 M+1;

N-(3-Cyano-1-phenethyl-pyrrolidin-3-yl)-2-cyclohexylmethyl-4-morpholin-4-yl-4-oxo-butyramide. MS: m/z=481 M+1;

N-[3-Cyano-1-(4-methyl-cyclohexyl)-pyrrolidin-3-yl]-2-cyclohexylmethyl-4-morpholin-4-yl-4-oxo-butyramide. MS: m/z=473 M+1;

(4R)-N-(3-Cyano-1-cyclohexyl-pyrrolidin-3-yl)-2-(4-methyl-cyclohexylmethyl)-4-morpholin-4-yl-4-oxo-butyramide;

N-(3-Cyano-1-cyclohexyl-pyrrolidin-3-yl)-4-morpholin-4-yl-4-oxo-2-(1,2,3,4-tetrahydro-naphthalen-2-ylmethyl)-butyramide; MS, m/z 507=M+1;

N-[(3S)-3-Cyano-1-trans-(4-ethyl-cyclohexyl)-pyrrolidin-3-yl]-(2R)-2-cyclohexylmethyl-4-morpholin-4-yl-4-oxo-butyramide;

N-[(3S)-3-cyano-1-trans-(3-methyl-cyclohexyl)-pyrrolidin-3-yl]-(2R)-2-cyclohexylmethyl-4-morpholin-4-yl-4-oxo-butyramide;

N-[(3R)-3-cyano-1-trans-(3-methyl-cyclohexyl)-pyrrolidin-3-yl]-(2R)-2-cyclohexylmethyl-4-morpholin-4-yl-4-oxo-butyramide and N-[(3S)-3-Cyano-1-(3,3-dimethyl-cyclohexyl)-pyrrolidin-3-yl]-(2R)-2-cyclohexylmethyl-4-morpholin-4-yl-4-oxo-butyramide.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formulas (I) and (Ia) can exist in more than one tautomeric form. The invention includes all such tautomers.

It shall be understood by one of ordinary skill in the art that all compounds of the invention are those which are chemically stable.

The invention includes pharmaceutically acceptable derivatives of compounds of formulas (I) and (Ia). A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof.

In addition, the compounds of this invention include prodrugs of compounds of the formulas (I) and (Ia). Prodrugs include those compounds that, upon simple chemical transformation, are modified to produce the compounds of the invention. Simple chemical transformations include hydrolysis, oxidation and reduction. Specifically, when a prodrug of this invention is administered to a patient, the prodrug may be transformed into a compound of formula (I) and (Ia), thereby imparting the desired pharmacological effect.

In order that the invention herein described may be more fully understood, the following detailed description is set forth. As used herein, the following abbreviations are used:

BOC or t-BOC is tertiary butoxycarbonyl t-Bu is tertiary butyl

DMF is dimethylformamide

EtOAc is ethyl acetate

THF is tetrahydrofuran

Ar is argon

EDC is 1-(3-dimethylaminopropyl)-3-ethylcarbodiimide hydrochloride

HOBT is 1-hydroxybenzotriazole.

Also, as used herein, each of the following terms, used alone or in conjunction with other terms, are defined as follows (except where noted to the contrary):

The term "alkyl" refers to a saturated aliphatic radical containing from one to ten carbon atoms or a mono- or polyunsaturated aliphatic hydrocarbon radical containing from two to twelve carbon atoms, containing at least one double or triple bond, respectively. "Alkyl" refers to both branched and unbranched alkyl groups. Preferred alkyl groups are straight chain alkyl groups containing from one to eight carbon atoms and branched alkyl groups containing from three to eight carbon atoms. More preferred alkyl groups are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl refers to an alkyl group linked to a carbonyl group (C=O).

The term "cycloalkyl" refers to the cyclic analog of an alkyl group, as defined above, optionally unsaturated and substituted. Preferred cycloalkyl groups are saturated cycloalkyl groups containing from three to eight carbon atoms, and more preferably three to six carbon atoms.

The term "aryl" refers to phenyl and naphthyl.

Each of the above defined "alkyl", "cycloalkyl" and "aryl" shall be understood to include their halogenated analogs.

The term "halo" refers to a halogen radical selected from fluoro, chloro, bromo or iodo. Preferred halo groups are fluoro, chloro and bromo.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms selected from the group consisting of nitrogen, oxygen and sulfur. The heterocycle may be attached by any atom of the cycle, which results in the creation of a stable structure. Preferred heteroaryl radicals include, for example, furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl or phenoxazinyl, The term "heterocycle" refers to a stable 5–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms selected from the group consisting of nitrogen, oxygen and sulfur. The heterocycle may be attached by any atom of the cycle, which results in the creation of a stable structure. Preferred heterocycle radicals include, for example, pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4dione.

The terms "heterocycle", "heteroaryl" or "aryl", when associated with another moiety, unless otherwise specified shall have the same meaning as given above. For example, "aroyl" refers to phenyl or naphthyl linked to a carbonyl group (C=O).

Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

As used herein above and throughout this application, "nitrogen" and "sulfur" include any oxidized form of nitrogen and sulfur and the quaternized form of any basic nitrogen. In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds. Starting materials used in the scheme below are either commercially available or easily prepared from commercially available materials by those skilled in the art.

General Synthetic Methods

The invention also provides processes of making the present novel compounds. Compounds of the invention may be prepared by methods described below. Standard peptide coupling, protection and deprotection reactions (see for example M. Bodanszky, The Practice of Peptide Synthesis, Springer-Verlag, 1984) are employed in these syntheses. Alkylated succinic acid derivatives used as starting materials are either commercially available or easily prepared by methods known to those skilled in the art. For example succinate derivatives may be alkylated by treatment with a suitable alkylating agent such as an alkyl halide in the presence of a suitable base such as lithium diisopropyl amide. If the succinate derivative contains a chiral auxiliary, for example a succinic acid chiral oxazolidine amide, a chiral allylated succinate derivative can be obtained as described by Azam et al. (J. Chem. Soc. Perkin Trans. 1, 1996, 621) and Evans et al. (J. Am. Chem. Soc., 1981, 103, 2127). Alternatively, racemic alkylated succinate derivatives may be resolved by methods known to those skilled in the art if desired, for example by selective enzymatic hydrolysis as described by Oikawa et al. (Tetrahedron Lett., 1996, 37, 6169), Wirz et al. (Tetrahedron Asymmetry, 1997, 8, 187) and Ozaki et al. (Chem. Lett., 1997, 741).

Compounds of the invention in which $R_1$ is an amino group or a heterocyclyl group containing a nitrogen that forms an amide bond with A (A=—C(O)—) of formula I may be prepared as described below and illustrated in Scheme I.

Scheme I

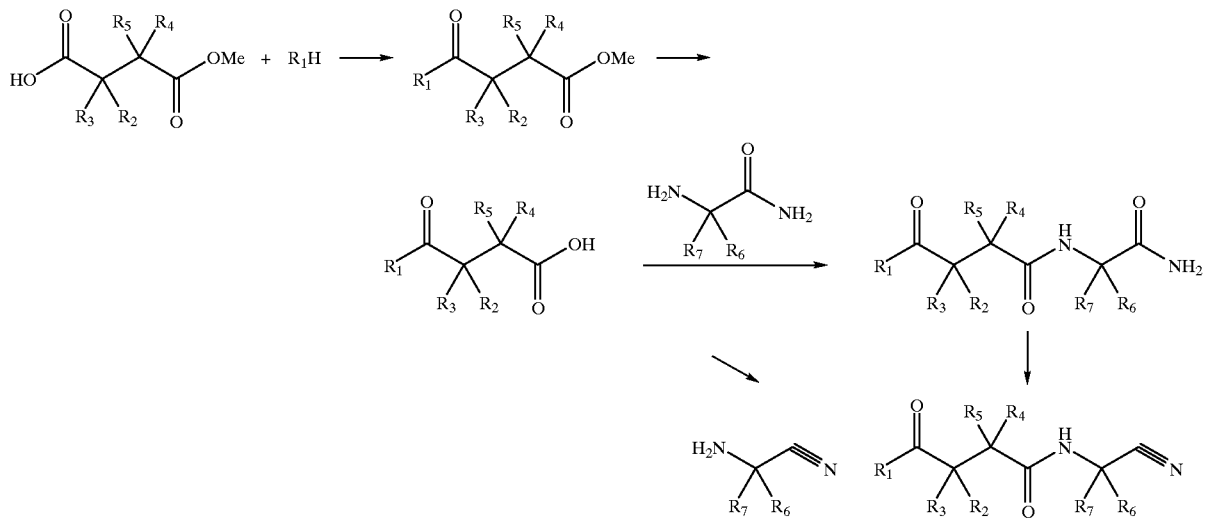

A succinic acid monoester, for example a methyl ester as shown, is reacted with the desired amine $R_1H$ under standard peptide coupling conditions. An example of standard coupling conditions would be combining the starting materials in the presence of a coupling reagent such as 1-(3-dimethylaminopropyl)-3-ethylcarbodiimide (EDC) with 1-hydroxybenzotriazole (HOBT), in a suitable solvent such as DMF or methylene chloride. A base such as N-methylmorpholine may be added. The resulting amide ester is hydrolyzed in aqueous base or acid. A suitable co-solvent such as THF or MeOH may be added. The resulting acid is then coupled with an amino nitrile under standard peptide coupling conditions as described above to provide the desired compound of formula (I).

Alternately, one may couple the acid with an amino amide and then react the resulting amide with a suitable dehydrating agent such as cyanuric chloride in a suitable solvent such as DMF to provide the desired nitrile of formula (I).

Compounds of the invention in which $R_1$ is alkyl or cycloalkyl may be prepared by reacting a succinic acid ester derivative, for example a methyl ester as shown below, containing an activated amide, for example a N-methoxy-N-methylamide (Solladic-Cavallo et al., Tetrahedron Asymmetry, 1996, 7, 1797), or a N-imidazolium-N-methylamide (De Las Heras et al., Tetrahedron Lett., 1997, 38, 1817) with a suitable organometallic reagent, such as an alkylmagnesium bromide (Scheme II). The resulting ketoester is then carried forth as described for the amide ester intermediate in Scheme I.

Scheme II

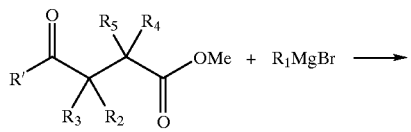

-continued

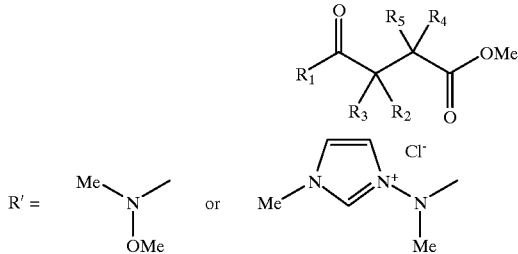

Compounds of the invention in which R1 is aryl or heteroaryl may be prepared by reacting a suitable aryl or heteroaryl organometallic reagent with an activated amide as described above for $R_1$=alkyl or cycloalkyl. In addition, an acyl halide, for example an acid chloride, may be used in place of an activated amide. Suitable aryl or heteroaryl organometallic reagents for reaction with acyl halides are known in the art and include aryl magnesium bromides (F. Babudri et al., Tetrahedron, 1996, 52, 13513), aryl lithium reagents in the presence of $ZnCl_2$ (C. Kim et al., Tetrahedron Lett., 1994, 35, 3017) and aryl stannanes under Pd catalyzed Stille coupling conditions (M. J. Plunkett et al., J. Am. Chem. Soc., 1995, 117, 3306).

A method which may be used to stereoselectively prepare alkylated succinic acid derivatives, useful in the procedures described in Schemes I and II, is illustrated in Scheme III.

Scheme III

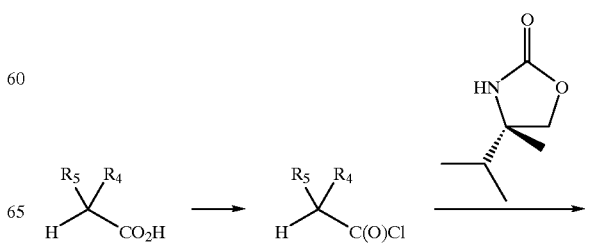

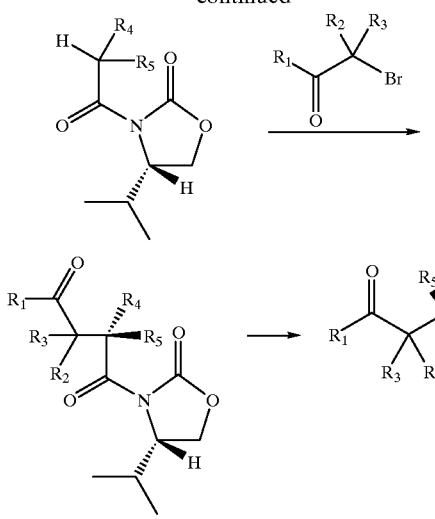

In this procedure, a carboxylic acid bearing $R_4$ and $R_5$ is coupled with a chiral auxiliary group known in the art (see for example D. Evans et al., J. Am. Chem. Soc., 1990, 4011; D. Evans et al., J. Am. Chem. Soc., 1981, 2127, 103; D. Evans et al., Tetrahedron Lett, 1987, 6141; D. Evans et al., Tetrahedron Lett, 1987, 1123), such as (S)-(−)-4-isopropyl-2-oxazolidinone as illustrated in Scheme III. Suitable coupling conditions would include first converting the carboxylic acid to an acid chloride, for example by reaction with oxalyl chloride and DMF in a suitable solvent such as methylene chloride at about 0° C. to room temperature. The acid chloride may then be coupled to the oxazolidinone in a suitable solvent, such as THF, in the presence of a suitable base, such as n-BuLi at about −78° C. to room temperature.

The resulting product is then alkylated with a halomethylcarbonyl compound bearing $R_1$, $R_2$ and $R_3$ in a suitable solvent such as THF, in the presence of a suitable base, such as sodium bis(trimethylsilyl)amide at about −78° C. to room temperature. The large group on the chiral auxiliary (the isopropyl group in the illustrated example) directs the alkylating group to the side opposite it providing predominantly one isomer at the alkylated carbon. The chiral auxiliary is then removed by methods known in the art, for example in the case illustrated, in a suitable solvent such as THF in the presence of water and a suitable peroxide such as 30% hydrogen peroxide at about 0° C., providing the desired succinic acid derivative which may be used in the procedure outlined in Scheme I, or converted to the corresponding ester by methods known to those skilled in the art and used in the procedure outlined in Scheme II.

Compounds of the invention in which $R_1$ is alkyl, cycloalkyl, aryl or heteroaryl and A is —C(O)— may be reacted with a suitable reducing agent such as sodium borohydride to produce the corresponding compound where A is —C(OH)—.

The synthetic examples below are illustrative of the methods used to prepare the compounds of the invention.

SYNTHETIC EXAMPLES

Example 1

N-(Benzyloxymethyl-cyano-methyl)-2Cyclohexylmethyl-4-morpholin-4-yl-4-oxo-butyramide

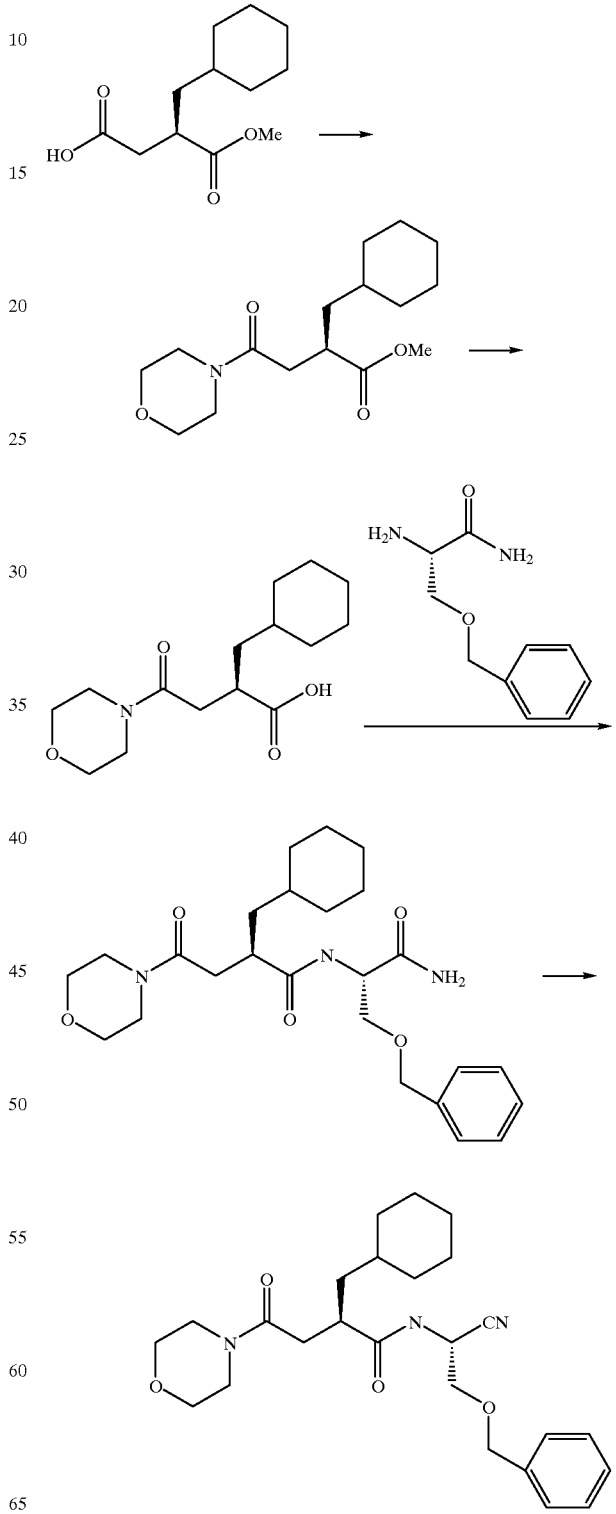

(a) (R)-2-Cyclohexylmethyl-4-morpholin-4-yl-4-oxo-butyric acid 1-methyl ester (R)-2-(Cyclohexylmethyl)succinic acid 1-methyl ester (1.00 g, 4.38 mmol) was dissolved in 10 mL of DMF and cooled to 0° C. with an ice-water bath. EDC (1.12 g, 5.69 mmol) then 1-hydroxybenzotriazole (0.77 g, 5.69 mmol) were added and stirring continued, under argon, for 25 min. Morpholine (0.76 mL, 8.76 mmol) was added and stirring was continued overnight (16 h). The solution was diluted with 200 mL of EtOAc and washed with a 1.0 M solution of HCl (3×100 mL), a saturated solution of NaHCO$_3$ (3×100 mL), water (100 mL), then with brine (100 mL). The organic layer was dried over MgSO$_4$, filtered and concentrated by rotary evaporation to give (R)-2-Cyclohexylmethyl-4-morpholin-4-yl-4-oxo-butyric acid 1-methyl ester (1.26 g, 99%) as a white solid. The product was used in the following step without purification.

(b) (R)-2-Cyclohexylmethyl-4-morpholin-4-yl-4-oxo-butyric acid

The ester from the above step (1.21 g, 4.06 mmol) was dissolved in THF (55 mL) and MeOH (27 mL) was then added. This solution was cooled to 0° C. with an ice-water bath, then a solution of LiOH.H$_2$O (0.51 g, 12.18 mmol) in H$_2$O (27 mL) was slowly added and the mixture was allowed to stir for 5 hr at room temperature. The mixture was poured into water (100 mL) and extracted with Et$_2$O (2×50 mL). The aqueous layer was acidified with 1.0 N HCl, then extracted with EtOAc (3×50 mL). The combined organic layers were then washed with H$_2$O (2×50 mL) followed by brine (2×50 mL), dried over Na$_2$SO$_4$, filtered and the solvent was evaporated to afford (R)-2-Cyclohexylmethyl-4-morpholin-4-yl-4-oxo-butyric acid (0.88 g, 76%) as a clean white solid that was used without further purification.

(c) N-(t-butoxycarbonyl)-L-(O-benzyl)serinamide

NH$_4$OH (10 mL) was added to a premixed (15 min) solution of N-(t-butoxycarbonyl)-L-(O-benzyl)serine (10.0 g, 33.9 mmol), EDC (7.80 g, 40.7 mmol), and HOBT (5.50 g, 40.7 mmol) in DMF (120 mL) at room temperature. After 16 h the reaction mixture was diluted with CH$_2$Cl$_2$ and filtered, washed sequentially with 10% aq. HCl, satd. NaHCO$_3$, H$_2$O (×3), brine, then dried over Na$_2$SO$_4$, and concentrated giving N-(t-butoxycarbonyl)-L-(O-benzyl) serinamide (11.5 g) as a white solid.

(d) L-(O-Benzyl)Serine amide HCl

N-(t-butoxycarbonyl)-L-(O-benzyl)serinamide (1.00 g) was dissolved in anhydrous THF (5 ml) and cooled in an ice/water bath. A 4M solution of HCl in dioxane (5 ml) was added and the reaction stirred for two h and then concentrated under reduced pressure to provide a glass which was then triturated with diethyl ether to obtain L-(O-Benzyl) Serine amide HCl as a white solid (0.9 g). This material was used without further purification.

(e) N-(2-Benzyloxy-1-carbamoyl-ethyl)-2-cyclohexylmethyl-4-morpholin-4-yl-oxo-butyramide (R)-2-Cyclohexylmethyl-4-morpholin-4-yl-4-oxo-butyric acid (0.20 g, 0.71 mmol) was dissolved in 6 mL of DMF and cooled to 0° C. with an ice-water bath. EDC (0.18 g, 0.92 mmol) and 1-hydroxybenzotriazole (0.12 g, 0.92 mmol) were added and stirring, under argon, continued for 25 min. To the cold solution was added the HCl salt of O-benzyl-L-serineamide (0.16 g, 0.71 mmol), followed by addition of N-methylmorpholine (0.23 mL, 2.10 mmol) and stirring was continued overnight (16 h). The solution was diluted with 100 mL of EtOAc and washed with a 1.0 M solution of HCl (3×10 mL), a saturated solution of NaHCO$_3$ (3×10 mL), water (100 mL) then with brine (100 mL). The organic layer was dried over MgSO$_4$, filtered and concentrated by rotary evaporation to give (0.34 g, 106%) of the crude product which was chromatographed (SiO$_2$, 2% MeOH in EtOAc) to give N-(2-Benzyloxy-1-carbamoyl-ethyl)-2-cyclohexylmethyl-4-morpholin-4-yl-oxo-butyramide (0.22 g, 69%).

(f) N-(Benzyloxymethyl-cyano-methyl)-2-cyclohexylmethyl-4-morpholun-4-yl-4-oxo-butyramide N-(2-Benzyloxy-1-carbamoyl-ethyl)-2-cyclohexylmethyl-4-morpholin-4-yl-oxo-butyramide (0.22 g, 0.48 mmol) was dissolved in 4 mL of DMF and cooled to 0° C. with an ice-water bath. To this solution was added cyanuric chloride (0.089 g, 0.48 mmol) and the reaction mixture was stirred for one h. The reaction was quenched with cold water (2 mL), extracted with EtOAc (3×100 mL), and the organic layers were combined and washed with 100 mL brine. The organic layer was dried over MgSO$_4$, filtered and concentrated by rotary evaporation to give the crude residue. The residue was purified by chromatography (SiO$_2$, 35% hexane in EtOAc) to give the title compound as a clear oil (0.12 g, 57%); $^1$H NMR (CDCl$_3$) 7.35 (5H, m), 7.02–7.08 (1H, m), 5.01–5.09 (1H, m), 4.52–4.63 (2H, m), 3.72–3.34 (10H, m), 2.96–2.83 (1H, m), 2.78–2.62 (1H, m), 2.18–2.30 (1H, m), 1.75–1.51 (6H, m), 1.30–1.07 (5H, m), 0.95–0.73 (2H, m). MS: m/z=442 M+1.

Example 2

2-(Morpholine-4-carbonyl)-cyclohexanecarboxylic acid (benzyloxymethyl-cyano-methyl) amide

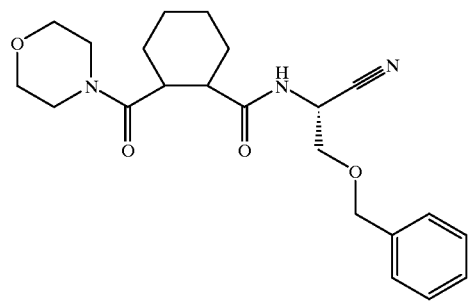

(a) 2-(Morpholine-4-carbonyl)-cyclohexanecarboxylic acid

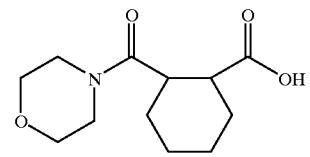

To a solution of cis-1,2-cyclohexane dicarboxylic anhydride (1.0 g, 6.49 mmol) in CH$_2$Cl$_2$ (16 mL) was added morpholine (0.56 g, 6.49 mmol) at 0° C., the resulting mixture was allowed to stir at room temperature overnight (20 h). When complete the reaction mixture was washed with HCl (1.0 N, 20 mL) then with H$_2$O (2×20 mL). The combined aqueous layers were extracted with CH$_2$Cl$_2$ (3×10 mL), and the combined organic layers were dried over MgSO$_4$, the solvent was evaporated in vacuo to give the title compound (1.4 g, 90%/) as a white solid which was used later without further purification.

(b) 2-(Morpholine-4-carbonyl)-cyclohexanecarboxylic acid (2-benzyloxy-1-carbamoyl-ethyl)-amide

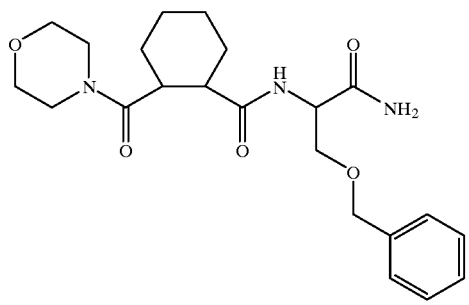

This compound was prepared by the procedure described in Example 1 part e) from 2-(Morpholine-4-carbonyl)-cyclohexanecarboxylic acid and the HCl salt of O-benzyl-L-serineamide to give the crude product which was chromatographed (SiO$_2$, 10% Hexanes in EtOAc) to yield the title compound (1.2 g, 50% yield).

(c) 2-(Morpholine-4-carbonyl)-cyclohexanecarboxylic acid (benzyloxymethyl-cyano-ethyl)-amide

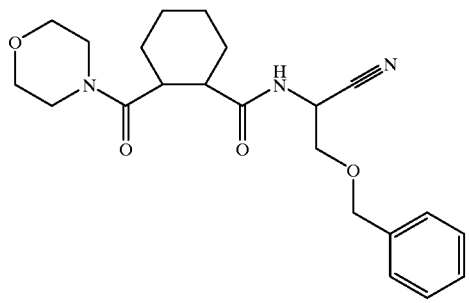

The amide from the step above (0.10 g, 0.24 mmol) and cyanuric chloride (0.044 g, 0.24 mmol) were reacted as described by the procedure in Example 1 part (f). The residue was purified by chromatography (SiO$_2$, 50% Hexanes in EtOAc) to give the title compound as a clear oil (0.055 g, 60%); $^1$H NMR (CDCl$_3$) 7.38–7.1 (6H, m), 5.0 (1H, m), 4.6 (2H, m), 3.75–3.36 (9H, m), 3.3–3.05 (1H, m), 2.55–2.3 (2H, m), 2.0–1.15 (8H, m). MS: m/z=400 M+1.

Example 3

N$^1$-(Benzyloxymethyl-cyano-methyl)-N$^4$-[4-(5-chloro-H-benzoimidazol-2-yl)-phenyl]-2-cyclohexylmethyl-succinamide

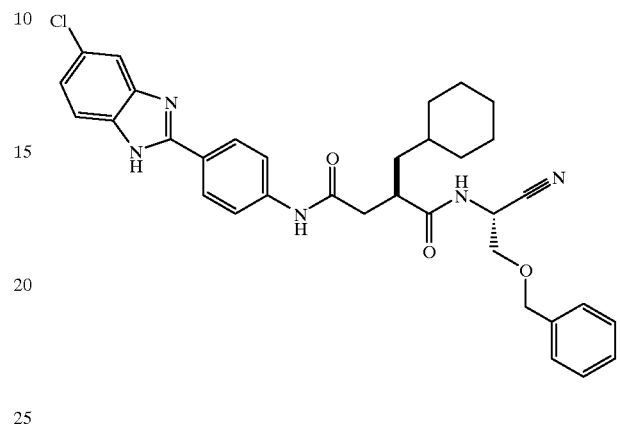

(a) (5-Chloro-2-(4-nitro-phenyl)-1H-benzoimidazole

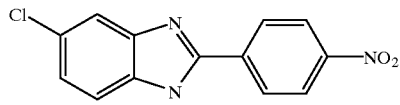

To a solution of 4-Nitrobenzaldehyde (6.4 g, 42.35 nmuol) in THF (300 mL) was added 4-Chloro-1,2-phenylenediamine (4.0 g, 28.05 mmol), and the mixture was stirred under air at room temperature for two days. When complete the reaction mixture was diluted with EtOAc (200 mL), washed with H$_2$O (200 mL) then with HCl (1.0 N, 200 mL). The product precipitated out and was collected by filtration under suction. The solid was washed with EtOAc and allowed to dry. The product was collected as a brownish solid (4.2 g, 55%), pure HCl salt.

(b) 4-(5-Chloro-1H-benzoimidazol-2-yl)-phenylamine

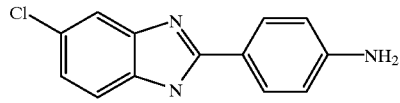

In 500 mL round bottom flask was suspended 5-Chloro-2-(4-nitro-phenyl)-1H-benzoimidazole (4.23 g, 13.66 mmol) in AcOH (30 mL) at 0° C., and to the suspension was added dropwise SnCl$_2$.H$_2$O (9.4 g, 41.66 mmol), in HCl (15 mL). After the addition, the ice bath was removed and the mixture was allowed to stir at room temperature overnight (16 h). The mixture was poured onto ice, and NaOH (50% aq.) was slowly added to pH 12. Then the mixture was extracted with EtOAc (4×150 mL). The combined organic layers were washed with brine, dried over NaSO₄ and filtered, the solvent was evaporated to yield the product as an orange oil. The oil was dissolved in EtOAc and washed with HCl (1.0 N, 100 mL) and the product was isolated as HCl salt (2.13 g, 67%).

(c) N-[4-(5-Chloro-1H-benzoimidazol-2-yl)phenyl]-2-cyclohexylmethyl-succinamic acid

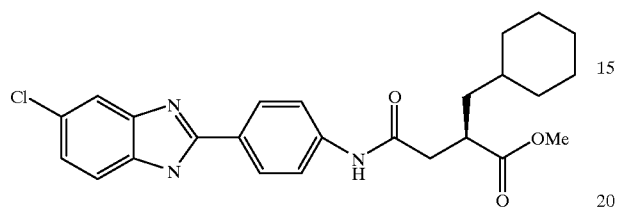

This compound was prepared by the procedure described in Example 1 part (a) from 4-(5-Chloro-1H-benzoimidazol-2-yl) phenylamine and (R)-2-(Cyclohexylmethyl) succinic acid 1-methyl ester to give the crude product (2.0 g, 51%), which was used in the next step without further purification.

(d) N-[4-(5-Chloro-1H-benzolmidazol-2-yl)phenyl]-2-cycohexylmethyl-succinamic acid

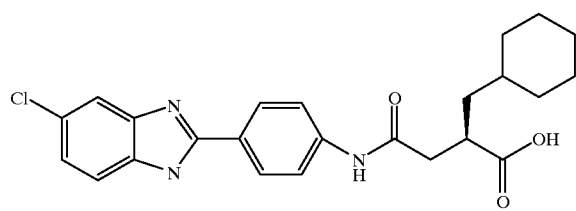

This compound was prepared by the procedure described in Example 1 part (b) from N-[4-(5-Chloro-1H-benzoimidazol-2-yl)-phenyl]-2-cyclohexylmethyl-succinamic acid methyl ester, and was isolated as an HCl salt.

(e) $N^1$-(2-Benzyloxy-1-carbamoyl-ethyl)-$N^4$-[4-(5-chloro-1H-benzoimidazol-2-yl)-henyl]-2-cyclohexylmethyl-succinamide

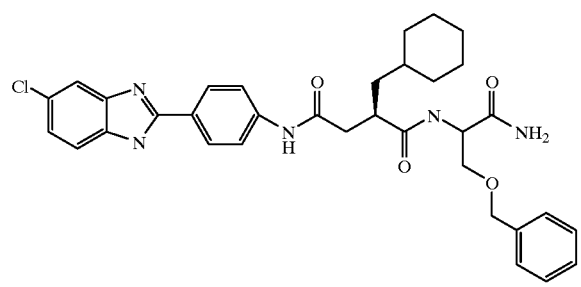

This compound was prepared by the procedure described in Example 1 part (e) from N-[4-(5-Chloro-1H-benzoimidazol-2-yl)-phenyl]-2-cyclohexylmethyl-succinamic acid and the HCl salt of O-benzyl-L-serineamide to give the crude product which was chromatographed (SiO₂, 30% hexanes in EtOAc) to yield the title compound in 76% yield.

(f) $N^1$-(Benzyloxymethyl-cyano-methyl)-$N^4$-[4-(5-chloro-H-benzoimidazol-2-yl)-henyl]-2-cyclohexylmethyl-succinamide

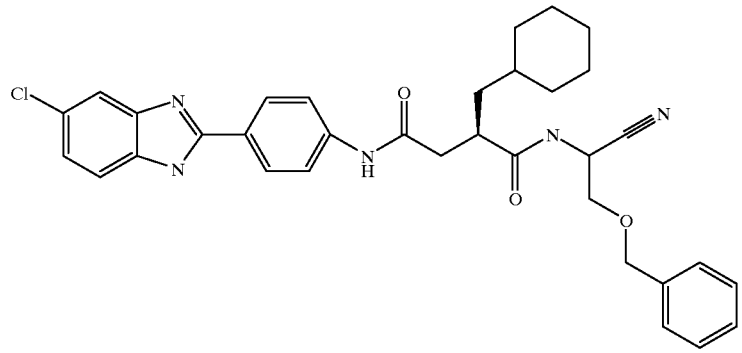

The amide from the step above (0.08 g, 0.13 mmol) and cyanuric chloride (0.024 g, 0.13 mmol) were reacted as described by the procedure in Example 1 part (f). The residue was purified by chromatography (SiO₂, 35% MeOH in CH₂Cl₂) to give the title compound as two separated diastereomers (0.05 g, 64%); ¹H NMR (CDCl₃) 8.2–7.92 (2H, m), 7.8–7.72 (2H, m), 7.57–7.44 (2H, m), 7.3–7.15

(6H, m), 5.47 (1H, m), 4.5–4.4 (2H, m), 3.65–3.5 (2H, m), 3.1–3.0 (1H, m), 2.67–2.54 (1H, m), 2.47–2.34 (1H, m), 1.95–1.5 (7H, m), 1.4–1.15 (6H, m), 1.0–0.8 (3H, m). MS: m/z=599 M+1.

Example 4

N-(Cyano-cyclopropyl)-2-cyclohexylmethyl-4-morpholin-4-yl-4-oxo-butyramide

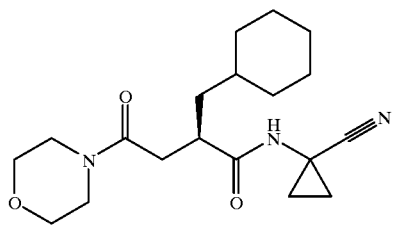

(a) 1-Amino-1-cyclopropanecarboxamide HCl

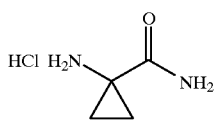

This compound was prepared by the procedures described in Example 1 part (c and d) from 1-tert-Butoxycarbonylamino-cyclopropanecarboxylic acid.

(b) 1-(2-Cyclohexylmethyl-4-morpholin-4-yl-4-oxo-butyrylamino)-cyclopropanecarboxylic acid amide

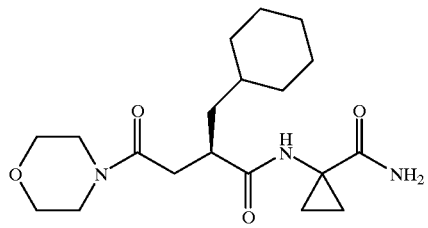

1-(2-Cyclohexylmethyl-4-morpholin-4-yl-4-oxo-butyrylainino)-cyclopropanecarboxylic acid amide was prepared by the procedure described in Example 1 part (e) from (R)-2-cyclohexylmethyl-4-morpholin-4-yl-4-oxo-butrric acid (0.20 g, 0.71 mmol), EDC (0.18 g, 0.92 mmol), 1-hydroxybenzotriazole (0.12 g, 0.92 mmol) and the HCl salt of 1-amino-1-cyclopropanecarboxamide (0.096 g, 0.71 mmol) to yield a white solid (0.084, 33%) after purification by preparative HPLC.

(c) N-(Cyano-cyclopropyl)-2-cyclohexylmethyl-4-morpholin-4-yl-4-oxo-butyramide

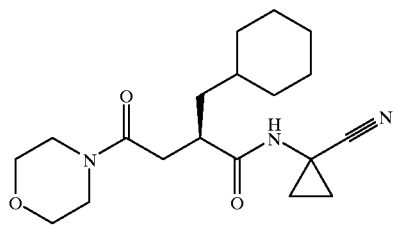

The amide from the step above (0.084 g, 0.23 mmol) and cyanuric chloride (0.042 g, 0.23 mmol) were reacted as described by the procedure in Example 1 part (f). The residue was purified by chromatography (SiO$_2$, 2% MeOH in CH$_2$Cl$_2$) to give the title compound as a clear oil (0.03 g, 38%); $^1$H NMR (CDCl$_3$) 7.38 (1H, m), 3.75–3.36 (8H, m), 2.85–2.68 (2H, m), 2.26–2.17 (1H, m), 1.74–1.53 (6H, m), 1.52–1.40 (2H), 1.27–1.02 (7H, m), 0.90–0.74 (2H, m). MS: m/z=348 M+1.

Example 5

N-(Cyano-1-methyl-piperidin-4-yl)-2-cyclohexylmethyl-4-morpholin-4-yl-4-oxo-butyramide

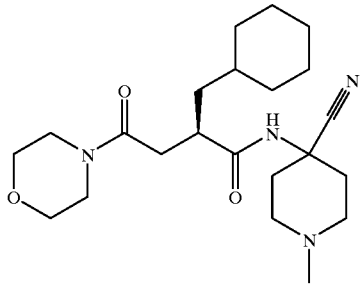

(a) 4-Amino-4-cyano-1-methylpiperidine

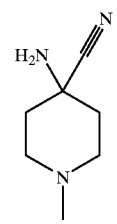

A solution of ammonium chloride (1.89 g, 35.37 mmol) and potassium cyanide (2.30 g, 35.37 mmol) was prepared in 50 mL of water. 1-Methyl-4-piperidone (1 g, 8.84 mmol) was added to the solution and shirring was continued for 2 days. The solution was brought to pH 11 with solid sodium carbonate and the reaction solution was extracted with 3×100 mL of EtOAc. The organic layer was dried over Na$_2$SO$_4$, decanted and concentrated to an orange oil (857 mg). $^1$H NMR showed that the oil was a 2:1:1 mixture of 4-amino-4-cyano-1-methylpiperidine, the corresponding cyanohydrin and starting ketone. The crude mixture was used in the next step without further purification.

(b) N-(Cyano-1-methyl-piperidin-4-yl)-2-cyclohexylmethyl-4-morpholin-4-yl-4-oxo-butyramide

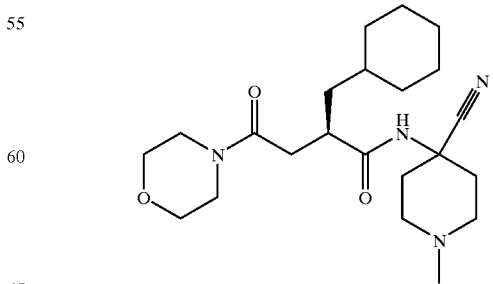

(R)-2-Cyclohexylmethyl-4-morpholin-4-yl-4-oxo-butyric acid (0.20 g, 0.71 mmol) (see Example 1-part a and b) was dissolved in 5 mL of DMF and cooled to 0° C. by an ice-water bath. EDC (0.18 g, 0.92 mmol) and 1-hydroxybenzotriazole (0.12 g, 0.92 mmol) were added and stirring, under argon, continued for 25 min. Then 4-amino-4-cyano-1-methylpiperidine (0.098 g, of the mixture of aminonitrile:cyanohydrin:ketone) was dissolved in 1 mL of DMF and added to the solution of the active ester. The resulting mixture was stirred at ambient temperature for 4 h. The volatiles were removed in vacuo and the resulting residue was dissolved in 100 mL of EtOAc and washed sequentially with 2×100 mL of saturated sodium bicarbonate and 1×100 mL of brine. The organic layer was dried over MgSO$_4$, filtered, and concentrated to a thick oil. The oil was purified by column chromatography on SiO$_2$ using as eluent 5% MeOH in CH$_2$Cl$_2$ to give the title compound as a clear oil (0.005 g): $^1$H NMR (CDCl$_3$) 6.64 (1H, m), 3.73–3.37 (8H, m), 2.95–2.85 (1H, m), 2.75–2.55 (2H, m), 2.5–2.37 (2H, m), 2.34–2.25 (3H, m), 1.98–1.82 (2H, m), 1.80–1.58 (6H, m), 1.32–1.10 (8H, m), 0.95–0.78 (3H,m). MS: m/z= 405 M+1.

Example 6

N-(Cyano-1-benzyl-pyrrolidin-3-ylcarbamoyl)-2-cyclohexylmethyl-4-morpholin-4-yl-4-oxo-butyramide

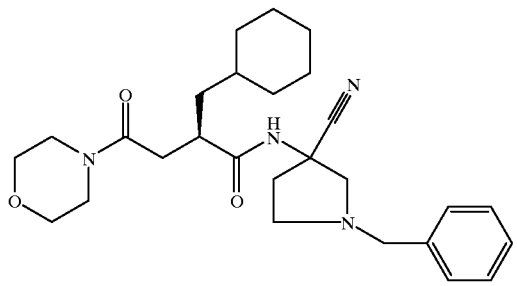

(a) 3-Amino-3-cyano-1-benzylpyrrolidine

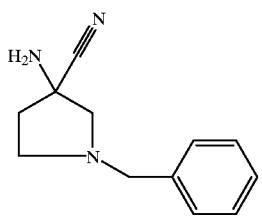

3-Amino-3-cyano-1-benzylpyrrolidine was prepared by a method analogous to that of Example 5-part (a) with the exception that no sodium carbonate was added to the reaction mixture. The product was extracted from the crude reaction with 3×100 mL of EtOAc and was used without purification.

(b) N-(Cyano-1-benzyl-pyrrolidin-3-ylcarbamoyl)-2-cyclohexylmethyl-4-morpholin-4-yl-4-oxo-butyramide. Separated diastereomers

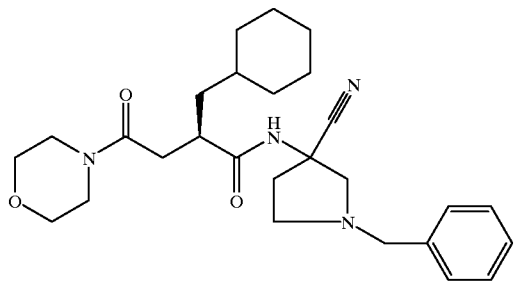

Diastereomeric N-(cyano-1-benzyl-pyrrolidin-3-ylcarbamoyl)-2-cyclohexylmethyl-4-morpholin-4-yl-4-oxo-butyramide was prepared by a method analogous to that of Example 3-part (d). The purification was done by reverse phase preparative HPLC to separate the two diastereomers. $^1$H NMR (CDCl$_3$) 7.31 (5H, m), 6.81 (1H, s), 3.66–3.47 (10H, m), 3.21–3.18 (1H, m), 2.85–2.67 (5H, m), 2.3–2.1 (3H, m), 1.72–1.65 (5H, m), 1.25–1.16 (5H, m), 0.95–0.78 (3H,m). MS, m/z 467=M+1.

Example 7

N-(3-Cyano-1-(3,3-dimethyl-butyl)-pyrrolidin-3-ylcarbamoyl)-2-cyclohexylmethyl-4-morpholin-4-yl-4-oxo-butyramide

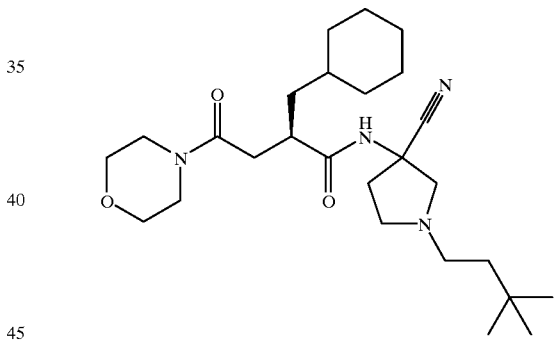

(a) 1-(3,3-Dimethyl-butyl)-pyrrolidin-3-ol

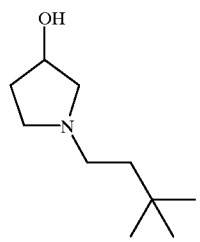

Acetic acid (31 μL), pyrrolidin-3-ol (3.47 g, 39.8 mnol) and 3,3-dimethyl-butyraldehyde (3.99 g, 39.8 mmol) were dissolved in THF (100 mL) and stirred at room temperature for 40 min. The solution was then cooled to 0° C. on an ice bath. To the cold solution sodium triacetoxyborohydride (10.98 g, 51.8 mmol) was added and the mixture was stirred at room temperature overnight. The reaction mixture was basified with a 5.0 M solution of NaOH and extracted with CH₂Cl₂ (3×150 mL). The organic layer was dried over Na₂SO₄, filtered and concentrated to dryness to afford 1-(3,3-dimethyl-butyl)-pyrrolidin-3-ol in (6.34 g, 92.5%), which was used without purification.

(b) 1-(3,3-Dimethyl-butyl)-pyrrolidin-3-one

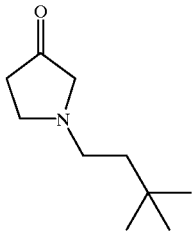

To a dry 500 mL round bottom flask was added oxalyl chloride (9.40 g, 74.06 mmol) in anhydrous CH₂Cl₂ (180 mL) and this solution was cooled to −78° C. DMSO (11.57 g, 148.08 mmol) was added via syringe over a 15 min period during which vigorous gas evolution was observed and the mixture was stirred for 25 min. To the mixture was added 1-(3,3-dimethyl-butyl)-pyrrolidin-3-ol (6.34 g, 37.01 mmol) in CH₂Cl₂ (20 mL) via syringe over a 10 min period. The mixture was stirred for one h at −78° C., then Et₃N (29.96 g, 296.08 mmol) was added via syringe and the dry ice/acetone bath was removed to allow the reaction mixture to warm up to room temperature over 2 h.

The reaction mixture was poured into H₂O (250 mL), the layers were separated and the aqueous was washed with CH₂Cl₂ (3×150 mL). The organic layers were combined and washed with NaHCO₃ (200 mL), brine (200 mL), dried over Na₂SO₄, filtered, then concentrated. The product was purified by column chromatography on SiO₂ using as eluent 100% CH₂Cl₂ to afford the title compound in (3.5 g, 56% yield).

(c) 3-Amino-1-(3,3-dimethyl-butyl)-pyrrolidine-3-carbonitrile

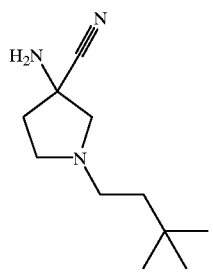

To a dry 250 mL round bottom flask set with a condenser was added sodium cyanide (0.786 g, 16.03 mmol), ammonium chloride (0.904 g, 16.9 mmol) and NH₃/MeOH (2.0 M, 15.36 mL, 30.7 mmol). To the mixture was added 1-(3,3-dimethyl-butyl)-pyrrolidin-3-one (2.60 g, 15.36 mmol) and MgSO₄ (2.5 g). The mixture was heated at 60° C. in an oil bath and stirred for 4 h. The mixture was cooled to room temperature and filtered to remove the insolubles, the filtrate was concentrated to dryness and the residue was dissolved in EtOAc/Et₂O and filtered through a pad of diatomaceous earth then concentrated to dryness to give the title compound in (1.5 g, 51% yield). The crude compound was used in the next step without further purification.

(d) N-(3-Cyano-1-(3,3-dimethyl-butyl)-pyrrolidin-3-ylcarbamoyl)-2-cyclohexylmethyl-4-morpholin-4-yl-4-oxo-butyramide

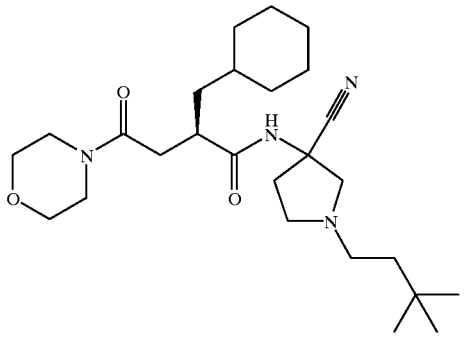

Diastereomeric N-(3-cyano-1-(3,3-dimethyl-butyl)-pyrrolidin-3-ylcarbamoyl)-2-cyclohexylmethyl-4-morpholin-4-yl-4-oxo-butyramide was prepared by a method analogous to that of Example 3-part (d). The purification was done by reverse phase preparative HPLC to separate the two diastereomers. $^1$H NMR (CDCl₃) 6.95 (1H, s), 3.7–3.4 (8H, m), 3.1–3.07 (1H, m), 2.9–2.52 (5H, m), 2.45–2.39 (2H, m), 2.3–2.08 (3H, m), 1.78–1.6 (5H, m), 1.38–1.3 (2H, m), 1.3–1.1 (5H, m), 0.95–0.78 (12H,m). MS, m/z 461=M+1.

Example 8

N-(1-cyano-3-piperidin-1-yl-propyl)-2-cyclohexylmethyl-4-morpholin-4=yl-4-oxo-butyramide

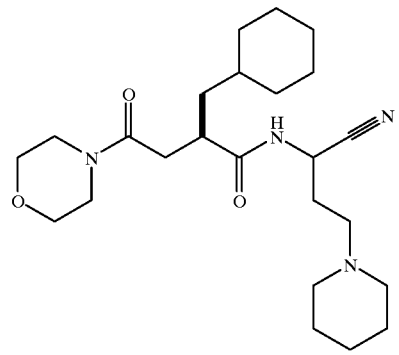

(a) 2-tert-Butoxycarbonylamino-N-methoxy-N-methyl succinamic acid benzyl ester

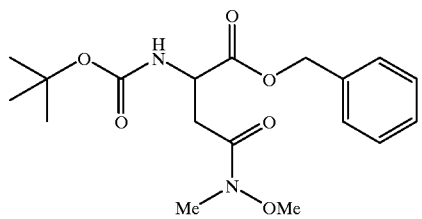

This compound was prepared by a method analogous to that of Example 3-part (d) from N,O-Dimethylhydroxylamine hydrochloride and 2-tert-Butoxycarbonylamino-succinic acid 1-benzyl ester.

(b) 2-tert-Butoxycarbonylamino-4-oxo-butyric acid benzyl ester

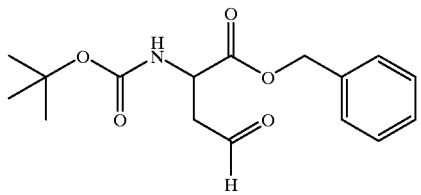

To 2-tert-butoxycarbonylamino-N-methoxy-N-methyl succinamic acid benzyl ester (0.50 g, 1.36 mmol) in THF (5 mL) at −78° C. was added DIBAL-H (0.233 g, 1.67 mmol) dropwise. The mixture was stirred for 1.5 h and monitored by TLC. When completed the reaction was quenched with 5 mL of saturated solution of Rochell salt ($KNaC_4H_4O_6 \cdot 4H_2O$) (potassium sodium tartrate) and extracted with EtOAc (2×10 mL). The organic layer was washed with $H_2O$, brine, dried over $Na_2SO_4$, filtered and concentrated in vacuo to give the title compound in quantitative yield (0.40 g).

(c) 2-tert-Butoxycarbonylamino-4-piperidin-1-yl-butyric acid benzyl ester

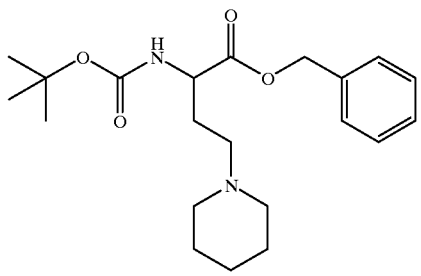

This compound was prepared by a method analogous to that of Example 5-part (a) from 2-tert-butoxycarbonylamino-4-oxo-butyric acid benzyl ester and piperidine. The product was dissolved in 20% TFA in $CH_2Cl_2$ (10 mL) at 0° C., then it was allowed to stir for 1 h at room temperature. The solvent was evaporated to give the diamine TFA salt.

(d) 2-(2-Cyclohexylmethyl-4-morpholin-4-yl-4-oxo-butyrylamino)-4-piperidin-1-yl-butyric acid benzyl ester

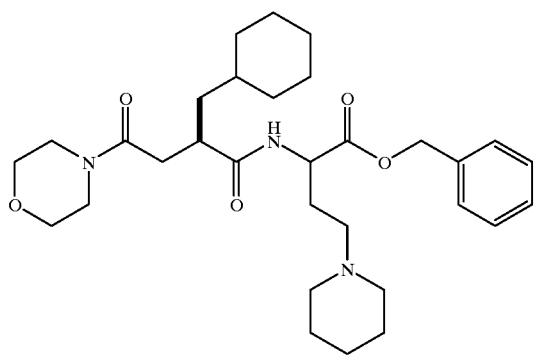

This compound was prepared by a method analogous to that of Example 3-part (d) from the above TFA diamine salt and (R)-2-cyclohexyhmethyl-4-morpholin-4-yl-4-oxo-butyric acid.

(e) N-(1-Carbamoyl-3-piperidin-1-yl-propyl)-2-cyclohexylmethyl-4-morpholin-4-oxo-butyramide

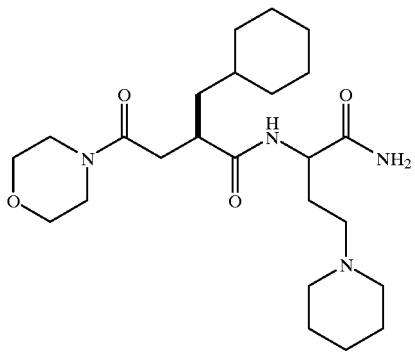

To 2-(2-cyclohexylmethyl-4-morpholin-4-yl-4-oxo-butyriylamino)-4-piperidin-1-yl-butyric acid benzyl ester (0.10 g, 0.18 mmnol) was added $NH_3$/MeOH (2.0 M, 10 mL) in a sealed tube and the mixture was stirred at room temperature for 3 days. The solvent was evaporated to give the title compound in 50% yield.

(f) N-(1-Cyano-3-piperidin-1-yl-propyl)-2-cyclohexylmethyl-4-morpholn-4-yl-4-oxo-butyramide

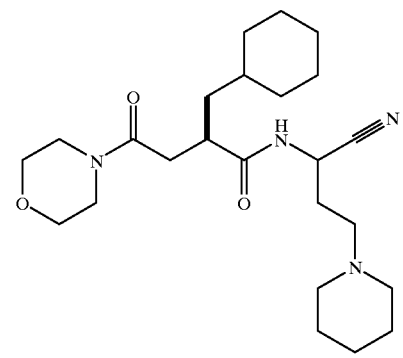

This compound was prepared by a method analogous to that of Example 1-part (f) from N-(1-Carbamoyl-3-piperidin-1-yl-propyl)-2-cyclohexylmethyl-4-morpholin-4-yl-4-oxo-butyramide.

le;2q$^1$H NMR (CDCl$_3$) 4.98–4.94 (1H, m), 3.74–3.45 (8H, m), 3.05–2.2 (9H, m), 2.15–1.4 (11H, m), 1.35–1.05 (7H, m), 0.92–0.75 (3H, m). MS: m/z=433 M+1.

Example 9

N-[3-Cyano-1-(1H-indol-2-ylmethyl)-pyrrolidin-3-yl]-2-cyclohexylmethyl-4-morpholin-4-yl-4-oxo-butyramide

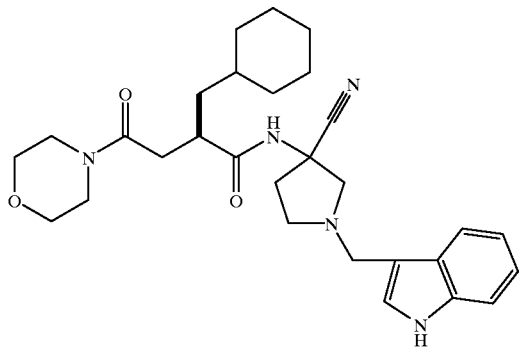

(a) 1-(Toluene-4-sulfonyl)-1H-indole-3-carboxaldehyde

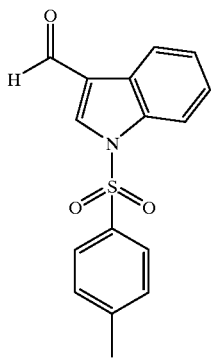

This compound was prepared according to the reference below: Chauhan, P. M. S., Chaterjee, R. K. Indian J. Chem. Sect. B, 1994, 33 (1), 32–37.

(b) N-{3-Cyano-1-[1-(toluene-4-sulfonyl)-1H-indole-3-ylmethyl]-pyrrolidin-3-yl}-2 cyclohexylmethyl-4-morpholin-4yl-4-oxo-butyramide

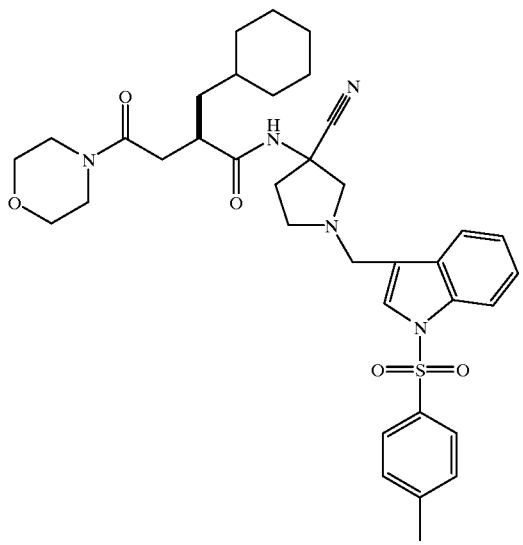

This compound was prepared by a method analogous to that of Example 3-part (a through d) from 1-(toluene-4-sulfonyl)-1H-indole-3-carboxaldehyde and (R)-2-cyclohexylmethyl-4-morpholin-4-yl-4-oxo-butyric acid.

(c) N-[3-Cyano-1-(1H-indol-2-ylmethyl)-pyrrolidin-3-yl]-2-cyclohexylmethyl-4-morpholin-4-yl-4-oxo-butyramide

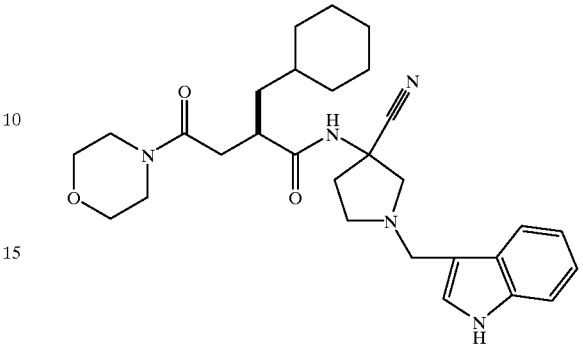

A suspension of N-{3-cyano-1-[1-(toluene-4-sulfonyl)-1H-indole-3-ylmethyl]-pyrrolidin-3-yl}-2-cyclohexylmethyl-4-morpholin-4-yl-4-oxo-butyramide (0.052 g, 0.079 mmol) and Mg (powder) (0.038 g, 1.6 mmol) in MeOH (5 mL) was sonicated at room temperature reaction was monitored by MS. When completed, the reaction mixture was poured into a saturated solution of $NH_4Cl$ and extracted with $CH_2Cl_2$. The combined organic extracts were dried over $Na_2SO_4$ and concentrated to provide the title compound in 76% yield. The compound was recrystallized from Et2O/hexanes. 1H NMR (CDCl3) 8.1 (1H, s), 7.71–7.69 (1H, m), 7.39–7.37 (1H, m), 7.25–7.15 (3H, m), 6.9 (1H, s), 4.0–3.8 (2H, m), 3.7–3.3 (11H, m), 3.2–3.1 (1H, m), 3.0–2.5 (3H, m), 2.3–2.15 (2H, m), 1.8–1.4 (5H, m), 1.35–1.03 (5H, m), 0.95–0.78 (3H,m). MS, m/z 506=M+1.

Listed below are additional examples of compounds of the invention, which were prepared by methods analogous to these described above.

4-Methyl-2-(2-morpholin-4-yl-2-oxo-ethyl)-pentanoic acid (2-benzyloxy-1-cyano-ethyl)-amide. MS: m/z=402 M+1.

N-(1-Cyano-3-phenyl-propyl)-2-cyclohexylmethyl-4-morpholin-4-yl-4-oxo-butyramide. MS: m/z=426 M+1.

4,4-Dimethyl-2-(2-morpholin-4-yl-2-oxo-ethyl)pentanoic acid (2-benzyloxy-1-cyano-ethyl)-amide. MS: m/z=416 M+1.

4,4-Dimethyl-2-(2-morpholin-4-yl-2-oxo-ethyl)-pentanoic acid (1-cyano-3-phenyl-propyl)-amide. MS: m/z=400 M+1.

N-(2-Benzyloxy-1-cyano-ethyl)-4-morpholin-4-yl-2-naphthalen-2-ylmethyl-4-oxo-butyramide. MS: m/z=486 M+1.

N-[2-(4-Chloro-benzyloxy)-1-cyano-ethyl]-2-cyclohexylmethyl-4-morpholin-4-yl-4-oxo-butyramide. MS: m/z=477 M+1.

$N^4$-[2-(4-Acetylamino-phenyl)-$N^1$-(2-benzyloxy)-1-cyano-ethyl]-2-cyclohexylmethyl-succinamide. MS: m/z=505 M+1.

4,4-Dimethyl-2-(2-morpholin-4-yl-2-oxo-ethyl)-pentanoic acid (4-cyano-1-propyl-piperidin-4-yl)-amide. MS: m/z=407 M+1.

4,4-Dimethyl-2-(2-morpholin-4yl-2-oxo-ethyl)-pentanoic acid (1-benzyl-4-cyano-piperidin-4-yl)-amide. MS: m/z=455 M+1.

N-(1-Benzyl-4-cyano-piperidin-4-yl)-2-cyclohexymethyl-4-morpholin-4-yl-4-oxo-butyramide. MS: m/z=481 M+1.

N-[1-(3-Benzyloxy-benzyl)-3-cyano-pyrrolidin-3-yl]-2-cyclohexylmethyl-4-morpholin-4-yl-4-oxo-butyramide. MS: m/z=573 M+1.

N-(3-Cyano-1-cyclohexylmethyl-pyrrolidin-3-yl)-2-cyclohexylmethyl-4-morpholin-4-yl-4-oxo-butyramide. MS: m/z=473 M+1
N-[3-Cyano-1-(2,6-difluoro-benzyl)-pyrrolidin-3-yl]-2-cyclohexylmethyl-4-morpholin-4-yl-4-oxo-butyramide. MS: m/z=503 M+1.
N-[3-Cyano-1-(3,5-difluoro-benzyl)-pyrrolidin-3-yl]-2-cyclohexylmethyl-4-morpholin-4-yl-4-oxo-butyramide. MS: m/z=503 M+1.
N-[3-Cyano-1-(3-trifluoromethyl-benzyl)-pyrrolidin-3-yl]-2-cyclohexylmetyl-4-morpholin-4-yl-4-oxo-butyramide. MS: m/z=535 M+1.
N-(3-Cyano-1-cyclohexyl-pyrrolidin-3-yl)-2-cyclohexylmethyl-4-morpholin-4-yl-4-oxo-butyramide. MS: m/z=459 M+1.
4,4-Dimethyl-2-[2-(4-methyl-piperazin-1-yl)-2-oxo-ethyl]-pentanoic acid (3-cyano-1-cyclohexylmethyl-pyrrolidin-3-yl)-amide. MS: m/z=460 M+1.
4,4-Dimethyl-2-(2-morpholin-4-yl-2-oxo-ethyl)-pentanoic acid (3-cyano-1-cyclohexylmethyl-pyrrolidin-3-yl)-amide. MS: m/z=447 M+1.
4,4-Dimethyl-2-(2-oxo-2-piperidin-1-yl-ethyl)-pentanoic acid (3-cyano-1-cyclohexylmethyl-pyrrolidin-3-yl)-amide. MS: m/z=445 M+1.
4,4-Dimethyl-2-(2-oxo-2-thiomorpholin-4-yl-ethyl)-pentanoic acid (3-cyano-1-cyclohexylmethyl-pyrrolidin-3-yl)-amide. MS: m/z=463 M+1.
N-(3-Cyano-1-isopropyl-pyrrolidin-3-yl)-2-cyclohexylmethyl-4-morpholin-4-yl-4-oxo-butyramide. MS: m/z=419 M+1.
N-(3-Cyano-1-methyl-pyrrolidin-3-yl)-2-cyclohexylmethyl-4-morpholin-4-yl-4-oxo-butyramide. MS: m/z=391 M+1.
N-[3-Cyano-1-(-ethyl-propyl)-pyrrolidin-3-yl]-2-cyclohexylmethyl-4-morpholin-4-yl-4-oxo-butyramide. MS: m/z=447 M+1.
N-(3-Cyano-1-isobutyl-pyrrolidin-3-yl)-2-cyclohexylmethyl-4-morpholin-4-yl-4-oxo-butyramide. MS: m/z=433 M+1.
N-(3-Cyano-1-cyclopropylmethyl-pyrrolidin-3-yl)-2-cyclohexylmethyl-4-morpholin-4-yl-4-oxo-butyramide. MS: m/z=431 M+1.
N-(3-Cyano-1-phenethyl-pyrrolidin-3-yl)-2-cyclohexylmethyl-4-morpholin-4-yl-4-oxo-butyramide. MS: m/z=481 M+1.
N-(3-Cyano-1-methyl-piperidin-3-yl)-2-cyclohexylmethyl-4-morpholin-4-yl-4-oxo-butyramide. MS: m/z=405 M+1.
N-[3-Cyano-1-(4-methyl-cyclohexyl)-pyrrolidin-3-yl]-2-cyclohexylmethyl-4-morpholin-4-yl-4-oxo-butyramide. MS: m/z=473 M+1.
N-(3-Cyano-1-propyl-pyrrolidin-3-yl)-2-cyclohexylmethyl-4-morpholin-4-yl-4-oxo-butyramide. MS: m/z=419 M+1.
N-(3-Cyano-1-cyclopentyl-pyrrolidin-3-yl)-2-cyclohexylmethyl-4-morpholin-4-yl-4-oxo-butyramide. MS: m/z=445 M+1.
N-[1-Cyano-3-(cyclohexyl-ethyl-amino)-propyl]-2-cyclohexylmethyl-4-morpholin-4-yl-4-oxo-butyramide. MS: m/z=475 M+1.
N-[3-(Benzyl-isopropyl-amino)-1-cyano-propyl]-2-cyclohexylmethyl-4-morpholin-4-yl-4-oxo-butyramide. MS: m/z=497 M+1.
N-(3-Cyano-1-cycloheptyl-pyrrolidin-3-yl)-2-cyclohexylmethyl-4-morpholin-4-yl-4-oxo-butyramide. MS: m/z=473 M+1.
N-[3-Cyano-1-(1,2,3,4-tetrahydro-naphthalen-1-yl)-pylolidin-3-yl]-2-cyclohexylmethyl-4-morpholin-4-yl-4-oxo-butyramide. MS: m/z=507 M+1.
N-(1-Bicyclo[2.2.1]hept-2-yl-3-cyano-pyrrolidin-3-yl)-2-cyclohexylmethyl-4-morpholin-4-yl-4-oxo-butyramide. MS: m/z=471 M+1.
N-(4-Cyano-1-propyl-piperidin-4-yl)-2-cyclohexylmethyl-4-morpholin-4-yl-4-oxo-butyramide. MS: m/z=433 M+1.
N-(1-Benzyl-4-cyano-piperidin-4-yl)-2-cyclohexynethyl-4-morpholin-4-yl-4-oxo-butyramide. MS: m/z=487 M+1.
N-[3-Cyano-1-(tetrahydro-pyran-4-yl)-pyrrolidin-3-yl]-2-cyclohexylmethyl-4-morpholin-4-yl-4-oxo-butyramide, MS: m/z 461=M+1. (1:1 mixture of diastereomers)
N-[3-Cyano-1-(tetrahydro-thiopyran-4-yl)-pyrrolidin-3-yl]-2-cyclohexylmethyl-4-morpholin-4-yl-4-oxo-butyramide, MS: m/z 477=M+1. (single diastereomer)
N-[3-Cyano-1-(tetrahydro-thiopyran-4-yl)-pyrrolidin-3-yl]-2-cyclohexylmethyl-4-morpholin-4-yl-4-oxo-butyramide, MS: m/z 477=M+1 (single diastereomer)
N-[3-Cyano-1-(2-phenyl-benzyl)-pyrrolidin-3[-yl]-2-cyclohexylmethyl-4-morpholin-4-yl-4-oxo-butyramide; MS, m/z 543=M+1
N-[3-Cyano-1-(3-phenyl-benzyl)-pyrrolidim-3-yl]-2-cyclohexylmethyl-4-morpholin-4-yl-4-oxo-butyramide; MS, m/z 543=M+1
N-(4-Cyano-2-phenethyl-2H-pyrazol-3-yl)-(2R)-2-cyclohexylmethyl-4-morpbolin-4-yl-4-oxo-butyramide
N-(4-Cyano-1-phenethyl-1H-pyrazol-3-yl)-(2R)-2-cyclohexylmethyl-4-morpholin-4-yl-4-oxo-butyramide
N-[(3S)-3-Cyano-1-(2-methyl-2-phenyl-propyl)-pyrrolidin-3-yl]-(2R)-2-cyclohexylmethyl-4-morpholin-4-yl-4-oxo-butyramide
N-[(3R)-3-Cyano-1-(2-methyl-2-phenyl-propyl)-pyrrolidin-3-yl]-(2R)-2-cyclohexylmethyl-4-morpholin-4-yl-4-oxo-butyramide
N-[(S)-Cyano-methyl-phenyl-methyl]-(2R)-2-cyclohexylmethyl-4-morpholin-4-yl-4-oxo-butyramide
N-[(R)-Cyano-methyl-phenyl-methyl]-(2R)-2-cyclohexylmethyl-4-morpholin-4-yl-4-oxo-butyramide
N-[(S)-Cyano-methyl-pyridin-4-yl-methyl]-(2R)-2-cyclohexylmethyl-4-morpholin-4-yl-4-oxo-butyramide
N-[(R)-Cyano-methyl-pyridin-4-yl-methyl]-(2R)-2-cyclohexylmethyl-4-morpholin-4-yl-4-oxo-butyramide
N-[(3S)-3-Cyano-1-indan-2-ylmethyl-pyrrolidin-3-yl]-(2R)-2-cyclohexylmethyl-4-morpholin-4-yl-4-oxo-butyramide
N-[(3R)-3-Cyano-1-indan-2-ylmethyl-pyrrolidin-3-yl]-(2R)-2-cyclohexylmethyl-4-morpholin-4-yl-4-oxo-butyramide
N-[(3S)-3-Cyano-1-(5-methyl-thiophen-2-ylmethyl)-pyrrolidin-3-yl]-(2S)-2-cyclohexylmethyl-4-morpholin-4-yl-4-oxo-butyramide
N-[(3S)-3-Cyano-1-(5-methyl-thiophen-2-ylmethyl)pyrrolidin-3-yl]-(2S)-2-cyclohexylmethyl-4-morpholin-4-yl-4-oxo-butyramide
N-[(3S)-3-Cyano-pyrrolidin-3-yl]-(2R)-2-cyclohexylmethyl-4-morpholin-4-yl-4-oxo-butyramide
N-[(3R)-3-Cyano-pyrrolidin-3-yl]-(2R)-2-cyclohexylmethyl-4-morpholin-4-yl-4-oxo-butyramide
$N^4$-Carbamoylmethyl-$N^1$-(3-cyano-1-cyclohexyl-pyrrolidin-3-yl)-2-cyclohexylmethyl-$N^4$-methyl-succinamide: $C_{25}H_{41}N_5O_3$, ESMS: 460 (M+1)
{1-[3-(1-Benzyl-3-cyano-pyrrolidin-3-yl carbamoyl)-4-cyclohexyl-butyryl]-pyrrolidin-3-yl}-carbamic acid tert-butyl ester. MS: m/z=566.5 M+1
{1-[3-(3-Cyano-1-cyclohexyl-pyrrolidin-3-yl carbamoyl)-4-cyclohexyl-butyryl]-pyrrolidin-3-yl}-carbamic acid tert-butyl ester. MS: m/z=558.6 M+1
N-(1-Benzyl-3-cyano-pyrrolidin-3-yl)-2-cyclohexylmethyl-4-(3-dimethylamino-pyrrolidin-1-yl)-4-oxo-butyramide. MS: m/z=494.5 M+1
N-(3-Cyano-1-cyclohexyl-pyrrolidin-3-yl)-2-cyclohexylmethyl-4-(2-oxa-5-aza-bicyclo[2.2.1]hept-5-yl)-4-oxo-butyramide. MS: m/z=471 M+1
N-(3-Cyano-1-cyclohexyl-pyrrolidin-3-yl)-2-cyclohexylmethyl-4-(2,6-dimethyl-morpholin-4-yl)-4-oxo-butyramide. MS: m/z=487 M+1
N-(3-Cyano-1-cyclohexyl-pyrrolidin-3-yl)-2-cyclohexylmethyl-4-(2-methoxymethyl-morpholin-4-yl)-4-oxo-butyramide. MS: m/z=503 M+1.

Example 10

N-{1-[(Benzyl-methyl-amino)-methyl]-1-cyano-3-phenyl-propyl}-2-cyclohexylmethyl-4-morpholin-4-yl-4-oxo-butyramide (a) (Benzyl-methyl-amino)-acetic acid methyl ester

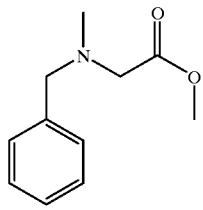

Methyl bromoacetate (10 g, 65.4 mmol, 1.0 equiv) was dissolved in 100 mL of $CH_2Cl_2$ which was then cooled to 0° C. N-Methylbenzylamine (7.92 g, 65.4 mmol, 1.0 equiv) was added dropwise over a 10 min period at which time Hunig's base (21 g, 163 mmol, 2.49 equiv) was added and the reaction was allowed to warm to room temperature and was stirred for 16 h. The reaction was diluted with 50 mL of saturated bicarbarbonate and the layers were separated. The organic layer was washed once more with 50 mL of sodium bicarbonate, dried over $Na_2SO_4$, decanted and concentrated to a yellow oil which was used in the next step without further purification.

(b) (Benzyl-methyl-amino)-acetic acid hydrochloride salt

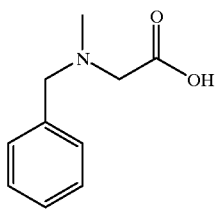

(Benzyl-methyl-amino)-acetic acid methyl ester (12 g, 62.1 mmol, 1.0 equiv) was dissolved in 50 mL of MeOH to which was added a solution of LiOH hydrate (8.23 g, 196 mmol, 3.0 equiv) in 50 mL of water. The mixture was stirred at room temperature for 1.3 h at which time TLC (5% MeOH in $CH_2Cl_2$) indicated consumption of the starting material. The reaction solution was washed 1×50 mL of $Et_2O$ and then the aqueous layer was acidified to pH 1 with concentrated HCl. The mixture was then evaporated to dryness under high vacuum. The resulting solid was triturated with EtOH (200 mL) and the mixture was filtered. The filtrate was then concentrated to dryness to yield a white cystalline solid that was used without further purification.

(c)-2-(Benzyl-methyl-amino)-N-methoxy-N-methy-acetamide

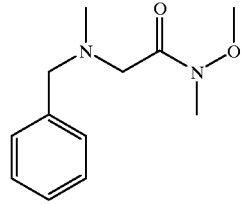

(Benzyl-methyl-amino)-acetic acid hydrochloride salt (12 g, 56 mmol, 1.0 equiv) was mixed in DMF (200 mL) along with EDC (10.6 g, 56 mmol, 1.0 equiv) for 15 min. N,O-Dimethylhydroxylamine hydrochloride (6.52 g, 67 mmol, 1.2 equiv) was added to the reaction followed by N-methylmorpholine (34 mL, 334 mmol, 6.0 equiv). The reaction was stirred for 16 h. The DMF was removed in vacuo and the residue was redissolved in 200 mL of EtOAc. The solution was washed once with 200 mL brine. The organic layer was dried over $Na_2SO_4$, decanted and concentrated to yield the desired product as a free-flowing oil (12.6 g, 80%) that was used in the next step without further purification; MS, m/z 223=M+1.

(d) 1-(Benzyl-methyl-amino)-4phenyl-butan-2-one

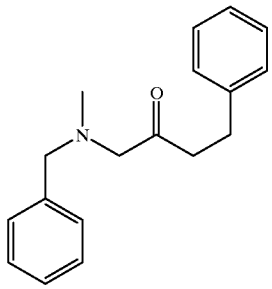

2-(Benzyl-methyl-amino)-N-methoxy-N-methyl-acetainide (2.0 g, 9.0 mmol, 1.0 equiv) was dissolved in 30 mL of dry THF under argon. The solution was cooled to −78° C. and a 1 M solution of phenethyl magnesium chloride (12.6 mL, 12.6 mmol, 1.4 equiv) was added dropwise of a period of 1 min. The resulting mixture was stirred at −78° C. for 3 h, warmed to 0° C. for 20 min and recooled to −78° C. at which time the reaction was quenched by the addition of 5 mL of saturated sodium bicarbonate. The reaction solution was diluted with 200 mL of EtOAc and 200 mL of water. The layers were separated and the organic layer was dried over $Na_2SO_4$, decanted and concentrated to an oil (2.4 g, ~100%) which was used without further purification; MS, m/z 268=M+1.

(e) 2-Amino-2-[(benzyl-methyl-amino)-methyl]-4-phenyl-butyronitrile

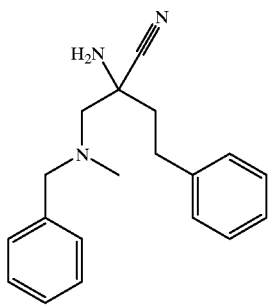

1-(Benzyl-methyl-amino)-4-phenyl-butan-2-one (2.4 g, 9.0 mmol, 1.0 equiv) was mixed in 36 mL of 2.0 M $NH_3$ in MeOH. To the solution was added NaCN (0.484 g, 9.9 mmol, 1.1 equiv) and $NH_4Cl$ (0.528 g, 9.9 mmol, 1.1 equiv). The resulting mixture was refluxed for 2 h at which time an addition 15 mL of 2.0 M $NH_3$ in MeOH was added and the mixture was refluxed another 4 h. Though TLC (5% MeOH in $CH_2Cl_2$) still showed the presence of the ketone, the reaction was cooled and filtered. The filtrate was concentrated and the crude product was purified by flash chromatography on $SiO_2$ using 60% hexanes in $CH_2Cl_2$ then 1.5% MeOH to 3% MeOH was added. The desired product was isolated pure (0.561 g, 21%) as a yellow oil that crystallized upon standing at −20° C.; MS, m/z 294=M+1.

(f) N-{1-[(benzyl-methyl-amino)-methyl]-1-cyano-3-phenyl-propyl}-2-cyclohexylmethyl-4-morpholin-4-yl-oxo-butyramide

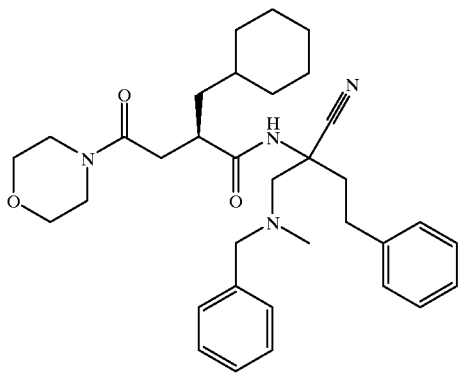

2-Cyclohexylmethyl-4-morpholin-4-yl-oxo-butanoic acid (0.097 g, 0.34 mmol, 1.0 equiv) was dissolved in 10 mL of $CH_2Cl_2$ followed by addition of EDC (0.065 g, 0.34 mmol, 1.0 equiv). The solution was stirred for 15 min at which time a solution of 2-amino-2-[(benzyl-methyl-amino)-methyl]-4-phenyl-butyronitrile (0.10 g, 0.34 mmol, 1.0 equiv) in 5 mL of $CH_2Cl_2$ was added followed by N-methylmorpholine (0.137 g, 1.36 mmol, 4.0 equiv). The resulting solution was stirred at room temperature for 72 h. The volatiles were removed in vacuo and the residue was redissolved in 100 mL of EtOAc and the solution was washed 2×25 mL brine. The organic layer was evaporated to dryness and the crude product was purified by semi-prep reverse-phase HPLC using 40% $CH_3CN$ in water to 90% over a time of 25 min. The appropriate fractions were combined and concentrated to yield the desired product as a thick oil (0.047 g, 25%); MS, m/z 559=M+1.

Example 11

N-(4-Cyano-1,2-dimethyl-piperidin-4-yl)-2-cyclohexylmethyl-4-morpholin-4-yl-4-oxo-butyramide (a) 3-(Benzyl-methyl-amino)-butyric acid methyl ester

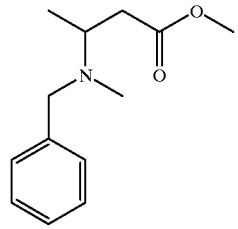

Benzyl-methyl-amine (20 g, 165 mmol, 1.0 equiv) was added neat to methyl crotonate (19.8 g, 198 mmol, 1.2 equiv). The resulting solution was stirred at room temperature for 72 h. The excess crotonic ester was removed in vacuo to yield the desired product (40.3 g, ~100%) which was used without further purification; MS, m/z 222=M+1.

(b) 3-Methylamino-butyric acid methyl ester

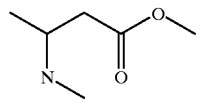

3-(Benzyl-methyl-amino)-butyric acid methyl ester (15 g, 67.8 mmol, 1.0 equiv) was placed in a Parr hydrogenation bottle and dissolved in 50 mL of MeOH. 20% Palladium hydroxide on carbon (0.5 g, 0.94 mmol, 0.014 equiv) was added and the mixture was shaken at 50 psi $H_2$ for 16 h. The reaction was judged as complete when the uptake of $H_2$ had stopped. The bottle was opened and 10 g of diatomaceous earth in 100 mL of MeOH was added. The mixture was filtered on a pad of diatomaceous earth which was then washed with 2×100 mL of MeOH. The filtrates were combined and concentrated in vacuo to yield the desired product as an oil that is somewhat volatile (7.6 g, 85%). The crude product was used without further purification; MS, m/z 132=M+1.

(c) 3-[(2-Methoxycarbonyl-ethyl)-methyl-amino]-butyric acid methyl ester

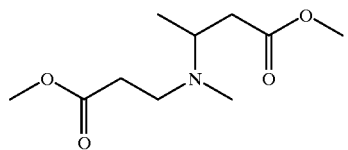

3-Methylamino-butyric acid methyl ester (7.6 g, 58 mmol, 1.0 equiv) was added neat to methyl acrylate (7.5 g, 87 mmol, 1.5 equiv). The resulting solution was refluxed for 16 h. The reaction was cooled and diluted with hexanes (200 mL) and an insoluble polymer separated out. The hexane solution was decanted and the polymer was washed 2×100 mL hexanes with vigorous stirring. The combined hexane solutions were then concentrated in vacuo. The crude product was purified by flash chromatography on $SiO_2$ using pure $CH_2Cl_2$ as an eluent. The pure product was isolated as a clear colorless oil (7.3 g, 58%); MS, m/z 218=M+1.

(d) 1,2-Dimethyl-4-piperidone

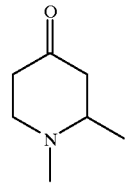

A 1 M solution of $TiCl_4$ in $CH_2Cl_2$ (23 mL, 23 mmmol, 1.0 equiv) was added to a flask under Ar and cooled to −15° C. with a MeOH/ice water bath. 3-[(2-Methoxycarbonyl-ethyl)-methyl-amino]-butyric acid methyl ester (5 g, 23 mmol, 1.0 equiv) was added dropwise over a 25 min period as solution in 75 mL of dry $CH_2Cl_2$ to give a dark red mixture that was difficult to stir with a magnetic stir bar. Stirring was continued an additional 1 h and then $Et_3N$ (5.1 g, 50.6 mmol, 2.2 equiv) was added dropwise over a 30 min period and then the reaction was stirred an additional 1.5 h at −15° C. The reaction mixture was poured into 150 mL of brine and 150 mL of $CH_2Cl_2$ was added. After thorough mixing, the pH of the water was brought to 8–9 with $Et_3N$. The mixture was filtered and the gel-like solid was washed 3×100 mL CH$_2$Cl$_2$. The filtrate layers were separated and the aqueous layer was washed with 3×50 mL CH$_2$Cl$_2$. All of the organic layers were combined and concentrated to a thick red oil. The residue was taken up in 150 mL of concentrated HCl and the solution was refluxed 4 h. The cooled reaction solution was evaporated to dryness and the residue was dissolved in 200 mL of saturated sodium bicarbonate. The product ketone was extracted with 2×100 mL of EtOAc. The organic layers were combined and dried over Na$_2$SO$_4$. The product was purified by flash chromatography on SiO$_2$ using CH$_2$Cl$_2$ to 4% MeOH in CH$_2$Cl$_2$ as eluent. The product was isolated as an orange oil (1.23 g, 42%); MS, m/z 128=M+1.
(e) 4-Amino-4-cyano-1,2-dimethyl-piperidine

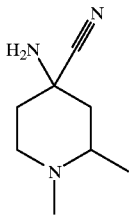

1,2-Dimethyl-4-piperidone (1.23 g, 9.67 mmol, 1.0 equiv) was dissolved in 39 mL of 2 M NH$_3$ in MeOH (8 equiv NH$_3$). To this solution was added NaCN (0.52 g, 10.6 mmol, 1.1 equiv) and NH$_4$Cl (0.57 g, 10.6 mmol, 1.1 equiv). The resulting mixture was refluxed for 2 h at which time an additional 39 mL of 2 M NH$_3$ in MeOH was added followed by an additional 2 h of reflux. The reaction was cooled and filtered. The filtrate was concentrated and taken up in 100 mL of CH$_2$Cl$_2$ giving more salt precipitate which was removed by a second filtration. The filtrate was then concentrated to a thick orange oil (1.32 g, 89%). $^1$H NMR showed a 3 to 1 mixture of diastereomers of unknown configuration. The crude product was used without further purification; MS, m/z 154=M+1.
(f) N-(4-Cyano-1,2-dimethyl-piperidin-4-yl)-2-cycloheyxlmethyl-4-morpholin-4-yl-4-oxo-butyramide

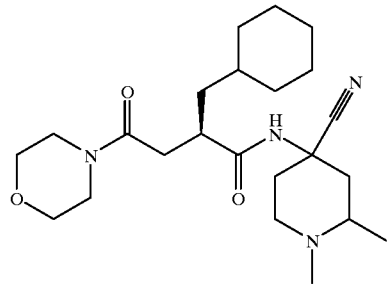

2-Cyclohexylmethyl-4-morpholin-4-yl-oxo-butanoic acid (0.3 g, 1.06 mmol, 1.0 equiv) was mixed with EDC (0.2 g, 1.06 mmol, 1.0 equiv) in 15 mL of DMF. A solution of 4-amino-4-cyano-1,2-dimethyl-piperidine (0.16 g, 1.0 mmol, 0.95 equiv) in 5 mL of DMF was added followed by addition of N-methylmorpholine (0.43 g, 4.24 mmol, 4.0 equiv). The resulting solution was stirred for 16 h. The reaction was diluted with 50 mL of saturated sodium bicarbonate and the product was extracted with 3×50 mL EtOAc. The organic layers were combined and concentrated in vacuo. The crude product was purified by semi-prep reverse-phase HPLC using 20% CH$_3$CN in water to 61% CH$_3$CN in water over a gradient time of 17 min. The product was isolated in two peaks as an undefined mixture of diastereomers about the piperidine ring; MS, m/z 419=M+1 for both HPLC peaks.

Example 12

(4R)-N-(3-Cyano-1-cyclohexyl-pyrrolidin-3yl)-2-(4-methyl-cyclohexylmethyl)-4-morpholin-4-yl-4-oxo-butyramide (a) 3-(4Methyl-cyclohexyl)-acrylic acid ethyl ester Lithium aluminium hydride (560 mg, 60 mmol) was suspended in 20 mL of dry THF. To this suspension at −78° C. under nitrogen was added a solution of trans-4-methyl-1-cyclohexanecarboxylic acid (2.13 g, 15 mmol) in 20 mL of dry THF. This reaction mixture was stirred at −78° C. for 2 h and then warmed up to room temperature in 2 h. The reaction was cooled to 0° C., and quenched with a saturated solution of potassium sodium tartrate and extracted repeatedly with diethyl ether. The combined organic phases were dried over magnesium sulfate and evaporated under reduced pressure to give a clear oil. Yield 100%.

To a solution of oxalyl chloride (1.76 mL, 20 mmol) in 60 mL of dry dichloromethane at −78° C. under nitrogen was added DMSO (2.84 mL, 40 mmol). After the gas evolution stopped, the above oil (1.28 g, 10 mmol) dissolved in 10 mL of dichloromethane was added. The reaction mixture was stirred at −78° C. for 1 h and triethylamine (7 mL, 50 mmol) was added. The reaction was then allowed to warm up to room temperature in 2 h and was quenched with water. The aqueous phase was extracted repeatedly with dichloromethane. The combined organic phases were washed with brine and dried over magnesium sulfate. The solvent was removed under reduced pressure to give a yellow oil, which was used in the next step without further purification. Yield: 1.06 g, 84%.

The above oil (1.06 g, 8.41 mmol) and (carbethoxymethylene)triphenylphosphorane (2.93 g, 8.41 mmol) were heated under reflux in 30 mL of dry toluene under nitrogen for 2 h. The solvent was removed under reduced pressure and the residue was purified by silica gel flash chromatography eluting with 5% diethyl ether in petroleum ether to give a clear oil. Yield: 1.45 g, 88%.

(b) 3-(4-Methyl-cyclohexyl)-propionic acid

The above oil (1.45 g, 7.39 mmol) was dissolved in 20 mL of EtOH and hydrogenated in a Parr apparatus under 50 psi of H$_2$ in the presence of 10% palladium on activated charcoal for 2 h. The solid was removed by filtration and washed with EtOH. The filtrate was evaporated under reduced pressure to give the ethyl ester as a clear oil. Yield: 1.37 g, 94%.

The above ester (1.37 g, 6.98 mmol) was dissolved in 20 mL of THF. A 2 M lithium hydroxide solution (50 mL) was added. This reaction mixture was stirred at room temperature for 16 h. The solution was cooled to 0° C., and acidified with 6 N HCl to pH 2. The resulting white precipitate was collected by filtration and washed with water then dried under vacuum giving the desired acid. Yield: 1.08 g, 91%.

(c) (S)-4-Isopropyl-3-[3-(4-methyl-cyclohexyl)-propionyl]-oxazolidin-2-one

The acid (1.02, 6 mmol) was dissolved in 20 mL of dry dichloromethane and 1 drop of DMF. To this solution at 0° C. was added oxalyl chloride (1.57 mL, 18 mmol). The reaction mixture was stirred at room temperature for 2 h. The solvent was removed under reduced pressure and the resulting acid chloride was used in the next reaction without further purification.

(S)-(−)-4-Isopropyl-2-oxazolidinone (0.775 g, 6 mmol) was dissolved in 20 mL of dry THF. To this solution at −78° C., under nitrogen was added n-butyl lithium (2.5 M, 2.4 mL, 6 mmol). The reaction mixture was stirred at −78° C. for 30 min and then at room temperature for 30 min. To this solution at −78° C. was added the acid chloride dissolved in 20 mL of THF. The reaction was maintained at −78° C. for 1 h then warmed up to room temperature in 2 h and quenched with 1M potassium carbonate solution. The aqueous phase was extracted repeatedly with diethyl ether. The combined organic phases were washed with brine and dried over magnesium sulfate. The solvent was removed under reduced pressure. The residue was purified by silica gel flash chromatography, eluted with 5% diethyl ether in petroleum ether to give a clear oil. Yield: 1.39 g, 82%.

(d) (2R,4'S)-1-(4-Isopropyl-2-oxo-oxazolidin-3-yl)-2-(4methyl-cyclohexylmethyl)-4-morpholin-4-yl-butane-1,4-dione The above compound (0.703 g, 2.5 mmol) was dissolved in 20 mL of dry THF. To this solution at −78° C. and under nitrogen was added sodium bis(trimethylsilyl)amide (0.6 M, 4.2 mL, 2.5 mmol). The reaction mixture was stirred at −78° C. for 1 h. 2-Bromo-1-morpholin-4-yl-ethanone (W. J. Thompson, et al., *J.Med.Chem,* 1992 35 1685–1701) (0.52 g, 2.5 mmol) dissolved in 10 mL of dry THF was added to the above reaction mixture. This solution was maintained at −78° C. for 1 h, warmed up to room temperature in 2 h and quenched with saturated ammonium chloride solution. The aqueous phase was extracted repeatedly with dichloromethane. The combined organic phases were washed with brine and dried over magnesium sulfate. The solvent was removed under reduced pressure. The residue was purified by silica gel flash chromatography, eluting with 1% MeOH in dichloromethane to give a white solid. Yield: 0.82 g, 80%.

(e) (R)-2-(4-Methyl-cyclohexylmethyl)-4-morpholn-4-yl-4-oxo-butyric acid

The above solid (0.82 g, 1.96 mmol) was dissolved in 30 mL of THF and 10 mL of water. To this solution, at 0° C. was added 30 mL of 30% hydrogen peroxide. The reaction mixture was stirred at 0° C. for 2 h and then quenched with sodium sulfite. This solution was acidified with 6 N HCl to pH 2 and then extracted repeatedly with dichloromethane. The combined organic phases were washed with brine and dried over magnesium sulfate. The solvent was removed under reduced pressure. The residue was purified by silica gel flash chromatography, eluted with 2% MeOH in dichloromethane to give a white solid. Yield: 0.31 g, 53%.

(f) (4R)-N-(3-Cyano-1-cyclohexyl-pyrrolidin-3-yl)-2-(4-methyl-cyclohexylmethyl)-4-morpholin-4-yl-4-oxo-butyramide The title compound was prepared using the above intermediate following the procedure described in Example 6, $C_{27}H_{44}N_4O_3$, ESMS: 473 (M+1).

Additional compounds of the present invention prepared by methods analogous to those above include:

(4R)-N-(3-Cyano-1-cyclohexyl-pyrrolidin-3-yl)-2-(1-methyl-cyclohexylmethyl)-4-morpholin-4-yl-4-oxo-butyramide: $C_{27}H_{44}N_4O_3$, ESMS: 473 (M+1).

Example 13

N-(3-Cyano-1-cyclohexyl-pyrrolidin-3yl)-4-morpholin-4-yl-oxo-2-(trans-4-phenyl-cylohexylmethyl)-butyramide (a) 4-Phenyl-cyclohexanecarboxylic acid To a mixture of $AlCl_3$ (13 g, 97.5 mmol, 1.0 equiv) in benzene (100 mL) kept at 35° C., was added 1-cyclohexenecarboxylic acid (5 g, 39.7 mmol, 0.41 equiv) dropwise. After addition was complete, the reaction solution was heated to 70° C. for 1 h and 45° C. overnight. The reaction was cooled, and 200 mL of 1 N HCl was slowly added. The product was extracted with EtOAc. The organic layer was extracted with 1 N NaOH and the aqueous layer was acidified with concentrated HCl to produce a white precipitate that was collected by filtration, washed with water and dried to give the titled compound as a white solid (3.1 g, 38%) which was used without further purification.

(b) 4-Phenyl-cyclohexylmethanol

A suspension of $LiAlH_4$ (0.56 g, 14.8 mmol, 2.0 equiv) was prepared under argon in 50 mL of anhydrous THF (50 mL) kept at 0° C. A solution of 4-phenyl-cyclohexanecarboxylic acid (1.5 g, 7.34 mmol, 1.0 equiv) in 50 mL of THF was added dropwise over a 20 min period. The reaction mixture was stirred at ambient temperature for 1.5 h and then cooled to 0° C. The excess hydride reagent was carefully quenched under argon by dropwise addition of 1 N HCl. After quenching, the reaction mixture was extracted with EtOAc. The organic layer was dried over $MgSO_4$, filtered and concentrated to give the title product as a colorless oil (1.9 g crude) which was used without further purification.

(c) 4-Phenyl-cyclohexylmethyl-p-toluene sulfonate

4-Phenyl-cyclohexylmethanol (2.5 g, 13.1 mmol, 1.0 equiv) was dissolved in chloroform (50 mL) and pyridine (2.1 g, 26.3 mmol, 2.0 equiv) was added and the mixture was cooled to 0° C. A solution of tosyl chloride (3.75 g, 19.7 mmol, 1.5 equiv) in chloroform (30 mL) was added and the resulting solution was stirred at ambient temperature for 30 min. The reaction was diluted with EtOAc (150 mL) and washed 2×100 mL 1N HCl. The organic layer was then washed with 1×100 mL saturated sodium bicarbonate, dried over $MgSO_4$, filtered and concentrated to yield a solid which was used immediately in the next step without further purification.

(d) (4-Phenyl-cyclohexylmethyl)-malonic acid diethyl ester

Diethyl malonate (3.1 g, 19.7 mmol, 1.5 equiv) was added dropwise to a solution of sodium (1.25 g, 54.0 mmol, 4.0 equiv) in EtOH (50 mL). 4-Phenyl-cyclohexylmethyl-p-toluene sulfonate (~13.1 mmol, ~1.0 equiv, the crude product from the previous step) was added as a solution in 50 mL of EtOH. The resulting mixture was refluxed for 8 h. The reaction mixture was cooled and evaporated to dryness and then dissolved in water (150 mL) and the crude product extracted with 3×100 mL EtOAc. The organic layer was dried over $MgSO_4$, filtered and concentrated. The crude product was purified by flash chromatography on $SiO_2$ using 10% EtOAc in hexanes to give the desired product as a colorless oil (2.79 g).

(e) 3-(4-Phenyl-cyclohexylmethyl)-propanoic acid (4-Phenyl-cyclohexylmethyl)-malonic acid diethyl ester (2.79 g, 8.4 mmol, 1.0 equiv) was added to a solution of potassium hydroxide (2.35 g, 41 mmol, 5 equiv) in 20 mL of water and 20 mL of MeOH. The resulting mixture was refluxed for 0.5 h and then evaporated to dryness and then dissolved in 100 mL of water. The solution was washed 3×100 mL with hexane and then brought to pH <1 with concentrated HCl. The product was extracted 3×100 mL EtOAc. The organic layers were combined and concentrated to dryness. The crude product was then heated for 10 min at 180° C. to decarboxylate the diacid and yield the monoacid (0.9 g) which was used without further purification.

(f) N-(3-Cyano-1-cyclohexyl-pyrrolidin-3-yl)-4-morpholin-4yl-4-oxo-2-(trans-4-phenyl-cyclohexylmethyl)butyramide The title compound was prepared using the intermediate from step e above and the procedures reported in Example 12, MS, m/z 535=M+1

Example 14

2- Bicyclo[4.1.0]hept-7-ylmethyl-(3-cyano-1-cyclohexyl-pyrrolidin-3-yl)-4-morpholin-4-yl-4-oxo-butyramide (a) 2-Bicyclo[4.1.0]hept-7-yl-carboxylic acid ethyl ester A mixture of cupric triflate (0.1 g, 0.28 mmol, 0.0016 equiv) was prepared in cyclohexene (100 mL). A 25 mL of a solution of ethyl diazoacetate (20 g, 175 mmol, 1.0 equiv) in cyclohexene (100 mL) was added to initiate the reaction followed by dropwise addition of the remainder to maintain a gentle exothermic reaction. The reaction was then stirred 18 h at room temperature. 200 mg of additional cupric triflate was added to decompose any unreacted diazo acetate and then the mixture was concentrated to dryness. The residue was distilled on a water bath to yield the desired product as a colorless oil (15.7 g).

(b) 2-Bicyclo[4.1.0]hept-7-ylmethyl-N-(3-cyano-1-cyclohexyl-pyrrolidin-3-yl)-4-morpholin-4-yl-4-oxo-butyramide 2-Bicyclo[4.1.0]hept-7-ylmethyl-N-(3-cyano-1-cyclohexyl-pyrrolidin-3-yl)-4-morpholin-4-yl-4-oxo-butyramide was prepared using the procedures outlined in Example 13 and the intermediate generated in step a above; MS, m/z 471=M+1.

Additional compounds of the present invention prepared by methods analogous to those above include:

2-Bicyclo[4.1.0]hept-7-ylmethyl-N-(4-cyano-1-methyl-piperidin-4-yl)-4-morpholin-4-yl-4-oxo-butyramide; MS, m/z 417=M+1.

N-(3-Cyano-1-cyclohexyl-pyrrolidin-3-yl)-4-morpholin-4-yl-4-oxo-2-(1,2,3,4-tetrahydro-naphthalen-2-ylmethyl)-butyramide; MS, m/z 507=M+1.

N-(3-Cyano-1-cyclohexyl-pyrrolidin-3-yl)-2-indan-2-ylmethyl-4-morpholin-4-yl-4-oxo-butyramide; MS, m/z 493=M+1.

N-(3-Cyano-1-cyclohexyl-pyrrolidin-3-yl)-2-cyclopentylmethyl-4-morpholin-4-yl-4-oxo-butyramide; MS, m/z 445=M+1.

Example 15

[2-Cyano-2-(2-cyclohexylmethyl-4-morpholin-4-yl-4-oxo-butrylamino)-ethyl]-carbamic acid tert-butyl ester

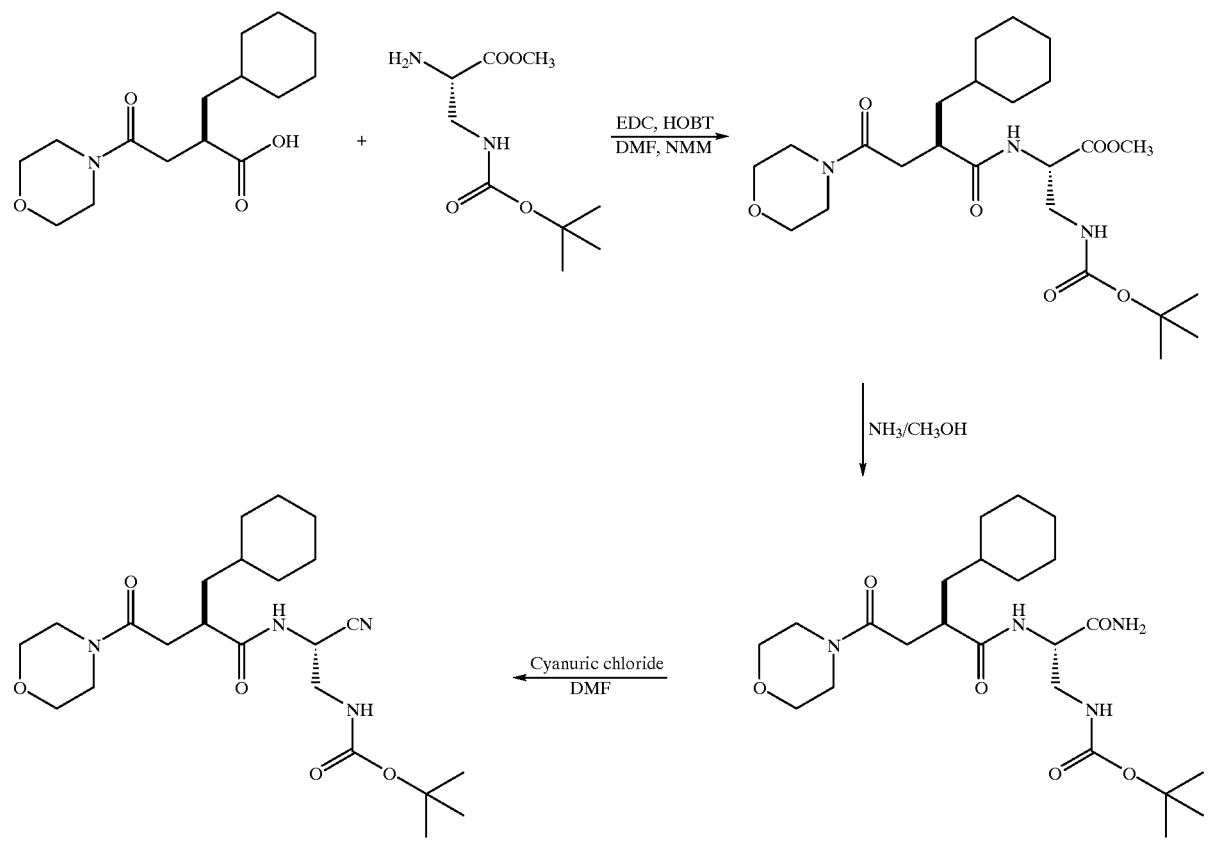

(a) 3-tert-Butoxycarbonylamino-2-(2-cyclohexylmethyl-4-morpholin-4-yl-4-oxo-butyrylamino)-propionic acid methyl ester was prepared by the procedure described in Example 1 from (R)-2-cyclohexylmethyl-4-morpholin-4-yl-4-oxo-butyric acid (0.25 g, 0.88 nmmol), EDC (0.22 g, 1.15 mmol), 1-hydroxybenzotriazole (0.155 g, 0.1.15 mmol) and the HCl salt of N-Beta-Boc-Alpha-Beta-Diaminopropionic acid methyl ester (0.25 g, 0.98 mmol) to yield a white solid (0.36 g, 84.5%) after purification by flash column chromatography. MS: m/z 484=M+1.

(b) The above product (0.36 g, 0.745 mmol) was dissolved in 25 mL of 2M ammonia in MeOH. The reaction was cooled to 5° C. and saturated with ammonia. The reaction was stoppered and left at room temperature overnight. The volatiles were removed to give the corresponding amide[2-Carbamoyl-2-(2-cyclohexylmethyl-4-morpholin-4-yl-4-oxo-butyrylamino)-ethyl]-carbamic acid tert-butyl ester (0.34 g, 97.5%). MS: m/z 469=M+1.

(c) The amide from the step above (0.050 g, 0.107 mmol) and cyanuric chloride (0.020, 0.108 mmol) were reacted as described by the procedure in Example 1. The residue was purified by chromatography (SiO$_2$, 5% MeOH in CH$_2$Cl$_2$) to give the title compound as a white solid (0.02, 48%); $^1$H NMR (CDCl$_3$) 6.83–6.81(1H, d), 5.49(1H, m), 4.93(1H, s), 3.68–3.44(8H, m), 2.79–2.73(2H, m), 2.32(1H, d), 1.7–1.59 (8H, m), 1.44(9H,s), 1.25–1.11(4H, m), 0.89–0.86(3H, m). MS: m/z 451=M+1.

Example 16

N-{Cyano-[(cyclohexyl-ethyl-amino)-methyl]-methyl}-2-cyclohexylmethyl-4-morpholin-4-yl-4-oxo-butyramide

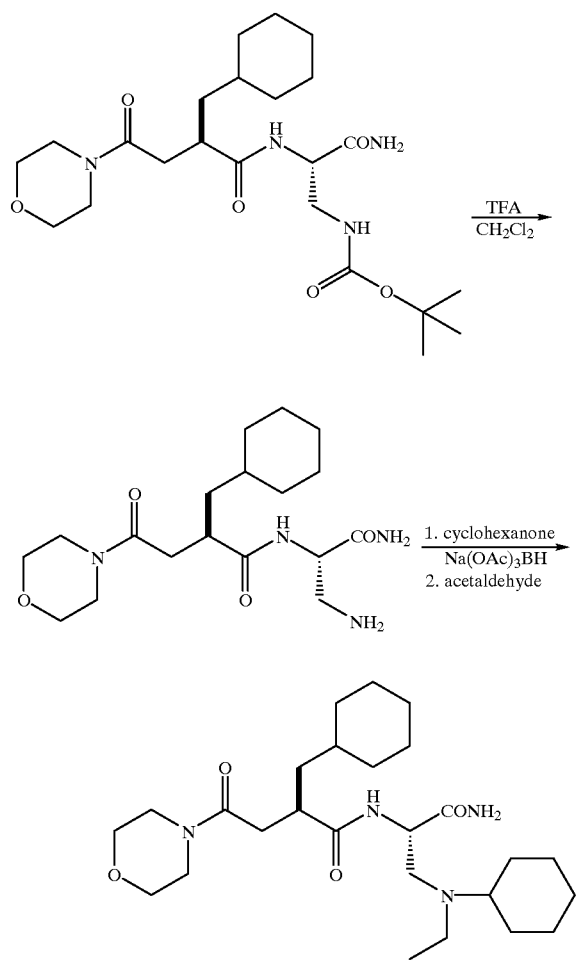

-continued

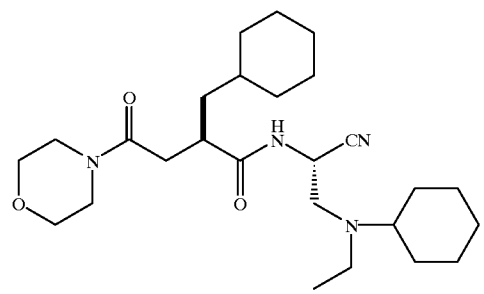

(a) To [2-Carbamoyl-2-(2-cyclohexylmethyl-4-morpholin-4-yl-4-oxo-butyrylamino)-ethyl]-carbamic acid tert-butyl ester (0.15 g, 0.32 mmol) in 5 mL methylene chloride at room temperature was added 0.5 mL of TFA. The reaction was stirred for 1 h and the volatiles removed. The residue was used for the next step without further purification. MS: m/z=369 M+1.

(b) To the above N-(2-Amino-1-carbamoyl-ethyl)-2-cyclohexylmethyl-4-morpholin-4-yl-4-oxo-butyramide TFA salt (0.154 g, 0.32 mmol) in 10 mL THF was added cyclohexanone (0.62 g, 0.64 mmol). The reaction was cooled to 0° C. and sodium triacetoxyborohydride was added (0.176 g, 0.83 mmol) and the reaction was allowed to warm up to room temperature overnight. The reaction mixture was cooled in an ice bath and acetaldehyde (0.1 mL, excess) was added. The ice bath was removed and the reaction was stirred for 2 h. The reaction was quenched with saturated sodium bicarbonate solution, extracted with EtOAc and dried over anhydrous sodium sulfate. The volatiles were removed and the crude product was purified by flash column chromatography (SiO$_2$, 5% MeOH in CH$_2$Cl$_2$) to give the desired product (0.1 g, 65.5%). MS: m/z=479 M+1.

(c) The amide from the step above (0.070 g, 0.146 mmol) and cyanuric chloride (0.054 g, 0.292 mmol) were reacted as described by the procedure in Example 1. The residue was purified by chromatography (SiO$_2$, 5% MeOH in CH$_2$Cl$_2$) to give the title compound as a white solid (0.035 g, 51.9%); $^1$H NMR (CDCl$_3$), 4.64–4.59(1H, m), 3.66–3.62(6H, m), 3.56(2H, m), 3.45(2H, m), 2.86–2.7(5H, m), 2.62(2H, m), 2.5(1H, m), 2.3(1H, m), 1.78(6H, m), 1.6(5H, 1m), 1.26(6H, m), 1.1(3H, t), 0.85(3H, m). MS: m/z=461 M+1.

The following compound was synthesized using the above procedure:

N-{Cyano-[(dibenzylamino)-methyl]-methyl}-2-cyclohexylmethyl-4-morpholin-4-yl-4-oxo-butyramide, MS: m/z=531 M+1

Example 17

N-{[(Benzyl-ethyl-amino)-methyl]-cyano-methyl}-2-cyclohexylmethyl-4-morpholin-4-yl-4-oxo-butyramide

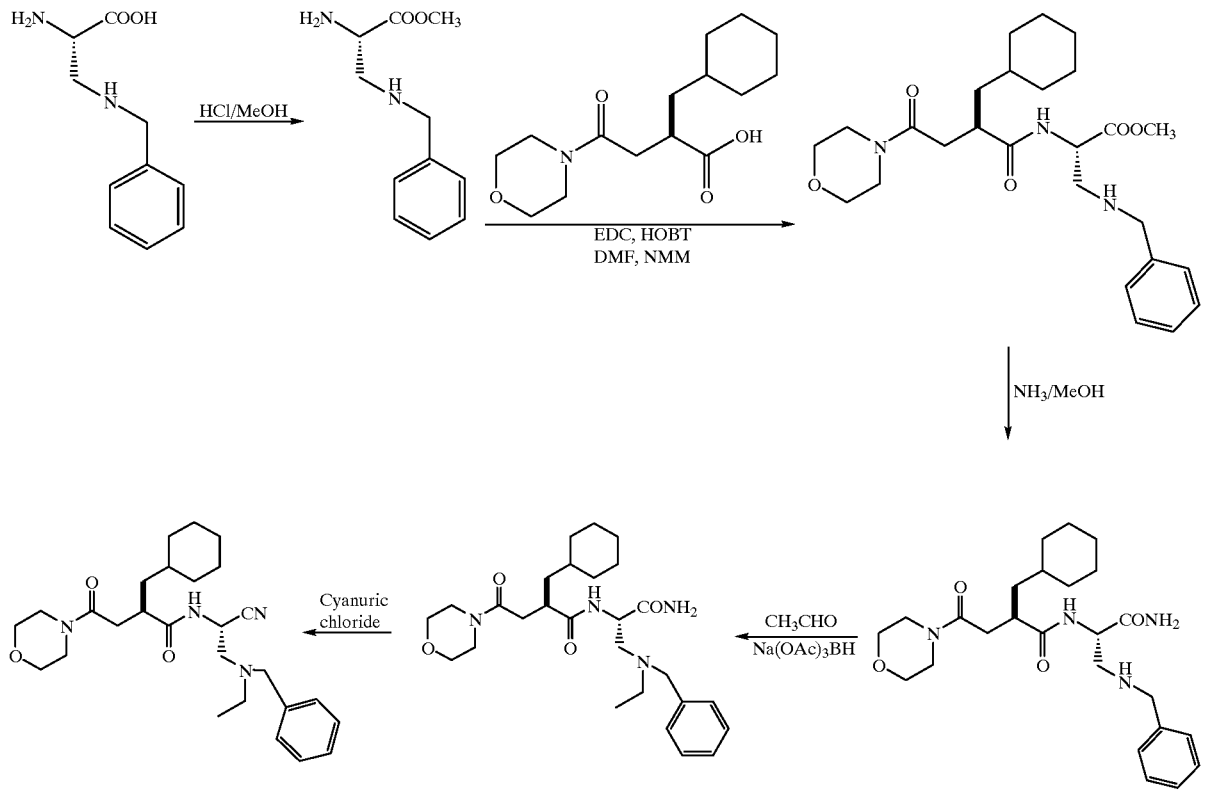

(a) To 1N HCl/MeOH (50 mL) at 0° C. was added (S)-2-Amino-3-benzylamino-propanoic acid (0.5 g, 2.57 mmol). Reaction was stirred at room temperature overnight. Volatiles were removed to give the product 2-Amino-3-benzylamino-propanoic acid methyl ester dihydrochloride salt as a white solid (0.7 g, 97.5%). MS: m/z=209 M+1.

(b) The title compound was synthesized according to the scheme using the procedures in Example 2. The diastereomers were separated via flash column chromatography to give N-{[(Benzyl-ethyl-amino)-methyl]-cyano-methyl}-2-cyclohexylmethyl-4-morpholin-4-yl-4-oxo-butyramide, MS: m/z=469 M+1.

Example 18

N-(Cyano-piperidin-1-ylmethyl-methyl)-2-cyclohexylmethyl-4-morpholin-4-yl-4-oxo-butyramide

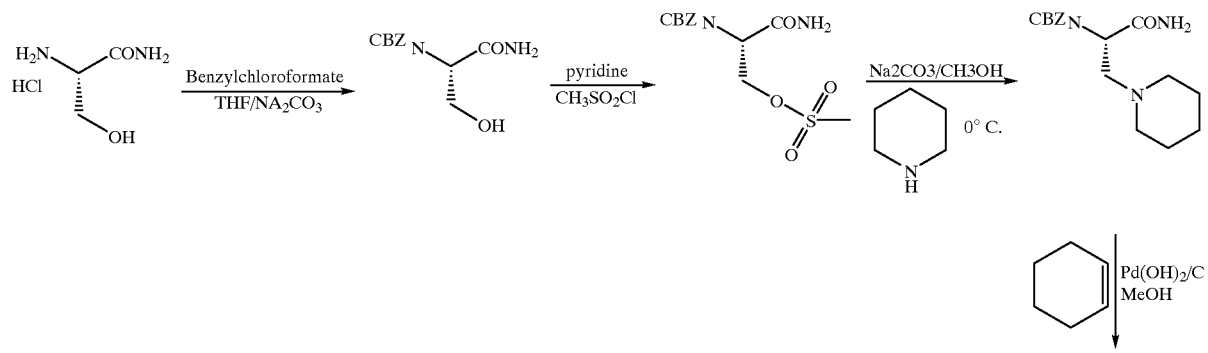

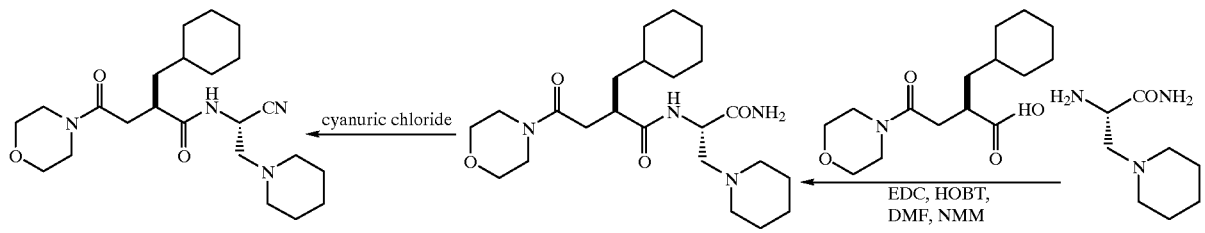

(a) To sodium carbonate (1.13 g, 10.67 mmol) in water (10 mL) and THF (15 mL) at 0° C. was added L-serine amide hydrochloride (1.0 g, 7.1 mmol). The reaction was stirred for 5 min and then benzyl chlorofornate was added (1.2 g, 7.1 mmol). The reaction was allowed to warm up to room temperature and stirred for 4 h. Volatiles were removed and the residue was extracted with methylene chloride/EtOAc (2:1). The organic fraction was dried over anhydrous sodium sulfate and evaporated to give the CBz protected serine amide as a white solid (1.0 g, 59%). NMR and MS were consistent with the desired product.

(b) To the above CBz protected serine amide (0.5 g, 2.1 mmol) in dry pyridine (3 mL) at 0° C. was added methanesulfonyl chloride (0.2 mL, 2.52 mmol) dropwise. After addition was complete, the reaction was stirred for 2 h at 0° C. It was poured over 10 mL of cold aqueous 1N HCl and extracted with EtOAc (2×25 mL). The combined organic fractions were washed with saturated sodium bicarbonate, brine and dried over anhydrous sodium sulfate. Removal of volatiles afforded the desired product as a white solid (0.6 g, 90.5%). NMR and MS were consistent with the desired product.

(c) The above mesylate (0.4 g, 1.26 mmol) was dissolved in MeOH (8 mL) at 0° C. and to this was added sodium carbonate (0.13 g, 1.26 mmol) and piperidine (0.11 g, 1.26 mmol). The reaction was stirred at 0° C. for 6 h. Solvent was removed and the residue was extracted with EtOAc. The solid was filtered off, filtrate evaporated and purified by flash column chromatography (Silica gel, 5%$CH_3OH/CH_2Cl_2$). The desired piperidine serine amide was obtained as a white solid (0.3 g, 77%). NMR and MS consistent with desired product. MS: m/z=306 M+1.

(d) The above piperidine compound (0.09 g, 0.29 mmol) was dissolved in MeOH (15 mL) and subjected to transfer hydrogenation using cyclohexene (3 mL) and palladium hydroxide on carbon (0.020 g). The reaction was heated at 70° C. for 45 min., cooled and filtered over diatomaceous earth. Removal of solvent gave the free amine (0.04 g, 79.3%). NMR and MS consistent with desired product. MS: m/z=172 M+1.

(e) The above amine was further coupled and then dehydrated using conditions described in Example 2, giving the target compound: N-(Cyano-piperidin-1-ylmethyl-methyl)-2-cyclohexylmethyl-4-morpholin-4-yl-4-oxo-butyramide, $^1$H NMR (CDCl$_3$) m), 4.75(1H, m), 3.67(5H, m), 3.55(2H, m), 3.44(1H, m), 2.7(3H, m), 2.57(2H,m), 2.45(2H, m), 2.31(1H, m), 1.7(6H, m), 1.4(3H, m), 1.2(8H, m), 0.89(3H, m). MS: m/z=419 M+1.

Example 19

N-(1-Benzyl-3-cyano-pyrrolidin-3-yl)-2-cyclohexylmethy-4-(3-methanesulfonylamino-pyrrolidin-1-yl)-4-oxo-butyramide N-(1-Benzyl-3-cyano-pyrrolidin-3-yl)-2-cyclohexylmethyl-4-(3-methanesulfonylamino-pyrrolidin-1-yl)-4-oxo-butyramide was prepared via a slight modification of Example 6. A 3-tert-butoxycarbonyl amino pyrrolidine was coupled to (R)-2-cyclohexyl methyl succinic acid 1-methyl ester. The Boc protecting group was removed with HCl/dioxane and the resulting amino pyrrolidine was alkylated with methanesulfonyl chloride. This intermediate was then carried through the standard synthetic sequence outlined in Example 6 to give the title compound; MS: m/z=544.4 M+1.

The following compound was synthesized using the above procedure:

N-(3-Cyano-1-cyclohexyl-pyrrolidin-3-yl)-2-cyclohexylmethyl-4-(3-methanesulfonylamino-pyrrolidin-1-yl)-4-oxo-butyramide. MS: m/z=536.4 M+1.

Example 20

N-[(3R)-3-Cyano-1-(3,3-dimethyl-cyclohexyl)-pyrrolidin-3-yl]-(2R)-2-cyclohexylmethyl-4-morpholin-4-yl-1-oxo-butyramide

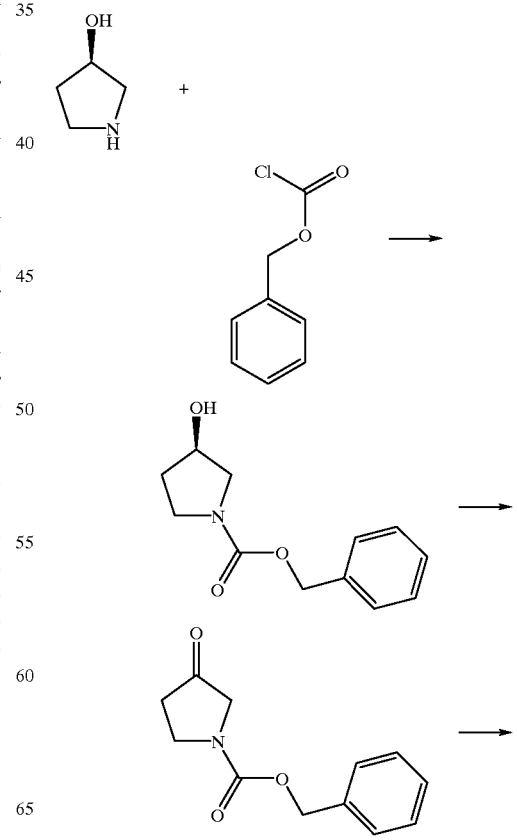

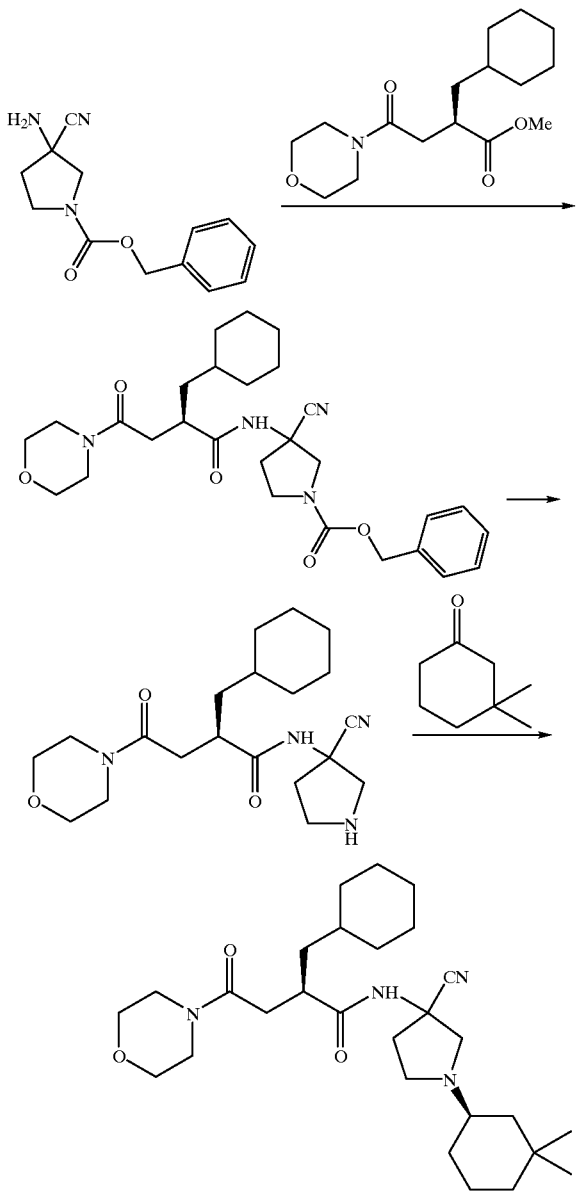

(a) N-Benzyloxycarbonyl-(R)-3-hydroxypyrrolidine

To a stirred mixture of (R)-3-hydroxypyrrolidine (4.35 g, 50 mmol) in THF (50 mL) and aqueous sodium carbonate (10.6 g, 100 mmol in 50 mL water) cooled to 0° C. was added a solution of benzyl chloroformate in THF (60 mmol, 8.6 mL in 10 mL THF) over a period of 5–10 min. After stirring at 0° C. for 2 h, the reaction mixture was diluted with 200 mL water and extracted with methylene chloride (3×100 mL). The combined extracts were washed with 1N sulfuric acid (3×75 mL) followed by brine solution (3×50 mL). This extract was then dried over anhydrous sodium sulfate and the solvent evaporated to give a light yellow oil (10.5 g, 95% yield) which was used for the next reaction without any purification.

(b) (3R)-3-Cyano-3-(2-cyclohexylmethyl-4-morpholin-4yl-4-oxo-butyrylamino)-pyrrolidine-1-carboxylic acid benzyl ester The title compound was prepared using the procedures outlined in Example 6 and the intermediate generated from step a. above.

(c) Hydrogenolysis of (3R)-3-cyano3-(2-cyclohexylmethyl-4-morpholin-4-yl-4-oxo-butyrylamino)-pyrrolidine-1-carboxylic acid benzyl ester A solution of the CBZ-compd., (1.8 g, 3.53 mmol) in EtOH (75 mL) was stirred under an atmosphere of hydrogen gas along with 10% palladium-carbon (0.3 g). After 1 h catalyst was filtered through a diatomaceous earth and the solvent evaporated to give a thick colorless oil (1.26 g, 95%) and was used without purification.

(d) Reductive Amination

To a stirred solution of the amine (0.3 mmol, 113 mg) and the 3,3-dimethylcyclohexanone (1 mmol, 126 mg) in 1,2-dichloroethane (1 mL) was added sodium triacetoxyborohydride (0.3 mmol, 66 mg). After 2 h the reaction mixture was diluted with 10 mL methylene chloride, washed with water (3×5 mL) and the solvent was evaporated from the organic layer to give a colorless oil which was taken up in 50% aqueous acetonitrile and purified by reverse phase hplc. The later eluting peak was characterized to be N-[(3R)-3-cyano-1-(3,3-dimethyl-cyclohexyl)-pyrrolidin-3-yl]-(2R)-2-cyclohexylmethyl-4-morpholin-4-yl-4-oxo-butyramide; (MH+487, $^1$H NMR (DMSO-d6) 0.5–1.7 (27H, m), 1.9–2.6 (8H, m), 2.6,2.85 (1H, dd), 3 (1H, d), 3.15–3.34 (8H, m), 8.45 (1H, s).

The following compounds were synthesized using the above procedure:

N-[(3S)-3-Cyano-1-trans-(4-ethyl-cyclohexyl)-pyrrolidin-3-yl]-(2R)-2-cyclohexylmethyl-4-morpholin-4-yl-4-oxo-butyramide N-[(3R)-3-Cyano-1-trans-(4-ethyl-cyclohexyl)-pyrrolidin-3-yl]-(2R)-2-cyclohexylmethyl-4-morpholin-4-yl-4-oxo-butyramide N-[(3S)-3-Cyano-1-cis-(4-ethyl-cyclohexyl)-pyrrolidin-3-yl]-(2R)-2-cyclohexylmethyl-4-morpholin-4-yl-4-oxo-butyramide N-[(3R)-3-Cyano-1-cis-(4-ethyl-cyclohexyl)-pyrrolidin-3-yl]-(2R)-2-cyclohexylmethyl-4-morpholin-4-yl-4-oxo-butyramide N-[(3S)-3-Cyano-1-trans-(4-isopropyl-cyclohexyl)-pyrrolidin-3-yl]-(2R)-2-cyclohexylmethyl-4-morpholin-4-yl-4-oxo-butyramide N-[(3R)-3-Cyano-1-trans-(4-isopropyl-cyclohexyl)-pyrrolidin-3-yl]-(2R)-2-cyclohexylmethyl-4-morpholin-4-yl-4-oxo-butyramide N-[(3S)-3-Cyano-1-cis-(4-isopropyl-cyclohexyl)-pyrrolidin-3-yl]-(2R)-2-cyclohexylmethyl-4-morpholin-4-yl-4-oxo-butyramide N-[(3R)-3-Cyano-1-cis-(4-isopropyl-cyclohexyl)-pyrrolidin-3-yl]-(2R)-2-cyclohexylmethyl-4-morpholin-4-yl-4-oxo-butyramide N-[1-trans-(4-tert-Butyl-cyclohexyl)-(3S)-3-cyano-pyrrolidin-3-yl]-(2R)-2-cyclohexylmethyl-4-morpholin-4-yl-4-oxo-butyramide N-[1-trans-(4-tert-Butyl-cyclohexyl)-(3R)-3-cyano-pyrrolidin-3-yl]-(2R)-2-cyclohexylmethyl-4-morpholin-4-yl-4-oxo-butyramide N-[1-cis-(4-tert-Butyl-cyclohexyl)-(3S)-3-cyano-pyrrolidin-3-yl]-(2R)-2-cyclohexylmethyl-4-morpholin-4-yl-4-oxo-butyramide N-[1-cis-(4-tert-Butyl-cyclohexyl)-(3R)-3-cyano-pyrrolidin-3-yl]-(2R)-2-cyclohexylmethyl-4-morpholin-4-yl-4-oxo-butyramide N-[(3S)-3-cyano-1-cis-(3-methyl-cyclohexyl)-pyrrolidin-3-yl]-(2R)-2-cyclohexylmethyl-4-morpholin-4-yl-4-oxo-butyramide N-[(3R)-3-cyano-1-cis-(3-methyl-cyclohexyl)-pyrrolidin-3-yl]-(2R)-2-cyclohexylmethyl-4-morpholin-4-yl-4-oxo-butyramide N-[(3S)-3-cyano-1-trans-(3-methyl-cyclohexyl)-pyrrolidin-3-yl]-(2R)-2-cyclohexylmethyl-4-morpholin-4-yl-4-oxo-butyramide N-[(3R)-3-cyano-1-trans-(3-methyl-cyclohexyl)-pyrrolidin-3-yl]-(2R)-2-cyclohexylmethyl-4-morpholin-4-yl-4-oxo-butyramide N-[(3S)-3-Cyano-1-(3,3-dimethyl-cyclohexyl)-pyrrolidin-3-yl]-(2R)-2-cyclohexylmethyl-4-morpholin-4-yl-4-oxo-butyramide N-[(3R)-3-Cyano-1-(3,3-dimethyl-cyclohexyl)-pyrrohdin-3-yl]-(2R)-2-cyclohexylmethyl-4-morpholin-4-yl-4-oxo-butyramide N-[(3S)-3-Cyano-1-cis-(3-isopropyl-cyclohexyl)-pyrrolidin-3-yl]-(2R)-2-cyclohexylmethyl-4-morpholin-4-yl-4-oxo-butyramide N-[(3R)-3-Cyano-1-cis-(3-isopropyl-cyclohexyl)-pyrrolidin-3-yl]-(2R)-2-cyclohexylmethyl-4-morpholin-4-yl-4-oxo-butyramide N-[(3S)-3-Cyano-1-trans-(3-isopropyl-cyclohexyl)-pyrrolidin-3-yl]-(2R)-2-cyclohexylmethyl-4-morpholin-4-yl-4-oxo-butyramide N-[(3R)-3-Cyano-1-trans-(3-isopropyl-cyclohexyl)-pyrrolidin-3-yl]-(2R)-2-cyclohexylmethyl-4-morpholin-4-yl-4-oxo-butyramide N-[(3S)-3-Cyano-1-cis-(2-methyl-cyclohexyl)-pyrrolidin-3-yl]-(2R)-2-cyclohexylmethyl-4-morpholin-4-yl-4-oxo-butyramide N-[(3R)-3-Cyano-1-cis-(2-methyl-cyclohexyl)-pyrrolidin-3-yl]-(2R)-2-cyclohexylmethyl-4-morpholin-4-yl-4-oxo-butyramide N-[(3S)-3-Cyano-1-trans-(2-methyl-cyclohexyl)-pyrrolidin-3-yl]-(2R)-2-cyclohexylmethyl-4-morpholin-4-yl-4-oxo-butyramide N-[(3R)-3-Cyano-1-trans-(2-methyl-cyclohexyl)-pyrrolidin-3-yl]-(2R)-2-cyclohexylmethyl-4-morpholin-4-yl-4-oxo-butyramide N-[(3S)-3-Cyano-1-cis-(2-ethyl-cyclohexyl)-pyrrolidin-3-yl]-(2R)-2-cyclohexylmethyl-4-morpholin-4-yl-4-oxo-butyramide N-[(3R)-3-Cyano-1-cis-(2-ethyl-cyclohexyl)-pyrrolidin-3-yl]-(2R)-2-cyclohexylmethyl-4-morpholin-4-yl-4-oxo-butyramide N-[(3S)-3-Cyano-1-trans-(2-ethyl-cyclohexyl)-pyrrolidin-3-yl]-(2R)-2-cyclohexylmethyl-4-morpholin-4-yl-4-oxo-butyramide N-[(3R)-3-Cyano-1-trans-(2-ethyl-cyclohexyl)-pyrrolidin-3-yl]-(2R)-2-cyclohexylmethyl-4-morpholin-4-yl-4-oxo-butyramide N-[(3S)-3-Cyano-1-(2,2-dimethyl-cyclohexyl)-pyrrolidin-3-yl]-(2R)-2-cyclohexylmethyl-4-morpholin-4-yl-4-oxo-butyramide N-[(3R)-3-Cyano-1-(2,2-dimethyl-cyclohexyl)-pyrrolidin-3-yl]-(2R)-2-cyclohexylmethyl-4-morpholin-4-yl-4-oxo-butyramide N-[(3S)-3-Cyano-1-(4,4-dimethyl-cyclohexyl)-pyrrolidin-3-yl]-(2R)-2-cyclohexylmethyl-4-morpholin-4-yl-4-oxo-butyramide N-[(3R)-3-Cyano-1-(4,4-dimethyl-cyclohexyl)-pyrrolidin-3-yl]-(2R)-2-cyclohexylmethyl-4-morpholin-4-yl-4-oxo-butyramide Example 21

N-(2-Benzyloxymethyl-1-cyano-cyclopropy)-cyclohexylmethyl-4-morpholin-4-yl-4-oxo-butyramide

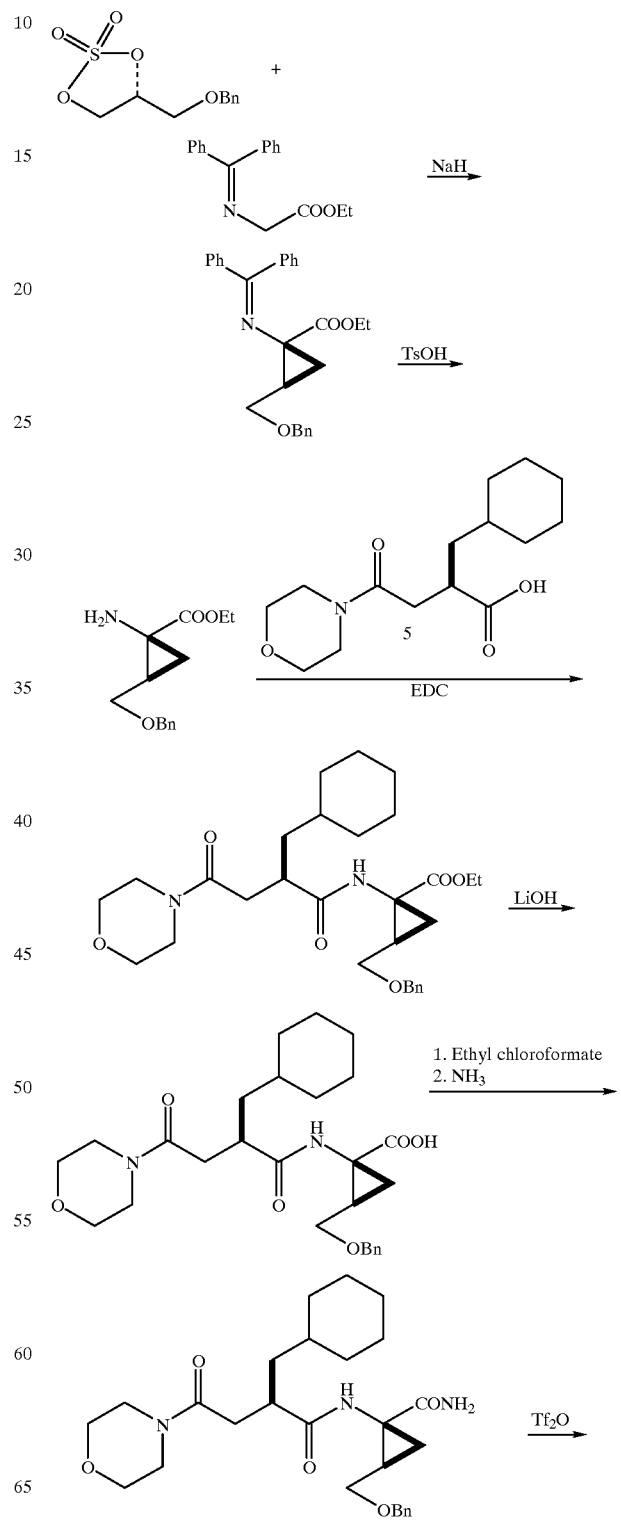

103
-continued

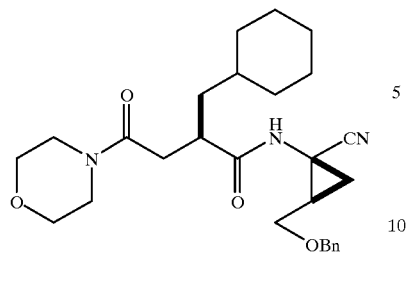

To a stirred mixture of NaH (60% dispersion in mineral oil, 35.9 g, 149.5 mmol) in DME (100 mL) at 0° C., was added a solution of 4-benzyloxymethyl-[1,3,2]-dioxathiolane-2,2-dioxide (K. Burgess et al., *J. Org. Chem.* 1993, 58, 3767–3768) (17.4 g, 71.2 mmol) and (benzhydrylidene-amino)acetic acid ethyl ester (19.0 g, 71.2 mmol) in DME (100 mL). The mixture was warmed to 55° C. (30 min later, the mixture turned to solid and thus 200 mL of DME was added) and stirred for 4 h. It was allowed to cool to room temperature, slowly poured onto ice in saturated aqueous ammonium chloride solution, extracted with dichloromethane, washed with brine, dried (sodium sulfate) and concentrated to give crude ester product.

A mixture of the above ester and p-toluenesulfonic acid monohydrate (13.5 g, 71.2 mmol) in MeOH (170 mL) and water (25 mL) was stirred at room temperature for 1 h. It was diluted with water, extracted with dichloromethane, washed with brine, dried (sodium sulfate) and purified by flash chromatography on silica gel (4 hexane/1 EtOAc) to give the desired amino ester (11.0 g, 61.9% in two steps).

Typical peptide coupling of the above amino ester with (R)-2-cyclohexylmethyl-4-morpholin-4-yl-4-oxo-butyric acid gave the desired coupled product in 50% yield.

A mixture of the above intermediate (13.1 g, 25.5 mmol) and lithium hydroxide (1.2 g, 2 equiv.) in MeOH (100 mL) and water (30 mL) was stirred at room temperature overnight. It was diluted with 1N HCl, extracted with dichloromethane, washed with brine, dried (sodium sulfate) and concentrated to dryness to give the desired carboxylic acid (10.6 g, 86%).

To a stirred solution of the above acid (11.3 g, 23.3 mmol) in THF (50 mL) at −10° C. was added triethylamine (3.9 mL, 1.2 equiv.) and ethyl chloroformate (2.7 mL, 1.2 equiv.). 20 Min later, ammonia gas was bubbled through the reaction for 4 h at −20° C. The reaction was allowed to warm to room temperature and stirred overnight. It was concentrated and purified by flash chromatography on silica gel (dichloromethane/MeOH=10/1) to give the desired amide (11.3 g, 100%).

To a stirred solution of the above amide (178 mg, 0.36 mmol) and triethylamine (150 ul, 3 equiv.) in dichloromethane (10 mL) at 0° C. was added Tf$_2$O. The mixture was allowed to warm to room temperature and stirred for 20 min. It was washed with brine, dried (sodium sulfate) and purified by chromatography on silica gel (hexane/ethyl acetate=1/1) to give the title compound (30 mg, 17.8%).

104

Example 22

N$^1$-(1-Cyano-2dimethylaminomethyl-cyclopropyl)-2-cyclohexylmethyl-N$^4$-ethyl-N$^4$-(2-methoxy-ethyl-succinamide

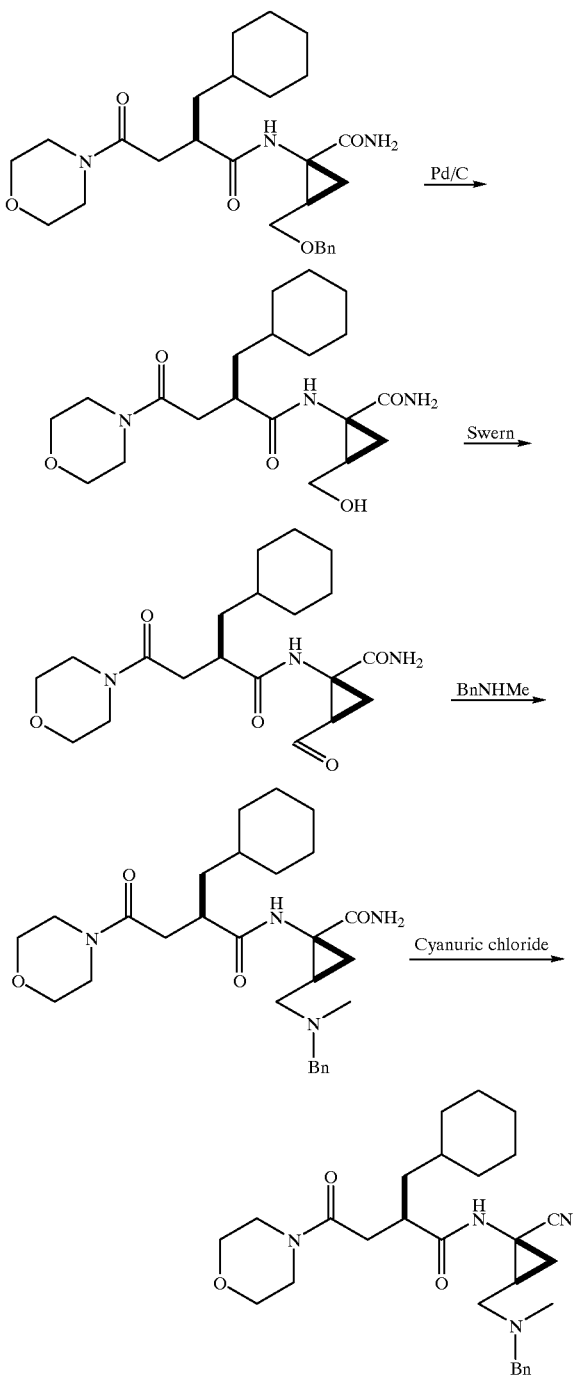

A mixture of the intermediate amide from Example 21 (10 g, 20.6 mmol) and Pd/C (10%, 3 g) in MeOH (150 mL) was shaken under H$_2$ in a Parr apparatus overnight and filtered. The filtrate was concentrated to dryness to give the desired alcohol (7.8 g, 95.8%).

To a stirred solution of oxalyl chloride (2 M in dichloromethane, 7.6 mL, 15.2 mmol) in dichloromethane (30 mL) at −78° C. was added DMSO (2.2 mL, 31 mmol) dropwise. A solution of the above alcohol (6 g, 15.1 mmol) in dichloromethane (30 mL) was added. The mixture was allowed to warm to −40° C. in 1 h before triethylamine (8.5 mL, 61 mmol) was added. The mixture was then warmed to room temperature, washed with water and brine, dried (sodium sulfate) and concentrated to dryness to give the desired aldehyde (5.5 g, 92%).

A mixture of the aldehyde from above (1 g, 2.5 mmol), N-benzylmethylamine (0.33 mL, 2.5 mmol) and sodium triacetoxyborohydride (0.81 g, 1.5 equiv.) in dichloromethane (10 mL) was stirred at room temperature overnight. The reaction mixture was washed with water, saturated aqueous ammonium chloride and brine, dried (sodium sulfate) and purified by flash chromatography on silica gel (dichloromethane/MeOH=10/1) to give the desired benzyl methylamine (0.84 g, 66.8%).

A solution of the above amine (478 mg, 0.95 mmol) and cyanuric chloride (353 mg, 2 equiv.) in DMF (4 mL) was stirred at room temperature for 1 h. The reaction mixture was diluted with water, extracted with dichloromethane, washed with brine, dried (sodium sulfate) and purified by flash chromatography on silica gel (dichloromethane/MeOH=20/1) to give the title compound (180 mg, 37.4%).

Example 23

N-(1-Cyano-2-hydroxymethyl-cylogropyl)-2-cyclohexylmethyl-4-morpholin-4-yl-4-oxo-butyramide

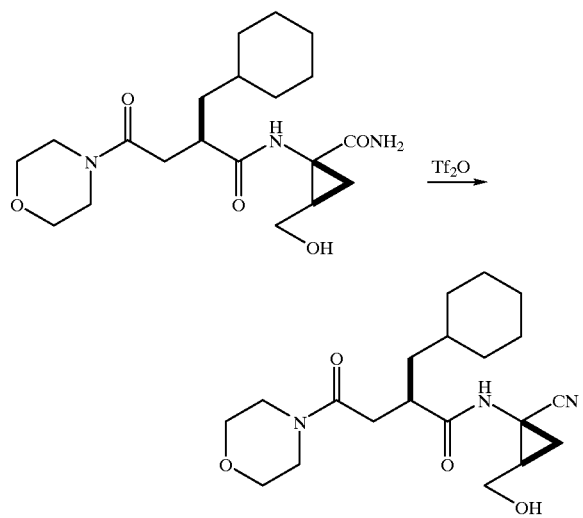

To a stirred solution of the intermediate alcohol from Example 22 (1.1 g, 2.7 mmol) and pyridine (0.44 mL, 5.2 mmol) in dichloromethane (15 mL) at 0° C. was added Tf$_2$O (0.67 mL, 4 mmol) slowly. The mixture was allowed to warm to room temperature and stirred for 1 h. The reaction mixture was washed with brine, dried (sodium sulfate) and purified by chromatography on silica gel (dichloromethane/MeOH=20/1) to give the title compound (0.35 g, 34.6%).

Methods of Therapeutic Use

The compounds of the invention are useful in inhibiting the activity of cathepsin S, K, F, L and cathepsin B. In doing so, these compounds are useful in blocking disease processes mediated by these cysteine proteases.

Compounds of this invention effectively block degradation of the invariant chain to CLIP by cathepsin S, and thus inhibit antigen presentation and antigen-specific immune responses. Control of antigen specific immune responses is an attractive means for treating autoimmune diseases and other undesirable T-cell mediated immune responses. Thus, there is provided methods of treatment using the compounds of this invention for such conditions. These encompass autoimmune diseases and other diseases involving inappropriate antigen specific immune responses including, but not limited to, rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, atopic dermatitis, insulin-dependent diabetes mellitus and asthma. The compounds of the invention can also be used to treat other disorders associated with extracellular proteolysis such as Alzheimer's disease and atherosclerosis. The compounds of the invention can also be used to treat other disorders associated with inappropriate autoimmune responses, T-cell mediated immune responses, or extracellular proteolysis mediated by cathepsin S, unrelated to those listed above or discussed in the Background of the Invention. Therefore, the invention also provides methods of modulating an autoimmune disease comprising administering to a patient in need of such treatment a pharmaceutically effect amount of a compound according to the invention.

Compounds of the invention also include inhibition of cathepsin K. In doing so, they may block inappropriate degradation of bone collagen and other bone matrix proteases. Thus, there is provided a method for treating diseases where these processes play a role such as osteoporosis. Inhibition of cathepsins F, L and B are also within the scope of the invention due to similarity of the active sites in cysteine proteases as described above.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of formulas (I) or (Ia) (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forns and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Assessment of Biological Properties

Expression and Purification of Recombinant Human Cathepsin S

Cloning of human cathepsin S:

U937 RNA was subjected to reverse transcriptase/polymerase chain reaction with primer A (5'cacaatgaaacggctggtttg 3') and primer B (5'ctagatttctgggtaagaggg 3') designed to specifically amplify the cathepsin S cDNA. The resulting 900 bp DNA fragment was subcloned into pGEM-T (Promega) and sequenced to confirm its identity. This construct was used for all subsequent manipulations. This procedure is typical for cloning of known genes and is established in its field.

Human Pre-Pro-Cat S was removed from pGem-T vector (Promega, 2800 Woods Hollow Rd, Madison, Wis. 53711) by digestion with restriction enzyme SacII, followed by treatment with T4 DNA polymerase to generate a blunt end, and a second restriction enzyme digest with SalI. It was subcloned into pFastBac1 donor plasmid (GibcoBRL, 8717 Grovemont Cr., Gaithersburg, Md. 20884) which had been cut with restriction enzyme BamH1 and blunt-ended and then cut with restriction enzyme SalI. The ligation mixture was used to transform DH5a competent cells (GibcoBRL) and plated on LB plates containing 100 ug/ml ampicillin. Colonies were grown in overnight cultures of LB media containing 50 ug/ml Ampicillin, plasmid DNA isolated and correct insert confirmed by restriction enzyme digestion. Recombinant pFastBac donor plasmid was transformed into DH10Bac competent cells (GibcoBRL). Large white colonies were picked from LB plates containing 50 ug/ml kanamycin, 7 ug/ml gentamicin, 10 ug/ml tetracycline, 100 ug/ml Bluo-gal, and 40 ug/ml IPTG. DNA was isolated and used to transfect Sf9 insect cells using CellFECTIN reagent (GibcoBRL). Cells and supernatant were harvested after 72 hours. Viral supernatant was passaged twice and presence of Cat S confirmed by PCR of the supernatant.

SF9 cells were infected with recombinant baculovirus at a MOI of 5 for 48–72 hrs. Cell pellet was lysed and incubated in buffer at pH 4.5 at 37 for 2 hours to activate Cat S from pro-form to active mature form (Bromme, D & McGrath, M., *Protein Science,* 1996, 5:789–791.) Presence of Cat S was confirmed by SDS-PAGE and Western blot using rabbit anti-human proCat S.

Inhibition of Cathepsin S

Human recombinant cathepsin S expressed in Baculovirus is used at a final concentration of 10 nM in buffer. Buffer is 50 mM Na Acetate, pH 6.5, 2.5 mMEDTA, 2.5 mMTCEP. Enzyme is incubated with either compound or DMSO for 10 min at 37 C. Substrate 7-amino-4-methylcoumarin, CBZ-L-valyl-L-valyl-L-arginineamide (custom synthesis by Molecular Probes) is diluted to 20 uM in water (final concentration of 5 uM), added to assay and incubated for additional 10 minutes at 37 C. Compound activity is measured by diminished fluorescence compared to DMSO control when read at 360 nm excitation and 460 nm emission.

Examples listed above were evaluated for inhibition of cathepsin S in the above assay. All had $IC_{50}$ values of 100 micromolar or below.

Inhibition of Cathepsin K, F, L and B

Inhibition of these enzymes by particular compounds of the invention may be determined without undue experimentation by using art recognized methods as provided hereinbelow each of which is incorporated herein by reference:

Cathepsin B, and L assays are to be found in the following references:

1. Methods in Enzymology, Vol.244, Proteolytic Enzymes: Serine and Cysteine Peptidases, Alan J. Barrett, ed.

Cathepsin K assay is to be found in the following reference:

2. Bromme, D., Okamoto, K., Wang, B. B., and Biroc, S. (1996) *J. Biol. Chem.* 271, 2126–2132.

Cathepsin F assays are to be found in the following references:

3. Wang, B., Shi, G. P., Yao, P. M., Li, Z., Chapman, H. A., and Bromme, D. (1998) *J. Biol. Chem.* 273, 32000–32008.

4. Santamaria, I., Velasco, G., Pendas, A. M., Paz, A., and Lopez-Otin, C (1999) *J. Biol. Chem.* 274, 13800–13809.

Preferred compounds to be evaluated for inhibition of Cathepsin K, F, L and B in the above assays desirably have $IC_{50}$ values of 100 micromolar or below.

What is claimed is:

1. A compound of formula (I):

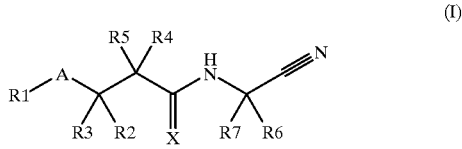

wherein:

A is —C(O)— or —CH(OR8)-;

R1 is heterocyclyl selected from the group consisting of pyrrolidinyl, piperidinyl, morpholinyl, thiomorpholinyl, piperazinyl, indolinyl, pyranyl and thiopyranyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl and amino wherein R1 is optionally substituted by one or more $R_a$;

$R_a$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl, beteroaryl selected from the group cnsisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio, arylthio, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl or phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consistng of furanyl, thienyl, pyrrolyl, oxazolyl, thiazolyl, imidazolyl, pyrazolyl, isoxazolyl, pyrazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino; $R_a$ may be further optionally substituted by one or more $R_b$;

$R_b$ is selected from the group consisting of C1–8 alkyl, C3–6 cycloalkyl, aryl, C1–8 alkoxy, aryloxy, halogen, hydroxy, oxo, carboxy, cyano, nitro, amidino and guanidino;

R2 is hydrogen, $OR_i$ or C1–5 alkyl;

R3 is hydrogen or C1–5 alkyl;

R4 is hydrogen or C1–5 alkyl;

R5 is hydrogen, C1–8 alkyl, C3–7 cycloalkyl or aryl wherein R5 is optionally substituted by one or more $R_c$;

$R_c$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, alkanoyl, aroyl, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio, arylthio, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_c$ may be further optionally substituted by one or more $R_d$;

$R_d$ is selected from the group consisting of C1–8 alkyl, C3–6 cycloalkyl, aryl, arylalkyl, C1–8 alkoxy, aryloxy, arylalkoxy, aroyl, amino, halogen, hydroxy, oxo, carboxy, cyano, nitro, amidino and guanidino;

R6 is hydrogen or lower alkyl being optionally interrupted by 1 to two heteroatoms selected from the group consisting of N,O and S;

R7 is hydrogen, C1–8 alkyl said alkyl being optionally interrupted by 1 to two heteroatoms selected from the group consisting of N,O and S, C3–7 cycloalkyl, aryl or cyano, wherein R7 is optionally substituted by one or more $R_e$;

$R_e$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, heteroarylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, triadiazolyl, pyridinyl, pyridazinyl, pyrimidinyl, pyrazinyl, indolyl, isoindolyl benzofuranyl, benzothienyl, benzimidazolyl, benzthiazolyl, purinyl, quinoinyl, isoquinolinyl, quinazolinyl, quinoxalinyl, carbazolyl, phenothiazinyl and phenoxazinyl, C1–8 alkanoylamino, aroylamino, C1–8 alkythio, arylthio, arylC1–8 alkylthio, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsufonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiormorpholinyl, piper-azinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_e$ may be further optionally substituted by one or more $R_f$;

$R_f$ is selected from the group consisting of C1–8 alkyl, C3–7 cycloalkyl, aryl optionally substituted by one or more groups selected from halogen, methyl or methoxy, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio, arylthio, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino;

or R6 and R7 together with the carbon they are attached form a 4 to 7 membered carbocyclic or heterocyclic ring, the carbocyclic or heterocyclic ring being optionally substituted with one or more $R_g$;

$R_g$ is selected from the group consisting of alkyl, cycloalkyl, phenyl, heteroaryl selected from the group consisting of furanyl, thienyl and pyridinyl, C1–5 alkanoyl, aroyl, C1–5 alkoxycarbonyl, aryloxycarbonyl, carbamoyl wherein the nitrogen atom may be independantly mono or disubstituted by C1–5 alkyl, aryl, heterocyclyl selected from the group consisting of pyrrolidinyl, piperidinyl, morpholinyl and piperazinyl or hetcroaryl selected from the group consisting of furanyl, thienyl, pyrrolyl, thiazoyl, imidazolyl, pyridinyl, benzimidazolyl and quinolinyl, C1–5 alkylthio wherein the sulfur atom may be oxidised to a sulfoxide or sulfone, arylthio wherein the sulfur atom may be oxidised to a sulfoxide or sulfone, C1–5 alkylaminosulfonyl, arylaminosulfonyl, halogen, hydroxy, oxo, carboxy and cyano, $R_g$, may be further optionally substituted by one or more $R_h$;

$R_h$ is selected from the group consisting of C1–5 alinyl, C3–6 cycloalkyl, aryl optionally substituted by one or more groups selected from halogen, C1–5 alkyl or C1–5 alkoxy, heterocyclyl selected from the group consisting of piperidinyl, morpholinyl and piperazinyl, heteroaryl selected from the group consisting of furanyl, thienyl pyrrolyl, imidazolyl, pyridinyl, pyrimidinyl, pyrazinyl, indolyl, benzimidazolyl, quinolinyl, isoquinolinyl, quinazolinyl, benzoxazolyl and quinoxalinyl, C1–5 alkoxy, aryloxy, amino wherein the nitrogen atom may be independently mono or di-substituted by alkyl, aryl, heterocyclyl selected from the group consisting of piperidinyl and morpholinyl or heteroaryl selected from the group consisting of furmanyl, thienyl and pyridinyl, halogen, hydroxy, oxo, carboxy and cyano; and R8 is hydrogen, alkyl, cycloalkyl-alkyl or arylalyl;

$R_i$ is hydrogen or C1–8 alkyl;

X is O or S.

2. The compound according to claim 1 wherein:

R1 is heterocyclyl selected from the group consisting of pyrrolidinyl, piperidinyl, morpholinyl, thiomorpholinyl, piperazinyl, indolinyl, pyranyl and thiopyranyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl or amino; wherein R1 is optionally substituted by one or more $R_a$;

$R_a$ is selected from the group consisting of C1–5 alkyl, C3–7 cycloalkyl, phenyl, naphthyl, heterocyclyl selected from the group consisting of pyrrolidinyl piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, C1–5 alkoxycarbonyl, aryloxycarbonyl, C1–5 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthio, arylthio, ureido wherein either nitrogen atom may be independently substituted by alkyl, aryl, heterocyclyl selected from the group consisting of pyrrolidinyl, piperidinyl, motrpholinyl, thiomotpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_a$ may be further optionally substituted by one or more $R_b$;

$R_b$ is selected from the group consisting of C1–5 alkyl, C3–6 cycloalkyl, aryl, C1–5 alkoxy, aryloxy, halogen, hydroxy, oxo, carboxy, cyano, nitro, amidino and guanidino;

R2 is hydrogen, $OR_i$ or C1–3 alkyl;

R3 is hydrogen or C1–3 alkyl;

R4 is hydrogen or C1–3 alkyl;

R5 is hydrogen, C1–5 alkyl, C3–7 cycloalkyl or aryl wherein R5 is optionally substituted by one or more $R_c$;

$R_c$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthio, arylthio, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl or heteroaryl selected the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, amidino and guanidino, $R_c$ may be further optionally substituted by one or more $R_d$;

$R_d$ is selected from the group consisting of C1–5 alkyl, C3–6 cycloalkyl, aryl, arylalkyl, C1–5 alkoxy, aryloxy, arylC1–5alkoxy, aroyl, amino, halogen, hydroxy, oxo, carboxy, cyano, nitro, amidino and guanidino;

R6 is hydrogen or C1–8 alkyl said alkyl being optionally interrupted by 1 to two heteroatoms selected from the group consisting of N,O and S;

R7 is hydrogen, C1–5 alkyl said alkyl being optionally interrupted by 1 to two heteroatoms selected from the group consisting of N,O and S, C3–7 cycloalkyl, aryl or cyano, wherein R7 is optionally substituted by one or more $R_e$;

$R_e$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5alkoxy, heteroarylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, qinolinyl, isoquinolinyl, quinazolinyl and quinoxalinyl, C1–5 alkanoylamino, aroylamino, C1–5 alkylthioarylthioarylC1–5 alkylthio, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_e$ may be further optionally substituted by one or more $R_f$;

$R_f$ is selected from the group consisting of C1–5 alkyl, C3–7 cycloalkyl, aryl optionally substituted by one or more groups selected from halogen, methyl or methoxy, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl C1–5 alkoxy, aryloxy, arylC1–5 alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkyltio, arylthio, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino;

or R6 and R7 together with the carbon they are attached form a carbocyclic ring selected from the group consisting of cyclopropyl, cyclobutyl, cyclopentyl and cyclohexyl or a heterocyclic ring selected from the group consisting of pyrrolidinyl, piperidinyl, hexahydropyridazinyl, hexahydropyrimidinyl, piperazinyl, pyranyl, thiopyranyl, 1,2-thiazinanyl-1,1-dioxide, 1,2,6-thiadiazinanyl-1,1-dioxide, isothiazolidinyl-1,1-dioxide and imidazolidinyl-2,4-dione, the carbocyclic or heterocyclic ring being optionally substituted with one or more $R_g$;

$R_g$ is selected from the group consisting of alkyl, cycloalkyl, phenyl, heteroaryl selected from the group consisting of furanyl and thienyl, C1–3 alkanoyl, benzoyl, C1–3 alkoxycarbonyl, carbamoyl wherein the nitrogen atom may be independantly mono or disubstituted by C1–5 alkyl, phenyl, heterocyclyl selected from the group consisting of piperidinyl, morpholinyl and piperazinyl or heteroaryl selected from the group consising of furanyl, thienyl and pyridinyl, C1–3 alkylthio wherein the sulfur atom may be oxidised to a sulfoxide or sulfone, phenylthio wherein the sulfur atom may be oxidised to a sulfoxide or sulfone, C1–5 alkylaminosulfonyl, phenylaminosulfonyl, halogen, hydroxy, carboxy and cyano, $R_g$ may be further optionally substituted by one or more $R_h$;

$R_h$ is selected from the group consisting of C1–3 alkyl, C5–6 cycloalkyl, phenyl optionally substituted by one or more groups selected from halogen, C1–3 alkyl and C1–3 alkoxy, piperidinyl, morpholinyl, piperazinyl, imidazolyl, pyridinyl, pyrimidinyl, pyrazinyl, benzimidazolyl, quinolinyl, isoquinolinyl, C1–3 alkoxy, amino wherein the nitrogen atom may be independently mono or di-substituted by C1–5 alkyl, phenyl, heterocyclyl selected from the group consisting of piperidinyl and morpholinyl or heteroaryl selected from the group consisting of furanyl, thienyl and pyridinyl, halogen, hydroxy, oxo and cyano;

R8 is hydrogen, C1–8 alkyl, C3–6 cycloalkyl-alkyl or aryl-C1–3 alkyl;

$R_i$ is hydrogen or C1–5 alkyl.

3. The compound according to claim 2 wherein:

R1 is heterocyclyl selected from the group consisting of piperidinyl, morpholinyl, thiomorpholinyl, piperazinyl, pyranyl and thiopyranyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl or amino wherein R1 is optionally substituted by one or more $R_a$;

$R_a$ is selected from the group consisting of C1–5 alyl, C3–7 cycloalkyl, phenyl, naphthyl, heterocyclyl selected from the group consisting of pyrrolidinyl, piperidinyl, morpholinyl, thiomorpholinyl, piperaznyl and indolinyl, heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, quinolinyl and isoquinolinyl, C1–5 alkoxy, aryloxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl, naphthyl, heterocyclyl selected from the group consisting of pyrrolidinyl, piperidinyl, morpholinyl, piperazinyl and indolinyl or heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio, arylthio, ureido wherein either nitrogen atom may be independently substitiated by alkyl or aryl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquiolinyl, halogen, hydroxy, oxo, carboxy, cyano and nitro, $R_a$ may be further optionally substituted by one or more $R_b$;

$R_b$ is selected from the group consisting of C1–5 alkyl, C3–6 cycloalkyl, aryl, C1–5 alkoxy, aryloxy, halogen, hydroxy, oxo, carboxy and cyano;

R2 is hydrogen, $OR_i$ or methyl;

R3 is hydrogen or methyl;

R4 is hydrogen or methyl;

R5 is C1–5 alkyl, C3–7 cycloalkyl or phenyl wherein R5 is optionaly substituted by one or more $R_c$;

$R_c$ is selected from the group consisting of C1–3 alkyl C3–6 cycloalkyl, phenyl, naphthyl, heterocyclyl selected from the group consisting of piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxy, aryloxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio, arylthio, ureido wherein either nitrogen atom may be independently substituted by C1–5 alkyl, phenyl, naphthyl, heterocyclyl selected from the group consisting of piperidinyl, morpholinyl and piperinyl or heteroaryl selected the group consisting of furanyl, thienyl, pyrrolyl, oxazolyl, thiazolyl, imidazolyl, pyridinyl, indolyl, benzofuranyl, benzothienyl, benzimidazolyl, benzthiolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consistion of furanyl, thienyl, pyrnolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_c$ may be further optionally substituted by one or more $R_d$;

$R_d$ is selected from the group consisting of C1–5 alkyl, C3–6 cycloalkyl, aryl, arylC1–5alkyl, C1–5 alkoxy, aryloxy, arylC1–3alkoxy, aroyl, amino, halogen, hydroxy, oxo, carboxy and cyano;

R6 is hydrogen or C1–5 alkyl said alkyl being optionally interrupted by 1 to two heteroatoms selected from the group consisting of N,O and S;

R7 is hydrogen, C1–5 alkyl said alkyl being optionally interrupted by 1 to two heteroatoms selected from the group consisting of N,O and S, C3–7 cycloalkyl, phenyl, naphthyl or cyano, wherein R7 is optionally substituted by one or more $R_e$;

$R_e$ is selected from the group consisting of C1–5 alkyl, C3–7 cycloalyl, phenyl, naphthyl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, pyrimidinyl, pyraziyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5alkoxy, heteroarylC1–5alkoxy, C1–5 alkoxycarbonyl, aryloxycarbonyl, C1–5 alkanoyloxy, aroyloxy, carbamoyl wherein the nitrogen atom may be independently mono or di-substitutcd by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio, arylthio, arylC1–5 alkylthio, ureido wherein either nitrogen atom may be independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinalinyl, halogen, hydroxy, oxo, carboxy and cyano, $R_e$ may be further optionally substituted by one or more $R_f$;

$R_f$ is selected from the group consisting of C1–5 alkyl, C3–7 cycloalkyl, phenyl optionally substituted by one or more groups selected from halogen, methyl and methoxy, naphthyl optionally substituted by one or more groups selected from halogen, methyl and methoxy, heterocyclyl selected from the group consisting of pyrrolidinyl, piperidinyl, morpholinyl, thiomorpholinyl, piperazinyl and indolinyl, heteroayl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzihiazolyl, quinolinyl, isoquinolinyl, quinazolinyl and quinoxalinyl, C1–5 alkoxy, aryloxy, arylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio, arylthio, ureido wherein either nitrogen atom may be independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pynidinyl, indolyl, benzofuranyl, benzothienyl, benzimidazolyl, benzthiazolyl, quinolinyl and isoquinolinyl, halogen, hydroxy, oxo, carboxy and cyano;

or R6 and R7 together with the carbon they are attached form a carbocyclic ring selected from the group consisting of cyclopropyl, cyclobutyl, cyclopentyl and cyclohexyl or a heterocyclic ring selected from the group consisting of piperidinyl, hexahydropyridazinyl, hexahydropyrimidinyl, piperazinyl, pyranyl and thiopyranyl, the carbocyclic or heterocyclic ring being optionally substituted with one or more $R_g$;

$R_g$ is selected from the group consisting of C1–3 alkyl, C3–6 cycloalkyl, C1–3 alkanoyl, benzoyl, C1–3 alkoxycarbonyl, carbamoyl wherein the nitrogen atom may be independantly mono or disubstitated by C1–5 alkyl, phenyl, heterocyclyl selected from the group consisting of piperidinyl, morpholinyl and piperazinyl or hetetoaryl selected from the group consisting of furanyl, thienyl and pyridinyl, balogen, hydroxy, carboxy and cyano, $R_g$ may be further optionally substituted by one or more $R_h$;

$R_h$ is selected from the group consisting of methyl, phenyl optionally substituted by one or more groups selected from halogen, methyl and methoxy, piperidinyl, morpholinyl, piperazinyl, pyridinyl, amino wherein the nitrogen atom may be independently mono or di-substituted by C1–3 alkyl, phenyl, heterocyclyl selected from the group consisting of piperdinyl and morpholinyl or heteroaryl selected from the group consisting of furanyl, thienyl and pyridinyl, halogen, hydroxy, oxo and cyano;

R8 is hydrogen, C1–5 alkyl, C5–6 cycloalkyl-C1–3 alkyl or benzyl;

$R_i$ is hydrogen or methyl; and

X is O.

4. A compound according to claim 3 wherein:

R1 is heterocyclyl selected from the group consisting of piperidinyl, morpholinyl, piperazinyl, pyranyl and thiopyranyl, heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl or amino, wherein R1 is optionally substituted by one or more $R_a$;

$R_a$ is selected from the group consisting of C1–3 alkyl, C3–6 cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl quinolinyl and isoquinolinyl, C1–3 alkoxy, phenoxy, C1–3 alkoxycarbonyl, aryloxycarbonyl, C1–5 alkanoyloxy, aroyloxy, carbamoyl wherein the nitrogen atom may be independently mono or di-substituted by C1–5 alkyl, phenyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamio, C1–5 alkylthio, arylthio, ureido wherein either nitrogen atom may be independently substituted by C1–5 alkyl, phenyl or naphthyl, C1–5 alkoxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranylanyl, benzothienyl, benzimidazolyl, benzthiazolyl, quinolinyl and isoquinolinyl, halogen, hydroxy, oxo, carboxy and cyano, $R_a$ may be further optionally substituted by one or more $R_b$;

$R_b$ is selected from the group consisting of C1–3 alkyl, C5–6 cycloalkyl, aryl, C1–3 alkoxy, phenoxy, halogen, hydroxy, oxo, carboxy and cyano;

R is hydrogen or Ori;

R3 is hydrogen;

R4 is hydrogen;

R5 is C1–5 alkyl, C3–6 cycloalkyl or phenyl, wherein R5 is optionally substituted by one or more $R_c$;

$R_c$ is selected from the group consisting of C1–3 alkyl, C3–6 cycloalkyl, phenyl, naphthyl, heterocyclyl selected from the group consisting of piperidinyl, morpholinyl and piperazinyl, heteroaryl selected from the group consisting of furanyl, thienyl, thiazolyl, imidazolyl, pyridinyl, indolyl, quinolinyl and isoquinolinyl, C1–5 alkoxy, phenoxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio, phenylthio, ureido wherein either nitrogen atom may be independently substituted by C1–3 alkyl, phenyl or heteroaryl selected the group consisting of furanyl, thienyl, pyrrolyl oxazolyl, thiazolyl, imidazolyl, pyridinyl and indolyl, C1–5 alkoxycarbonylamino, C1–5 alkylcarbamoyloxy, arylcarbamoyloxy, C1–5 alkylsulfonylamino, arylsulfonylamino, amino wherein the nitrogen atom may be independently mono or di-substituted by C1–3 alkyl, phenyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, $R_c$ may be further optionally substituted by one or more $R_d$;

$R_d$ is selected from the group consisting of C1–5 alkyl, C5–6 cycloalkyl, phenyl, naphthyl, arylC1–3alkyl, C1–5 alkoxy, phenoxy, arylC1–3alkoxy, aroyl, amino, halogen, hydroxy, oxo, carboxy and cyano;

R6 is hydrogen or C1–3alkyl said alkyl being optionally interrupted by 1 to two heteroatoms selected from the group consisting of N,O and S;

R7 is hydrogen, C1–5 alkyl said all being optionally interrupted by 1 to two heteroatoms selected from the group consisting of N,O and S, C3–6 cycloalkyl, phenyl or cyano, wherein R7 is optionally substituted by one or more $R_e$;

$R_e$ is selected from the group consisting of C1–3 alkyl, C3–6 cycloalkyl, phenyl, naphthyl, heterocyclyl selected from the group consisting of pyrrolidinyl, piperidinyl, morpholinyl and piperazinyl, heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxy, aryloxy, arylC1–3alkoxy, heteroarylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl or heteroaryl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, arylthio, arylC1–3alkylthio, ureido wherein either nitrogen atom may be independently substituted by C1–5 alkyl or phenyl, C1–5 alkoxycarbonylamino, C1–5 alkylsulfonylamino, arylsulfonylamino, amino wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, and indolyl, halogen, hydroxy, oxo, carboxy and cyano, $R_e$ may be further optionally substituted by one or more $R_f$;

$R_f$ is selected from the group consisting of C1–3 alkyl, C5–6 cycloalkyl, phenyl optionally substituted by one or more groups selected from halogen and methyl, heterocyclyl selected from the group consisting of pyrrolidinyl, piperidinyl, morpholinyl and piperazinyl, heteroaryl selected from the group consisting of furanyl, thienyl, pyrrolyl, oxazolyl, thiazolyl, imidazolyl, pyridinyl, pyrimidinyl, pyrazinyl and indolyl, C1–5 alkoxy, aryloxy, arylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl or aryl, C1–5 alkanoylamino, aroylamino, C1–5 alkylthio, arylthio, ureido wherein either nitrogen atom may be independently substituted by C1–5 alkyl or aryl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl or aryl, halogen, hydroxy, oxo, carboxy and cyano; or R6 and R7 together with the carbon they are attached form a carbocyclic ring selected from the group consisting of cyclopropyl, cyclobutyl, cyclopentyl and cyclohexyl or heterocyclic ring selected from the group consisting of piperidinyl, morpholinyl and thiomorpholinyl, the carbocyclic or heterocyclic ring being optionally substituted with one or more $R_g$;

$R_g$ is selected from the group consisting of C1–3 alkyl, C3–6 cycloalkyl, C1–3 alkanoyl, C1–3 alkoxycarbonyl and carbamoyl wherein the nitrogen atom may be independantly mono or disubstituted by C1–5 alkyl; $R_g$ may be further optionally substituted by one or more $R_h$; and $R_h$ is phenyl or amino wherein the nitrogen atom may be independently mono or di-substituted by C1–3 alkyl and R8 is hydrogen or methyl.

5. The compound according to claim 4 wherein:

R1 is heterocyclyl selected from the group consisting of piperidinyl, morpholinyl, piperazinyl, pyranyl and thiopyranyl; heteroaryl selected from the group consisting of furanyl, thienyl, pyrrolyl, oxazolyl, thiolyl, imidazolyl, pyridinyl and indolyl or amino, wherein R1 is optionally substituted by one or more $R_a$;

$R_a$ is selected from the group consisting of C1–3 alkyl, C5–6 cycloalkyl, phenyl, heterocyclyl selected from the group consisting of piperidinyl, morpholinyl and piperazinyl, heteroaryl selected from the group consisting of furanyl, thienyl, pyrrolyl, imidazolyl, tetrazolyl, pyridinyl, indolyl, benzofuranyl, benzothienyl, benzimidazolyl, benzthiazolyl, quinolinyl and isoquinolinyl, C1–3 alkoxy, C1–3 alkoxycarbonyl, aryloxycarbonyl, C1–5 alkanoyloxy, aroyloxy, carbamoyl wherein the nitrogen atom may be independently mono or di-substituted by C1–3 alkyl, phenyl or heteroaryl selected from the group consisting of pyrrolyl, imidazolyl, pyridinyl, indolyl, benzofuranyl, benzothienyl, benzimidazolyl and benzthiazolyl, C1–5 alkanoylamino, aroylamino, C1–3 alkylthio, arylthio, ureido wherein either nitrogen atom may be independently substituted by C1–3alkyl or phenyl, C1–5 alkylsulfonylamino, arylsulfonylamino, amino wherein the nitrogen atom may be independently mono or di-substituted by C1–3alkyl, phenyl, heterocyclyl selected from the group consisting of piperidinyl, morpholinyl and piperazinyl or heteroaryl selected from the group consisting of pyrrolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_a$ may be further optionally substituted by one or more $R_b$;

$R_b$ is selected from the group consisting of C1–3 alkyl, C5–6 cycloalkyl, C1–3 alkoxy, halogen and hydroxy;

R2 is hydrogen;

R5 is C1–5 alkyl, C5–6 cycloalkyl or phenyl wherein R5 is optionally substituted by one or more $R_c$;

$R_c$ is selected from the group consisting of C1–3 alkyl, C3–6 cycloalkyl, phenyl, naphthyl, 4piperidinyl, 4-morpholinyl, piperazinyl, furanyl, thienyl, thiazolyl, imidazolyl, pyridinyl, indolyl, C1–5 alkoxy, phenoxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl or phenyl, C1–5 alkanoylamino, C1–3 alkylthio, ureido wherein either nitrogen atom may be independently substituted by C1–3 alkyl or phenyl, C1–5 alkoxycarbonylamino, C1–5 alkylsulfonylamino, arylsulfonylamino, amino wherein the nitrogen atom may be independently mono or di-substituted by C1–3 alkyl or phenyl, halogen, hydroxy, oxo, carboxy and cyano, $R_c$ may be further optionally substituted by one or more $R_d$;

$R_d$ is selected from the group consisting of C1–5 alkyl, C5–6 cycloalkyl, phenyl, benzyl, C1–5 alkoxy, phenoxy, benzyloxy, aroyl, halogen, hydroxy, oxo, carboxy and cyano;

R6 is hydrogen or C1–3alkyl said alkyl being optionally interrupted by 1 to two heteroatoms selected from the group consisting of N,O and S;

R7 is hydrogen, C1–5 alkyl said alkyl being optionally interrupted by 1 to two heteroatoms selected from the group consisting of N,O and S, phenyl or cyano, wherein R7 is optionally substituted by one or more $R_e$;

$R_e$ is selected from the group consisting of C1–3 alkyl, C3–6 cycloalkyl, phenyl, naphthyl, furanyl, thienyl, thiazolyl, imidazolyl, pyridinyl, indolyl, C1–3 alkoxy, benzyloxy, pyridylC1–3alkoxy, thienylC1–3alkoxy, furanylC1–3alkoxy, C1–3 alkoxycarbonyl, phenoxyoxycarbonyl, C1–5 alkanoyloxy, aroyloxy, carbamoyl wherein the nitrogen atom may be independently mono or di-substituted by C1–3 alkyl or phenyl, C1–5 alkanoylamino, aroylamino, methylthio, benzylthio, ureido wherein either nitrogen atom may be independently substituted by C1–5 alkyl or phenyl, C1–3 alkoxycarbonylamino, amino wherein the nitrogen atom may be independently mono or di-substituted by C1–5 alkyl or phenyl, halogen, hydroxy, oxo, carboxy and cyano, $R_e$ may be further optionally substituted by one or more $R_f$;

$R_f$ is selected from the group consisting of C1–3 alkyl, phenyl optionally substituted by one or more groups selected from the group consisting of halogen and methyl, heterocyclyl selected from the group consisting of piperidinyl, morpholinyl and piperazinyl, heteroaryl selected from the group consisting of furanyl, thienyl, pyrrolyl and pyridinyl, C1–3 alkoxy, aryloxy, benzyloxy, C1–5 alkoxycarbonyl, C1–5 alkanoyloxy, aroyloxy, carbamoyl wherein the nitrogen atom may be independently mono or di-substituted by C1–5 alkyl or phenyl, C1–5 alkanoylamino, aroylamino, C1–5 alkylthio, ureido wherein either nitrogen atom may be independently substituted by C1–5 alkyl or phenyl, C1–5 alkoxycarbonylamino, C1–5 alkylcarbanoyloxy, arylcarbamoyloxy, C1–3 alkylsulfonylamino, arylsulfonylamino, C1–3 alkylaminosulfonyl arylaminosulfonyl, amino wherein the nitrogen atom may be independently mono or di-substituted by C1–3 alkyl or phenyl, halogen, hydroxy, oxo, carboxy and cyano;

or R6 and R7 together with the carbon they are attached form cyclopropyl or a heterocyclic ring selected from the group consisting of piperidinyl, pyranyl and thiopyranyl, the cyclopropyl or heterocyclic ring being optionally substituted with one or more $R_g$; and $R_g$ is selected from the group consisting of methyl, benzyl, acetyl, benzoyl, benzyloxycarbonyl and ethoxycarbonyl; and R8 is hydrogen.

6. The compound according to claim 5 wherein:

R1 is piperidinyl, morpholinyl, piperazinyldyl, pyranyl, thiopyranyl, furanyl, thienyl, pyrrolyl or amino, wherein R1 is optionally substituted by one or more $R_a$;

$R_a$ is selected from the group consisting of C1–3 alkyl, C5–6 cycloalkyl, phenyl, furanyl, thienyl, pyrrolyl, imidazolyl, indolyl, benzofuranyl, benzothienyl, benzimidazolyl, benzthiazolyl, C1–3 alkoxy, C1–3 alkoxycarbonyl, carbamoyl wherein the nitrogen atom may be independently mono or di-substituted by C1–3 alkyl or phenyl, C1–5 alkanoylamino, aroylamino, ureido wherein either nitrogen atom may be independently substituted by C1–3alkyl or phenyl, C1–5 alkylsulfonylamino, arylsulfonylamino, amino wherein the nitrogen atom may be independently mono or di-substituted by C1–3alkyl or phenyl, halogen, hydroxy, oxo, carboxy and cyano, $R_a$ may be further optionally substituted by one or more $R_b$;

$R_b$ is selected from the group consisting of C1–3alkyl, C1–3alkoxy, halogen and hydroxy;

R5 is C1–5 alkyl, C5–6 cycloalkyl or phenyl, wherein R5 is optionally substituted by one or more groups of the formula $R_c$;

$R_c$ is selected from the group consisting of C1–3 alkyl, C3–6 cycloalkyl, phenyl, naphthyl, 4-piperidinyl, furanyl, thienyl, thiazolyl, imidazolyl, pyridinyl, indolyl, C1–3 alkoxy, C1–5 alkoxycarbonyl, C1–5 alkanoyloxy, benzoyloxy, carbamoyl wherein the nitrogen atom may be independently mono or di-substituted by C1–3 alkyl or phenyl, C1–5 alkanoylamino, C1–3 alkylthio, C1–3 alkoxycarbonylamino, C1–3 alkylsulfonylamino, amino wherein the nitrogen atom may be independently mono or di-substituted by C1–3 alkyl or phenyl, halogen, hydroxy, oxo, carboxy and cyano, $R_c$ may be further optionally substituted by one or more $R_d$;

$R_d$ is selected from the group consisting of C1–3 alkyl, phenyl, benzyl, C1–3 alkoxy, phenoxy, benzyloxy, benzoyl, halogen, hydroxy, oxo, carboxy and cyano;

wherein the configuration at the stereocenter defined by R4 and R5 and the carbon they are attached to is defined as L;

R6 is hydrogen or C1–2 alkyl said alkyl being optionally interrupted by 1 to two heteroatoms selected from the group consisting of N,O and S;

R7 is C1–5 alkyl said alkyl being optionally interrupted by 1 to two heteroatoms selected from the group consisting of N,O and S; phenyl or cyano wherein R7 is optionally substituted by one or more groups of the formula $R_e$;

$R_e$ is selected from the group consisting of methyl, C3–6 cycloalkyl, phenyl, naphthyl, furanyl, thienyl, thiazolyl, imidazolyl, pyridinyl, indolyl, C1–3 alkoxy, benzyloxy, pyridylC1–3alkoxy, thienylC1–3alkoxy, furanylC1–3alkoxy, C1–5 alkanoylamino, aroylamino, methylthio, benzylthio, C1–3 alkoxycarbonylamino, amino wherein the nitrogen atom may be independently mono or di-substituted by C1–5 alkyl or phenyl, halogen, hydroxy, oxo, carboxy and cyano, $R_e$ may be further optionally substituted by one or more $R_f$;

$R_f$ is selected from the group consisting of C1–3 alkyl, phenyl optionally substituted by one or more groups selected from halogen and methyl, C1–3 alkoxy, aryloxy, benzyloxy, C1–3 alkoxycarbonyl, carbamoyl wherein the nitrogen atom may be independently mono or di-subsiituted by C1–3 alkyl or phenyl, C1–5 alkanoylamino, aroylamino, amino wherein the nitrogen atom may be independently mono or di-substituted by C1–3 alkyl or phenyl, halogen, hydroxy, oxo, carboxy and cyano;

or R6 and R7 together with the carbon they are attached form cyclopropyl or a heterocyclic ring selected from the group consisting of piperidinyl and pyranyl, the cyclopropyl or heterocyclic ring being optionally substituted with one or more $R_g$; and $R_g$ is methyl.

7. The compound according to claim 6 wherein:

R1 is piperidinyl, morpholinyl, piperazinyl, pyranyl, thiopyranyl or amino wherein R1 is optionally substituted by one or more $R_a$;

$R_a$ is selected from the group consisting of C1–3 alkyl, C5–6 cycloalkyl, phenyl, furanyl, thienyl, pyrrolyl, imidazolyl, indolyl, benzofuranyl, benzothienyl, benzimidazolyl, benzthiazolyl, C1–3 alkoxy, C1–3 alkoxycarbonyl, carbamoyl wherein the nitrogen atom may be independently mnono or di-substituted by C1–3 alkyl or phenyl, C1–5 alkanoylamino, aroylamino, C1–5 alkylsulfonylamino, arylsulfonylamino, amino wherein the nitrogen atom may be independently mono or di-substituted by C1–3 alkyl, halogen, hydroxy, oxo, carboxy and cyano, $R_a$ may be further optionally substituted by one or more $R_b$;

$R_b$ is selected from the group consisting of C1–3 alkoxy, halogen and hydroxy, R5 is C1–5 alkyl or C5–6 cycloalkyl wherein R5 is optionally substituted by one or more $R_c$;

$R_c$ is selected from the group consisting of methyl, C3–6 cycloalkyl, phenyl, naphthyl, thienyl, imidazolyl, pyridinyl, indolyl, C14 alkoxy, C1–5 alkanoylamino, methylthio, halogen, hydroxy, oxo, carboxy and cyano, $R_c$ may be further optionally substituted by one or more $R_d$;

$R_d$ is selected from the group consisting of methyl, phenyl, benzyl, methoxy, phenoxy, benzyloxy, benzoyl, halogen and hydroxy;

R7 is C1–5 alkyl or phenyl, wherein R7 is optionally substituted by one or more $R_e$;

$R_e$ is selected from the group consisting of C3–6 cycloalkyl, phenyl, naphthyl, thienyl, imidazolyl, pyrdinyl, indolyl, methoxy, benzyloxy, C1–3 alkanoylamino, methylthio wherein the sulfur atom may be oxidized to a sulfoxide or sulfone, benzylthio wherein the sulfur atom may be oxidized to a sulfoxide or sulfone, methoxycarbonylamino, amino wherein the nitrogen atom may be independently mono or di-substituted by C1–3 alkyl, halogen, hydroxy, carboxy and cyano, $R_e$ may be further optionally substituted by one or more $R_f$;

$R_f$ is selected from the group consisting of methyl, phenyl optionally substituted by one or more groups selected from halogen or methyl, methoxy, phenoxy, benzyloxy, methoxycarbonyl, amino wherein the nitrogen atom may be independently mono or di-substituted by C1–3 alkyl or phenyl, halogen, hydroxy and carboxy;

or R6 and R7 together with the carbon they are attached form a cyclopropyl ring.

8. The compound according to claim 7 wherein:

R1 is piperidinyl, morpholinyl, piperazinyl, pyranyl or thiopyranyl, wherein R1 is optionally substituted by one or more $R_a$;

$R_a$ is selected from the group consisting of pyrrolyl, imidazolyl, indolyl, benzimidazolyl, methoxy, methoxycarbonyl, amino wherein the nitrogen atom may be independently mono or di-substituted by C1–3 alkyl, halogen, hydroxy and carboxy, $R_a$ may be further optionally substituted by one or more $R_b$;

$R_b$ is selected from the group consisting of methoxy, halogen and hydroxy;

$R_c$ is selected from the group consisting of methyl C3–6 cycloalkyl, phenyl, naphthyl, C1–4 alkoxy, C1–3 alkanoylamio, methylthio, halogen, hydroxy, oxo, carboxy and cyano, $R_c$ may be further optionally substituted by one or more $R_d$;

$R_d$ is selected from the group consisting of methyl, phenyl, methoxy, halogen and hydroxy;

R6 is hydrogen;

$R_e$ is selected from the group consisting of C5–6 cycloalkyl, phenyl, naphthyl, thienyl, indolyl, methoxy, benzyloxy, methylthio, benzylthio, methoxycarbonylamino, halogen, hydroxy, carboxy and cyano, $R_e$ may be further optionally substituted by one or more $R_f$; and $R_f$ is selected from the group consisting of methyl, phenyl optionally substituted by halogen, methoxy, phenoxy, benzyloxy, methoxycarbonyl, halogen, hydroxy and carboxy.

9. The compound according to claim 8 wherein:

R1 is 4-morpholinyl or 4-pyranyl;

R5 is C1–5 alkyl wherein R5 is optionally substituted by one or more $R_c$;

$R_c$ is selected from the group consisting of C3–6 cycloalkyl, phenyl and 2-naphthyl, $R_c$ may be further optionally substituted by one or more $R_d$;

$R_d$ is selected from the group consisting of methyl and halogen;

$R_c$ is selected from the group consisting of C5–6 cycloalkyl, phenyl, naphthyl, indolyl, benzyloxy, methylthio, benzylthiohalogen and carboxy, $R_e$ may be further optionally substituted by one or more $R_f$; and $R_f$ is selected from the group consisting of methyl, methoxy, methoxycabonyl, halogen and hydroxy.

10. A compound of the formula (Ia):

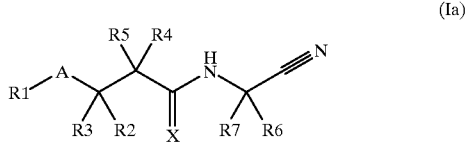

wherein:
A is —C(O)— or CH(OR8)—;
R1 is heterocyclyl selected from the group consisting of pyrrolidinyl, piperidinyl, morpholinyl, thiomorpholinyl, 2-oxa-5-aza-bicyclo[2,2,1]heptanyl, piperazinyl, indolinyl, tetrahydropyranyl and tetrahydrothiopyranyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl and amino wherein R1 is optionally substituted by one or more $R_a$;
$R_a$ is selected from the group consisting of a bond, C1–8 alkyl, C3–7 cycloalkyl, aryl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, C1–8 alkoxycabonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamno, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by akyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyrimidinyl, pyridazinyl, pyridinyl, pyrazinyl, indolyl, isoindolyl, benzofuranyl, benzothienyl, benzimidazolyl, benzthiazolyl, purinyl, quinolinyl, isoquinolinyl, quinazolinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, pyrazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino, guanidino; $R_a$ may be further optionally substituted by one or more $R_b$;
$R_b$ is selected from the group consisting of C1–8 alkyl, C3–6 cycloalkyl, aryl, heteroaryl, C1–8 alkoxy, aryloxy, alkanoyl, aroyl, amino wherein the nitrogen atom may be independently mono or di-substituted by alkyl, cycloalkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, pyridinyl, pyridazinyl, pyrimidinyl, pyrazinyl, indolyl, isoindolyl, benzofuranyl, benzothienyl, benzimidazolyl, benzthiazolyl, quinolinyl and isoquinolinyl, halogen, hydroxy, oxo, carboxy, cyano, nitro, amidino and guanidino;
R2 is hydrogen, $OR_j$ or C1–3 alkyl;
R3 is hydrogen or C1–5 alkyl;
R4 is hydrogen or C1–5 alkyl;
R5 is hydrogen, C1–8 alkyl, C3–7 cycloalkyl, aryl wherein R5 is optionally substituted by one or more $R_c$;
$R_c$ is selected from the group consisting of a bond, C1–8 alkyl, C3–7 cycloalkyl, bicycloalkyl, aryl, dihydronaphthyl, tetrahydronaphthyl, indenyl, indanyl, heterocyclyl selected from the group consisting of pyrrolidinyl, piperidinyl, morpholinyl, thiomorpholinyl, piperazinyl and indolinyl; hetroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, alkanoyl, aroyl, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, C1–5aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_c$ may be further optionally substituted by one or more $R_d$;

$R_d$ is selected from the group consisting of C1–8 alkyl, C3–6 cycloalkyl, aryl, axylalkyl, C1–8 alkoxy, aryloxy, arylalkoxy, aroyl, amino, halogen, hydroxy, oxo, carboxy, cyano, nitro, amidino and guanidino;

R6 is hydrogen or lower alkyl wherein one or more carbon atoms are optionally replaced by 1 to two heteroatoms selected from the group consisting of N,O and S;

R7 is hydrogen, C1–8 alkyl wherein one or more carbon atoms are optionally replaced by 1 to two heteroatoms selected from the group consisting of N,O and S, C3–7 cycloalkyl, aryl, heteroaryl or cyano, wherein R7 is optionally substituted by one or more $R_e$;

$R_e$ is selected from the group consisting of a bond, C1–8 alkyl, C3–7 cycloalkyl, aryl, heterocyclyl selected from the group consisting of pyrrolidinyl, piperidinyl, moxpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl triazolyl, tetrazolyl, thiadiazolyl, pyridinyl, pyridazinyl, pyrimidinyl, pyrazinyl, indolyl, isoindolyl, benzfuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, heteroarylC1–8alkoxy wherein the heteroaryl is as hereinabove decribed in this paragraph, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroayl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylino, C1–8 alkylthio wherein the sulfur atom may be oxidized to a sulfoxide or sulfone, arylthio wherein the sulfur atom may be oxidized to a sulfoxide or sulfone, arylC1–8 alkylthio, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, arylcarbamoyloxy, arylcarbamoyloxy, alkylsulfonylamino, arylsulfonylamino, alkylaminosulfonyl, arylaminosulfonyl, amino wherein the nitrogen atom may he independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_e$ may be further optionally substituted by one or more $R_f$;

$R_f$ is selected from the group consisting C1–8 alkyl, C3–7 cycloalkyl, aryl optionally substituted by one or more groups selected from the group consisting halogen, methyl and methoxy, heterocyclyl selected from the group consisting pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino, and guanidino;

or R6 and R7 together with the carbon they are attached form a 3 to 7 membered carbocyclic or heterocyclic ring, the carbocyclic or heterocyclic ring being optionally substituted with one or more $R_g$;

$R_g$ is selected from the group consisting of a bond, alkyl, cycloalkyl, bicycloalkyl, phenyl, naphthyl, benzyl, dihydronaphthyl, tetrahydronaphthyl, indenyl, indanyl, heterocyclyl selected from the group consisting of pyrrolidinyl, piperidinyl, morpholinyl, thiomorpholinyl, tetrahydropyranyl, tetrahydrothiopyranyl, indolinyl and piperazinyl, heteroaryl selected from the group consisting of furanyl, thienyl, pyrimidinyl and pyridinyl, C1–5alkanoyl, aroyl, C1–5alkoxycarbonyl, aryloxycarbonyl, carbamoyl wherein the nitrogen atom may be independantly mono or disubstituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, thiazolyl, imidazolyl, pyridinyl, benzimidazolyl and quinolinyl, amino wherein the nitrogen atom may be independently mono or di-substituted by C1–5 alkyl, C3–6 cycloalkyl, C7–8 bicycloalkyl, phenyl, benzyl, benzoyl or naphthoyl, C1–5 alkylthio wherein the sulfur atom may be oxidised to a sulfoxide or sulfone, arylthio wherein the sulfur atom may be oxidised to a sulfoxide or sulfone, C1–5 alkylaminosulfonyl, arylaminosulfonyl, halogen, hydroxy, oxo, carboxy and cyano, $R_g$ may be further optionally substituted by one or more $R_h$;

$R_h$ is selected from the group consisting of C1–5 alkyl, C3–7 cycloalkyl, aryl optionally substituted by one or more groups selected from halogen, C1–5 alkyl or C1–5 alkoxy, dihydronaphthyl, tertrahydronaphthyl, indenyl, indanyl, benzyl, benzyloxy, heterocyclyl selected from the group consisting of pyrrolidinyl, piperidinyl, morpholinyl, thiomorpholinyl, piperazinyl, indolinyl, tetrahydropyranyl and tetrahydrothiopyranyl, heteroaryl selected from the group consisting of furanyl, thienyl, pyrrolyl, imidazolyl, pyridinyl, pyrimidinyl, pyrazinyl, indolyl, benzimidazolyl, quinolinyl, isoquinolinyl, quinazolinyl, benzoxazolyl and quinoxalinyl, C1–5 alkoxy, aryloxy, amino wherein the nitrogen atom may be independently mono or di-substituted by alkyl, aryl, heterocyclyl selected from the group consisting of piperidinyl and morpholinyl, or heteroaryl selected from the group consisting of furanyl, thienyl and pyridinyl halogen, hydroxy, oxo, carboxy and cyano; and R8 is hydrogen, alkyl, cycloalkyl-alkyl or arylalkyl;

$R_i$ is C1–8 alkyl, hydroxy, oxo and halogen $R_j$ is hydrogen or alkyl and

X is O.

11. The compound according to claim 10 wherein:

R1 is heterocyclyl selected from the group consisting of pyrrolidinyl, piperidinyl, morpholinyl, thiomorpholinyl, 2-oxa-5-aza-bicyclo[2,2,1]heptanyl, piperazinyl, indolinyl, tetrahydropyranyl and tetrahydrothiopyranyl, heteroaryl selected from the group consisting of furanyl, thienyl, pyrrolyl, oxazolyl, thiazolyl, imidazolyl pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl and amino wherein R1 is optionally substituted by one or more $R_a$;

$R_a$ is selected from the group consisting of a bond, C1–8 alkyl, C3–7 cycloalkyl, aryl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, pyrazolyl, isoxazolyl, isothiaolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothiienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocryclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzmidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherean either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinaziolinyl, quinoxalinyl, carbazolyl, phenothiazinyl and phenoxazinyl, alkoxycabonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, pyrazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino, guanidino; $R_a$ may be further optionally substituted by one or more $R_b$;

$R_b$ is selected from the group consisting of C1–8 alkyl, C3–6 cycloalkyl, aryl, heteroaryl, C1–8 alkoxy, aryloxy, alkanoyl, aroyl, amino wherein the nitrogen atom may be independently mono or di-substituted by alkyl, cycloalkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, pyridinyl, pyridazinyl, pyrimidinyl, pyrazinyl, indolyl, isoindolyl, benzofuranyl, benzothienyl, benzimidazolyl, benzthiazolyl, quinolinyl and isoquinolinyl, halogen, hydroxy, oxo, carboxy, cyano, nitro, amidino and guanidino, R2 is hydrogen, $OR_j$ or C1–3 alkyl;

R3 is hydrogen or C1–5 alkyl;

R4 is hydrogen or C1–5 alkyl;

R5 is hydrogen, C1–8 alkyl, C3–7 cycloalkyl, aryl whetin R5 is optionally substituted by one or more $R_c$;

$R_c$ is selected from the group consisting of a bond, C1–8 alkyl, C3–7 cycloalkyl, bicycloalkyl, aryl, dihydronaphthyl, tetrahydronaphthyl, indenyl, indanyl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyidazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, alkanoyl, aroyl, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, C1–5aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_c$ may be further optionally substituted by one or more $R_d$;

$R_d$ is selected from the group consisting of C1–8 alkyl, C3–6 cycloalkyl, aryl, arylalkyl, C1–8 alkoxy, aryloxy, arylalkoxy, aroyl, amino, halogen, hydroxy, oxo, carboxy, cyano, nitro, amidino and guanidino;

R7 is hydrogen, C1–8 alkyl wherein one or more carbon atoms are optionally replaced by 1 to two heteroatoms selected from the group consisting of N,O and S, C3–7 cycloalkyl, aryl, heteroaryl or cyano, wherein R7 is optionally substituted by one or more $R_e$;

$R_e$ is selected from the group consisting of a bond, C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, heteroarylC1–8alkoxy wherein the heteroaryl is as hereinabove decribed in this paragraph, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alknoylamino, aroylamino, C1–8 alkylthio wherein the sulfur atom may be oxidized to a sulfoxide or sulfone, arylthio wherein the sulfur atom may be oxidized to a sulfoxide or sulfone, arylC1–8 alkylthio, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, ioquinolinyl, quinazolinyl, quinoxalinyl, carbazolyl, phenothiazinyl and phenoxazinyl, alkoxycarbonylamino, aryloxycarbonylamino, alkylcarbamoyloxy, aylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_e$ may be further optionally substituted by one or more $R_f$;

$R_f$ is selected from the group consisting C1–8 alkyl, C3–7 cycloalkyl, aryl optionally substituted by one or more groups selected from the group consisting halogen, methyl and methoxy, heterocyclyl selected from the group consisting pyrrolidinyl, piperidinyl, morpholinyl, thiomorpholinyl, piperazinyl and indolinyl; heteroaryl selected from the group consisting of furanyl, thienyl, pyrrolyl, oxazolyl thiazolyl, imidazolyl, pyrazolyl, isoxazoly, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiaolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consistng of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, aklylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino, and guanidino;

or R6 and R7 together with the carbon they are attached form a 3 to 7 membered carbocyclic or heterocyclic ring, the carbocyclic or heterocyclic ring being optionally substituted with one or more $R_g$;

$R_g$ is selected from the group consisting of a bond, alkyl, cycloalkyl, bicycloalkyl, phenyl, naphthyl, benzyl, dihydronaphthyl, tetrahydronaphthyl, indenyl, indanyl, heterocyclyl selected from the group consisting of pyrrolidinyl, piperidinyl, morpholinyl, thiomorpholinyl, tetrahydropyranyl, tetrahydrothiopyranyl, indolinyl and piperazinyl, heteroaryl selected from the group consisting of furanyl, thienyl, pyrimidinyl and pyridinyl, C1–5alkanoyl, aroyl, C1–5alkoxycarbonyl, aryloxycarbonyl, carbamoyl wherein the nitrogen atom may be independantly mono or disubstituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, thiazolyl, imidazolyl, pyridinyl, benzimidazolyl and quinolinyl, amino wherein the nitrogen atom may be independently mono or di-substituted by C1–5 alkyl, C3–6 cycloalkyl, C7–8 bicycloalkyl, phenyl, benzyl, benzoyl or naphthoyl, C1–5 alkylthio wherein the sulfur atom may be oxidised to a sulfoxide or sulfone, arylthio wherein the sulfur atom may be oxidised to a sulfoxide or sulfone, C1–5 alkylaminosulfonyl, arylaminosulfonyl, halogen, hydroxy, oxo, carboxy and cyano, $R_g$ may be further optionally substituted by one or more $R_h$;

$R_h$ is selected from the group consisting of C1–5 alkyl, C3–7 cycloalkyl, aryl optionally substituted by one or more groups selected from halogen, C1–5 alkyl or C1–5 alkoxy, dihydronaphthyl, tetrahydroaphthyl, indenyl, indanyl, benzyl, benzyloxy, heterocyclyl selected from the group consisting of pyrrolidinyl, piperidinyl, morpholinyl, thiomoxpholinyl, piperazinyl, indolinyl, tetrahydropyranyl and tetrahydrothiopyranyl, heteroaryl selected from the group consisting of furanyl, thienyl, pyrrolyl, imidazolyl, pyridinyl, pyrimidinyl, pyrazinyl, indolyl, benizimidazolyl, quinolinyl, isoquinolinyl, quinazolinyl, benzoxazolyl and quinoxalinyl, C1–5 alkoxy, aryloxy, amino wherein the nitrogen atom may be independently mono or di-substituted by alkyl, aryl, heterocyclyl selected from the group consisting of piperidinyl and morpholinyl, or heteroaryl selected from the group consisting of furanyl, thienyl and pyridinyl, halogen, hydroxy, oxo, carboxy and cyano; and R8 is hydrogen, alkyl, cycloalkyl-alkyl or arylalkyl;

$R_i$ is C1–8 alkyl, hydroxy, oxo and halogen $R_j$ is hydrogen or alkyl and

X is O.

12. A compound according to claim 11 wherein:

A is —C(O)—;

R1 is heterocyclyl selected from the group consisting of pyrrolidinyl, piperdinyl, morpholinyl, thiomorpholinyl, 2-oxa-5-aza-bicyclo[2,2,1]heptanyl, piperazinyl, tetrahydropyranyl and tetrahydrothiopyranyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl or amino, wherein R1 is optionally substituted by one or more $R_a$;

$R_a$ is selected from the group consisting of a bond, C1–3 alkyl, C3–6 cycloalkyl, phenyl, naphthyl, heterocyclyl selected from the group consisting of pyrrolidinyl, piperidinyl, morpholinyl and piperazinyl; heteroaxyl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, quinolinyl and isoquinolinyl, C1–3 alkoxy, phenoxy, C1–3 alkoxycarbonyl, aryloxycarbonyl, C1–5 alkanoyloxy, aroyloxy, carbamoyl wherein the nitrogen atom may be independently mono or di-substituted by C1–5 alkyl, phenyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio, arylthio, ureido wherein either nitrogen atom may be independently substituted by C1–5alkyl, phenyl or naphthyl; C1–5 alkoxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_a$ may be further optionally substituted by one or more $R_b$;

$R_b$ is selected from the group consisting of C1–3 alkyl, C5–6 cycloalkyl, aryl, heteroaryl selected from the group consisting of furanyl thienyl, pyrrolyl, oxazolyl, thizolyl, imidazolyl, pyridinyl, indolyl, benzofuranyl, benzothienyl, benzimidazolyl, benzthiazolyl, quinolinyl and isoquinolinyl, C1–3 alkoxy, phenoxy, C1–8 alkanoyl, amino wherein the nitrogen atom may be independently mono or di-substituted by C1–5alkyl, C3–6 cycloalkyl, phenyl or naphthyl, halogen, hydroxy, oxo, carboxy and cyano;

R2 is hydrogen;
R3 is hydrogen;
R4 is hydrogen;
R5 is C1–5 alkyl, C3–6 cycloalkyl or phenyl, wherein R5 is optionally substituted by one or more $R_c$;

$R_c$ is selected from the group consisting of a bond, C1–3 alkyl, C3–6 cycloalkyl, phenyl, naphthyl, indenyl, indanyl, heterocyclyl selected from the group consisting of piperidinyl, morpholinyl and piperazinyl, heteroaryl selected from the group consisting of furanyl, thienyl, thiazolyl, imidazolyl, pyridinyl indolyl, quinolinyl, and isoquinolinyl, C1–5 alkoxy, phenoxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consistng of furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl or heteroaryl selected the group consisting of furanyl, thienyl, pyrrolyl oxazolyl, thiazolyl, imidazolyl, pyridinyl and indolyl, C1–5 alkoxycarbonylamino, C1–5 alkylcarbanoyloxy, arylcarbamoyloxy, C1–5 alkylsulfonylamino, arylsulfonylamino, amino wherein the nitrogen atom may be independently mono or di-substituted by C1–3 alkyl, phenyl, heterocyclyl selected from the group consisting of piperidinyl, morpholinyl and piperaznyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, $R_c$ may be further optionally substituted by one or more $R_d$;

$R_d$ is selected from the group consisting of C1–5 alkyl, C5–6 cycloalkyl, phenyl, naphthyl, arylC1–3alkyl, C1–5 alkoxy, phenoxy, arylC1–3alkoxy, aroyl, amino, halogen, hydroxy, oxo, carboxy and cyano;

R6 is hydrogen or C1–3alkyl wherein one or more carbon atoms are optionally replaced by 1 to two heteroatoms selected from the group consisting of N,O and S;

R7 is hydrogen, C1–5 alkyl wherein one or more carbon atoms are optionally replaced by 1 to two heteroatoms selected from the group consisting of N,O and S, C3–6 cycloalkyl, phenyl, naphthyl, heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl or cyano, wherein R7 is optionally substituted by one or more $R_e$;

$R_e$ is selected from the group consisting of C1–3 alkyl, C3–6 cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxy, aryloxy, arylC1–3alkoxy, heteroarylC1–3alkoxy wherein the heteroaryl is as hereinabove described in this paragraph, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl or heteroayl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, arylthio wherein the sulfur atom may be oxidized to a sulfoxide or sulfone, arylC1–3alkylthio wherein the sulfur atom may be oxidized to a sulfoxide or sulfone, ureido wherein either nitrogen atom may be independently substituted by C1–5 alkyl or phenyl, C1–5 alkoxycarbonylamino, C1–5 alkylsulfonylamaino, arylsulfonylamino, amino wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl and pyridinyl, indolyl, halogen, hydroxy, oxo, carboxy and cyano, $R_e$ may be further optionally substituted by one or more $R_f$;

$R_f$ is selected from the group consisting of C1–5 alkyl, C3–6 cycloalkyl, phenyl optionally substituted by one or more groups selected from halogen or methyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, pyrimidinyl, pyrazinyl and indolyl, C1–5 alkoxy, aryloxy, arylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl or aryl, C1–5 alkylanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl or aryl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl or aryl, halogen, hydroxy, oxo, carboxy and cyano; or R6 and R7 together with the carbon they are attached form a carbocyclic ring selected from the group consisting of cyclopropyl, cyclobutyl, cyclopentyl, cyclohexyl, cycloheptyl or heterocyclic ring selected from the group consisting of azetidinyl, pyrrolidinyl, piperidinyl, tetrahydropyranyl and tetrahydrothiopyranyl, the carbocyclic or heterocyclic ring being optionally substituted with one or more $R_g$;

$R_g$ is selected from the group consisting of a bond, C1–8 alkyl, C3–8 cycloalkyl, C7–8 bicycloalkyl, benzyl, dihydronaphthyl, tetrahydronaphthyl, indenyl, indanyl, heterocyclyl selected from the group consisting of pyrrolidinyl, piperidinyl, tetrahydropyranyl, tetrahydrothiopyranyl, piperazinyl and morpholinyl, heteroaryl selected from the group consisting of thienyl, pyrimidinyl and pyridinyl, C1–5 alkanoyl, C1–3 alkoxycarbonyl, carbamoyl wherein the nitrogen atom may be independantly mono or disubstituted by C1–5 alkyl and amino wherein the nitrogen atom may be independently mono or di-substituted by C1–5 alkyl, C3–6 cycloalkyl, C7–8 bicycloalkyl, phenyl, benzyl, benzoyl or naphthoyl, $R_g$ may be further optionally substituted by one or more $R_h$; and $R_h$ is selected from the group consisting of C1–8 alkyl, C3–8 cycloalkyl, phenyl, benzyl, benzyloxy, heterocyclyl selected from the group consisting of piperidinyl, indolinyl, tetrahydropyranyl and tetrahydrothiopyranyl, heteroaryl selected from the group consisting of thienyl, pyrrolyl, pyridinyl, pyrimidinyl, indolyl, benzimidazolyl, quinolinyl and isoquinolinyl, amino wherein the nitrogen atom may be independently mono or di-substituted by C1–3 alkyl, halogen, hydroxy, oxo, cyano and tifluoromethyl.

13. The compound according to claim 12 wherein:

R1 is pyrrolidinyl, piperidinyl, morpholinyl, thiomorpholinyl, piperazinyl, tetrahydropyranyl, furanyl, thienyl, pyrrolyl or amino, wherein R1 is optionally substituted by one or more $R_a$;

$R_a$ is selected from the group consisting of a bond, C1–3 aryl, C5–6 cycloalkyl, phenyl, furanyl, thienyl, pyrrolyl, imidazolyl, indolyl, benzofuranyl, benzothienyl, benzimidazolyl, benzthiazolyl, C1–3 alkoxy, C1–3 alkoxycarbonyl, carbamoyl wherein the nitrogen atom may be independently mono or di-substituted by C1–3 alkyl or phenyl; C1–5alkoxycarbonylamino, C1–5 alkanoylamino, aroylamino, ureido wherein either nitrogen atom may be independently substituted by C1–3alkyl or phenyl, C1–5 alkylsulfonylamino, arylsulfonylamino, amino wherein the nitrogen atom may be independently mono or di-substituted by C1–3alkyl or phenyl, halogen, hydroxy, oxo, carboxy and cyano, $R_a$ may be further optionally substituted by one or more $R_b$;

$R_b$ is selected from the group consisting of C1–3alkyl, C1–3alkoxy, amino wherein the nitrogen atom may be independently mono or di-substituted by C1–3alkyl or phenyl halogen, oxo and hydroxy;

R5 is C1–5 alkyl, C3–6 cycloalkyl or phenyl, wherein R5 is optionally substituted by one or more groups of the formula $R_c$;

$R_c$ is selected from the group consisting of a bond, C1–3 alkyl, C3–6 cycloalkyl, C7–8 bicycloalkyl, phenyl, naphthyl, dihydronaphthyl, tetrahydronaphthyl, indenyl, indanyl, 4-piperidinyl, furanyl, thienyl, thiazolyl, imidazolyl, pyridinyl, indolyl, C1–3 alkoxy, C1–5 alkoxycarbonyl, C1–5 alkanoyloxy, benzoyloxy, carbamoyl wherein the nitrogen atom may be independently mono or di-substituted by C1–3 alkyl or phenyl, C1–5 alkanoylamino, C1–3 alkylthio wherein the sulfur atom may be oxidized to a sulfoxide or sulfone, C1–3 alkoxycarbonylamino, C1–3 alkylsulfonylamino, amino wherein the nitrogen atom may be independently mono or di-substituted by C1–3 alkyl or phenyl, halogen, hydroxy, oxo, carboxy and cyano, $R_c$ may be further optionally substituted by one or more $R_d$;

$R_d$ is selected from the group consisting of C1–3 alkyl, phenyl, benzyl, C1–3 alkoxy, phenoxy, benzyloxy, benzoyl, halogen, hydroxy, oxo, carboxy and cyano;

wherein the configuration at the stereocenter defined by R4 and R5 and the carbon they are attached to is defined as L;

R6 is hydrogen or C1–2alkyl one or more carbon atoms are optionally replaced by 1 to two heteroatoms selected from the group consisting of N,O and S;

R7 is C1–5 alkyl said alkyl being optionally interrupted by 1 to two heteroatoms selected from the group consisting of N,O and S; phenyl, pyridinyl or cyano wherein R7 is optionally substituted by one or more groups of the formula $R_e$;

$R_e$ is selected from the group consisting of a bond, methyl, C3–6 cycloalkyl, phenyl, naphthyl, furanyl, thienyl, thiazolyl, imidazolyl, pyridinyl, pyrrolidinyl, piperidinyl, indolyl, C1–3 alkoxy, benzyloxy, pyridinylC1–3alkoxy, thienylC1–3alkoxy, furanylC1–3alkoxy, C1–5 alkanoylamino, aroylamino, methylthio wherein the sulfur atom may be oxidized to a sulfoxide or sulfone, benzylthio wherein the sulfur atom may be oxidized to a sulfoxide or sulfone, C1–3 alkoxycarbonylamino, amino wherein the nitrogen atom may be independently mono or di-substituted by C1–5 alkyl or phenyl, halogen, hydroxy, oxo, carboxy and cyano, $R_e$ may be further optionally substituted by one or more $R_f$;

$R_f$ is selected from the group consisting of C1–5 alkyl, C3–6 cycloalkyl, phenyl optionally substituted by one or more groups selected from halogen or methyl, C1–3 alkoxy, aryloxy, benzyloxy, C1–3 alkoxycarbonyl, carbamoyl wherein the nitrogen atom may be independently mono or di-substituted by C1–3 alkyl or phenyl, C1–5 alkanoylamino, aroylamino, amino wherein the nitrogen atom may be independently mono or di-substituted by C1–3 alkyl or phenyl, halogen, hydroxy, oxo, carboxy and cyano;

R6 and R7 together with the carbon they are attached form a carbocyclic ring selected from the group consisting of cyclopropyl, cyclopentyl, cyclohexyl and cycloheptyl or heterocyclic ring selected from the group consisting of pyrrolidinyl, piperidinyl and tetrahydropyranyl, the carbocyclic or heterocyclic ring being optionally substituted with one or more $R_g$;

$R_g$ is selected from the group consisting of a bond C1–8 alkyl, C3–8 cycloalkyl, C7–8 bicycloalkyl, benzyl, dihydronaphthyl, tetrahydronaphthyl, indanyl, heterocyclyl selected from the group consisting of piperidinyl, tetrahydropyranyl, and tetrahydrothiopyranyl, C1–5 alkanoyl, C1–3 alkoxycarbonyl, carbamoyl wherein the nitrogen atom may be independantly mono or disubstituted by C1–5 alkyl and amino wherein the nitrogen atom may be independently mono or di-substituted by C1–5 alkyl, C3–6 cycloalkyl, C7–8 bicycloalkyl, phenyl, benzyl, benzoyl or naphthoyl, $R_g$ may be further optionally substituted by one or more $R_h$; and $R_h$ is selected from the group consisting of C1–8 alkyl, C3–8 cycloalkyl, phenyl, benzyl, benzyloxy, heterocyclyl selected from the group consisting of piperidinyl, indolinyl, tetrahydropyranyl and tetrahydrothiopyranyl, heteroaryl selected from the group consisting of thienyl, pyridinyl, indolyl, pyrrolyl and benzimidazolyl, amino wherein the nitrogen atom may be independently mono or di-substituted by methyl, halogen, hydroxy, oxo, cyano and trifluoromethyl.

14. The compound according to claim 13 wherein:

R1 is pyrroildinyl, piperidinyl, morpholinyl, thiomorpholinyl, or amino wherein R1 is optionally substituted by one or more $R_a$;

$R_a$ is selected from the group consisting of a bond, C1–3 alkyl, C5–6 cycloalkyl, phenyl, furanyl, thienyl, pyrrolyl, imidazolyl, indolyl, benzofuranyl, benzothienyl, benzimidazolyl, benzthiazolyl, C1–3 alkoxy, C1–3 alkoxycarbonyl, carbamoyl wherein the nitrogen atom may be independently mono or di-substituted by C1–3 alkyl or phenyl, C1–5alkoxycarbonylamino, C1–5 alkanoylamino, aroylamino, C1–5 alkylsulfonylamino, arylsulfonylamino, amino wherein the nitrogen atom may be independently mono or di-substituted by C1–3 alkyl, halogen, hydroxy, oxo, carboxy and cyano, $R_a$ may be further optionally substituted by one or more $R_b$;

$R_b$ is selected from the group consisting of C1–3 alkoxy, halogen and hydroxy, R5 is C1–5 alkyl wherein R5 is optionally substituted by one or more $R_c$;

$R_c$ is selected from the group consisting of a bond, C3–6 cycloalkyl, C7–8 bicycloalkyl, phenyl, naphthyl, dihydronaphthyl, tetrahydronaphthyl, indanyl, thienyl, imidazolyl, pyridinyl, indolyl, C1–3 alkoxy, C1–5 alkanoylamino, methylthio, halogen, hydroxy, oxo, carboxy and cyano, $R_c$ may be further optionally substituted by one or more $R_d$;

$R_d$ is selected from the group consisting of C1–3 alkyl, phenyl, benzyl, methoxy, phenoxy, benzyloxy, benzoyl, halogen and hydroxy;

R7 is C1–5 alkyl or phenyl, wherein R7 is optionally substituted by one or more $R_e$;

$R_e$ is selected from the group consisting of a bond, C3–6 cycloalkyl, phenyl, naphthyl, thienyl, imidazolyl, pyrrolidinyl, piperidinyl, pyridinyl, indolyl, C1–5 alkoxy, benzyloxy, C1–3 alkanoylamino, methylthio wherein the sulfur atom may be oxidized to a sulfoxide or sulfone, benzylthio wherein the sulfur atom may be oxidized to a sulfoxide or sulfone, methoxycarbonylamino, amino wherein the nitrogen atom may be independently mono or di-substituted by C1–5 alkyl, halogen, hydroxy, carboxy and cyano, $R_e$ may be further optionally substituted by one or more $R_f$;

$R_f$ is selected from the group consisting of C1–5 alkyl, C3–6 cycloalkyl, phenyl optionally substituted by one or more groups selected from halogen or methyl, methoxy, phenoxy, benzyloxy, methoxycarbonyl, amino wherein the nitrogen atom may be independently mono or di-substituted by C1–3 alkyl or phenyl, halogen, hydroxy and carboxy;

R6 and R7 together with the carbon they are attached form a carbocyclic ring selected from the group consisting of cyclopropyl and cyclohexyl or heterocyclic ring selected from the group consisting of pyrrolidinyl and piperidinyl, the carbocyclic or heterocyclic ring being optionally substituted with one or more $R_g$;

$R_g$ is selected from the group consisting of a bond, C1–8 alkyl, C3–8 cycloalkyl, C7–8 bicycloalkyl, benzyl, tetrahydronaphthyl, indanyl, heterocyclyl selected from the group consisting of tetrahydropyranyl and tetrahydrothiopyranyl, acetyl, methoxycarbonyl, carbamoyl wherein the nitrogen atom may be independantly mono or disubstituted by C1–3 alkyl and amino wherein the nitrogen atom may be independently mono or di-substituted by C1–5 alkyl, C3–6 cycloalkyl, benzyl or benzoyl, $R_g$ may be further optionally substituted by one or more $R_h$; and $R_h$ is selected from the group consisting of C1–8 alkyl, C3–7 cycloalkyl, phenyl, benzyl, benzyloxy, heterocyclyl selected from the group consisting of piperidinyl, tetrahydropyranyl and tetrahydrothiopyranyl, heteroaryl selected from the group consisting of thienyl, pyridinyl, indolyl and benzimidazolyl, amino, methylamino, dimethylamino, halogen, hydroxy, oxo, cyano and trifluoromethyl.

15. The compound according to claim 14 wherein:

R1 is pyrrolidinyl, thiomorpholinyl or morpholinyl, wherein R1 is optionally substituted by one or more $R_a$;

$R_a$ is selected from the group consisting of a bond, C1–3 alkyl, pyrrolyl, imidazolyl, indolyl, benzimidazolyl, methoxy, methoxycarbonyl, t-butoxycarbonylamino, C1–3 alkylsulfonylamino, amino wherein the nitrogen atom may be independently mono or di-substituted by C1–3 alkyl, halogen, hydroxy, cyano and carboxy, $R_a$ may be further optionally substituted by one or more $R_b$;

$R_b$ is selected from the group consisting of methoxy, halogen and hydroxy;

$R_c$ is selected from the group consisting of a bond, methyl, C3–6 cycloalkyl, C7–8 bicycloalkyl, phenyl, naphthyl, tetrahydronaphthyl, indanyl, C1–4 alkoxy, C1–3 alkanoylamino, methylthio, halogen, hydroxy, oxo, carboxy and cyano, $R_c$ may be further optionally substituted by one or more $R_d$;

$R_d$ is selected from the group consisting of C1–3 alkyl, phenyl, methoxy, halogen and hydroxy;

R6 is hydrogen;

$R_e$ is selected from the group consisting of a bond, C5–6 cycloalkyl, phenyl, C1–5 alkoxy, C1–5 alkylamino, pyrrolidinyl, piperidinyl naphthyl, thienyl, indolyl, methoxy, benzyloxy, methylthio, benzylthio, methoxycarbonylamino, halogen, hydroxy, carboxy and cyano, $R_e$ may be further optionally substituted by one or more $R_f$; and $R_f$ is selected from the group consisting of C1–5 alkyl, C3–6 cycloalkyl, phenyl optionally substituted by halogen, methoxy, phenoxy, benzyloxy, methoxycarbonyl, halogen, hydroxy and carboxy;

R6 and R7 together with the carbon they are attached form a cyclopropyl ring or heterocyclic ring selected from the group consisting of pyrrolidinyl and piperidinyl, the cyclopropyl or heterocyclic ring being optionally substituted with one or more $R_g$;

$R_g$ is selected from the group consisting of a bond, C1–8 alkyl, C3–8 cycloalkyl, C7–8 bicycloalkyl, benzyl, -tetrahydronaphthyl, -indanyl, tetrahydropyranyl, tetrahydrothiopyranyl and amino wherein the nitrogen atom may be independently mono or di-substituted by C1–5 alkyl, C3–6 cycloalkyl, benzyl or benzoyl, $R_g$ may be further optionally substituted by one or more $R_h$; and $R_h$ is selected from the group consisting of C1–5 alkyl, C3–7 cycloalkyl, phenyl, benzyl, benzyloxy, tetrahydropyranyl, heteroaryl selected from the group consisting of thienyl, pyridinyl, indolyl, pyrrolyl and benzimidazolyl, halogen, hydroxy, oxo, cyano or trifluoromethyl, may be further substituted by $R_i$; and $R_i$ is C1–8 alkyl and halogen.

16. The compound according to claim 15 wherein:

R1 is morpholinyl, thiomorpholinyl or pyrrolidinyl R1 is optionally substituted by one or more $R_a$;

$R_a$ is selected from the group consisting of C1–3 alkyl, methoxy, C1–3 alkylsulfonylamino, halogen, hydroxy, cyano and trifluoromethyl;

R5 is C1–3 alkyl wherein R5 is optionally substituted by one or more $R_c$;

$R_c$ is selected from the group consisting of C3–6 cycloalkyl, C7–8 bicycloalkyl, phenyl, naphthyl, -tetrahydronaphthyl or -indanyl, $R_c$ may be further optionally substituted by one or more $R_d$;

$R_d$ is selected from the group consisting of methyl, methoxy and halogen;

R7 is C1–5 alkyl wherein R7 is optionally substituted by one or more $R_e$;

$R_e$ is selected from the group consisting of phenyl, naphthyl, C1–5 alkoxy, C1–5 alkylamino, pyrrolidinyl and piperidinyl, $R_e$ may be further optionally substituted by one or more $R_f$; and $R_f$ is selected from the group consisting of C1–5 alkyl, C3–6 cycloalkyl, phenyl optionally substituted with halogen, halogen and hydroxy;

or R6 and R7 together with the carbon they are attached form a cyclopropyl ring or heterocyclic ring selected from the group consisting of piperidinyl and pyrrolidinyl, the cyclopropyl or heterocyclic ring being optionally substituted with one or more $R_g$; and $R_g$ is selected from the group consisting of C1–8 alkyl, C3–8 cyclolyl, C7–8 bicycloalkyl, benzyl, -tetrahydimaphthyl, -indanyl, tetrahydropyranyl, tetrahydrothiopyranyl and amino group wherein the nitrogen atom may be independantly mono or disubstituted by C1–5 alkyl or C3–6 cycloalkyl, $R_g$ may be further optionally substituted by one or more $R_h$; and $R_h$ is selected from the group consisting of C1–5 alkyl, C3–7 cycloalkyl, phenyl, benzyl, benzyloxy, thienyl, pyrrolyl, indolyl, pyridinyl, halogen, hydroxy, cyano and trifluoromethyl;

$R_h$ may be further optionally substituted by one or more $R_i$; and $R_i$ is C1–5 alkyl and halogen.

17. The compound according to claim 16 wherein:

R1 is 4-morpholinyl or pyrrolidinyl, wherein R1 is optionally substituted by one or more $R_a$;

$R_a$ is C1–3 alkylsulfonylamino;

R5 is C1–3 alkyl wherein R5 is optionally substituted by one or more $R_c$;

$R_c$ is selected from the group consisting of C5–6 cycloalkyl, C7–8 bicycloalkyl, -tetrahydronaphthyl and -indanyl, $R_c$ may be further optionally substituted by one or more $R_d$;

$R_d$ is selected from the group consisting of methyl, methoxy and halogen;

R7 is C1–5 alkyl wherein R7 is optionally substituted by one or more $R_e$;

$R_e$ is selected from the group consisting of C1–5 alkoxy, C1–5 alkylamino, pyrrolidinyl and piperidinyl, $R_e$ may be further optionally substituted by one or more $R_f$; and $R_f$ is selected from the group consisting of C1–5 alkyl, C3–6 cycloalkyl, phenyl optionally substituted with halogen, halogen and hydroxy;

or R6 and R7 together with the carbon they are attached form heterocyclic ring selected from the group consisting of piperidinyl and pyrrolidinyl, the heterocyclic ring being optionally substituted with one or more $R_g$; and $R_g$ is selected from the group consisting of C1–8 alkyl, C3–8 cycloalkyl, C7–8 bicycloalkyl, benzyl, -tetrahydronaphthyl, -indanyl, tetrahydropyranyl and tetrahydrothiopyranyl; $R_g$ may be further optionally substituted by one or more $R_h$; and $R_h$ is selected from the group consisting of C1–5 alkyl, C3–7 cycloalkyl, phenyl, pyridinyl, indolyl, thienyl, halogen, hydroxy, cyano and trifluoromethyl; $R_h$ may be further optionally substituted by one or more $R_i$;

$R_i$ is selected from the group consisting of C1–3 alkyl and halogen.

18. The compound according to claim 17 wherein:

R1 is 4-morpholinyl;

R5 is C1–3 alkyl wherein R5 is optionally substituted by one or more $R_c$;

$R_c$ is selected from the group consisting of cyclohexyl, -tetrahydronaphthyl and -indanyl, $R_c$ may be further optionally substituted by one or more $R_d$;

$R_d$ is selected from the group consisting of methyl and halogen;

R7 is C1–5 alkyl wherein R7 is optionally substituted by one or more $R_e$;

$R_e$ is selected from the group consisting of C1–2 alkoxy and C1–2 alkylamino, $R_e$ may be further optionally substituted by one or more $R_f$;

$R_f$ is selected from the group consistng of C1–3 alkyl, phenyl, halogen and hydroxy;

or R6 and R7 together with the carbon they are attached form a heterocyclic ring selected from the group consisting of piperidinyl and pyrrolidinyl, the heterocyclic ring being optionally substituted with one or more $R_g$; and $R_g$ is selected from the group consisting of C1–5 alkyl, C3–8 cycloalkyl, C7–8 bicycloalkyl, benzyl and -tetrahydronaphthyl; $R_g$ may be further optionally substituted by one or more $R_h$; and $R_h$ is C1–5 alkyl, C3–7 cycloalkyl, thienyl, pyridinyl, indolyl, halogen, hydroxy and trifluoromethyl; $R_h$ may be further optionally substituted by one or more Ri;

Ri is methyl.

19. A pharmaceutical composition comprising a pharmaceutically effective amount of a compound according to claims 1 or 10.

20. A method of modulating an autoimmune disease, said method comprising administering to a patient in need of such treatment a pharmaceutically effect amount of a compound according to claim 1 or 10.

21. The method according to claim 20 wherein the autoimmune disease is selected from the group consisting of: rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, atopic dermatitis and insulin-dependent diabetes mellitus.

22. A method of treating Alzheimer's disease comprising administering to a patient in need of such treatment a pharmaceutically effective amount of a compound according to claim 1 or 10.

23. A method of treating atherosclerosis comprising administering to a patient in need of such treatment a pharmaceutically effective amount of a compound according to claim 1 or 10.

24. A method of making a compound of the formula (Ia) according to claim 10 comprising:

a) reacting a carboxylic acid compound shown below with an amine $R_1H$ in the presence of a coupling reagent selected from the group consisting of EDC and HOBT, in a suitable solvent;

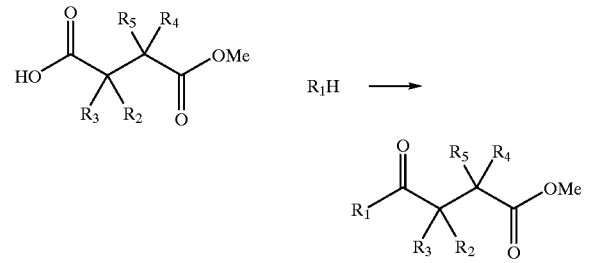

b) hydrolyzing the product of step a) with aqueous base or acid to produce:

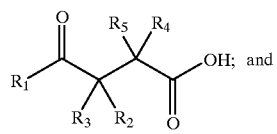

c) reacting the product of step b) with an amino nitrile compound shown below in the presence of EDC as a coupling reagent, in a suitable solvent,

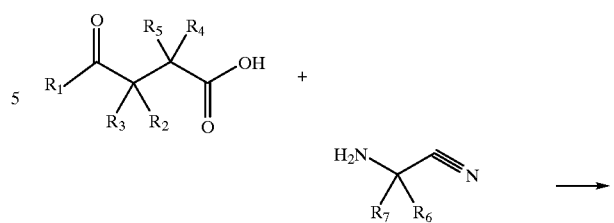

OR d) reacting the product of step b) with an amino amide compound shown below in the presence of EDC as a coupling reagent, in a suitable solvent followed by dehydration of the primary amide to yield a nitrile group

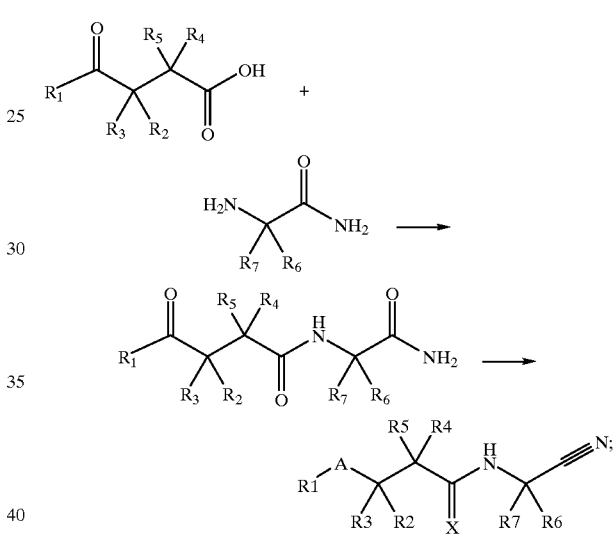

(Ia)

wherein X is O, R1 is an amino compound forming an amide bond with A, and R2, R3, R4, R5, R6, R7, and A are as defined in claim 10.

25. A method of making a compound of the formula (Ia) according to claim 10 comprising:

a) reacting an activated amide compound shown below with an aryl or heteroaryl organometallic reagant:

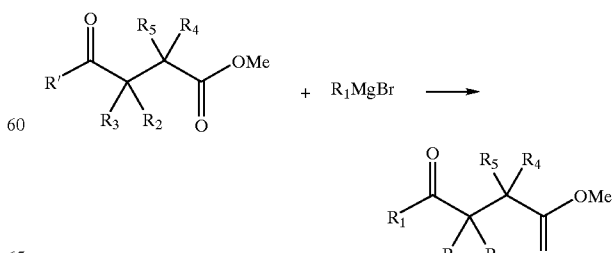

wherein R' is

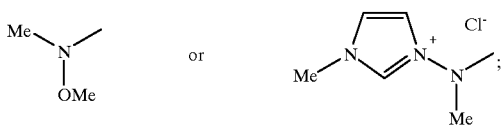

b) hydrolyzing the product of step a) with aqueous base or acid to produce:

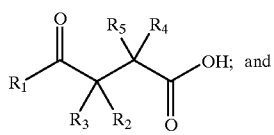

c) reacting the product of step b) with an amino nitrile compound shown below in the presence of EDC as a a coupling reagant, in a suitable solvent,

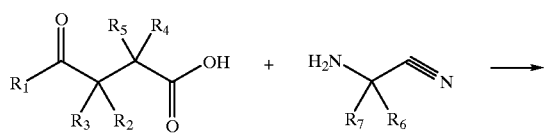

or d) reacting the product of step b) with an amino amide compound shown below in the presence of EDC as a coupling reagant, in a suitable solvent, followed by dehydration of the primary amide to yield a nitrile group,

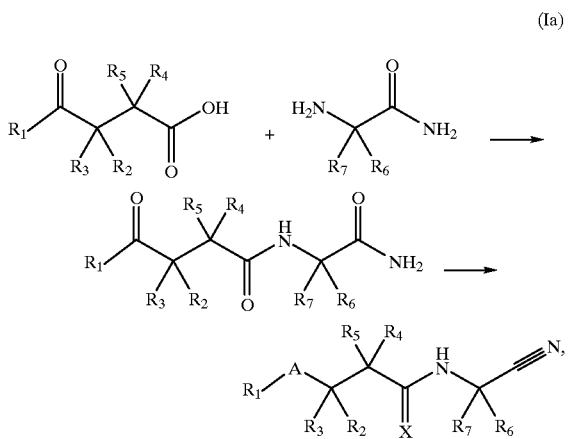

(Ia)

and optionally reducing the carbonyl group attached to R1, to produce a compound of the formula (Ia) wherein X is O, R1 is aryl, cycoalklyl, aryl or heteroaryl and R2, R3, R4, R5, R6, R7 and A are as defined in claim 10.

26. A compound selected from the group consisting of:
N-(Benzyloxymethyl-cyano-methyl)-2-cyclohexylmethyl-4-morpholin-4-yl-4-oxo-butyramide;
N-[2-(4-Chloro-benzyloxy)-1-cyano-ethyl]-2-cyclohexylmethyl-4-morpholin-4-yl-4-oxo-butyramide;
N-(cyano-1-benzyl-pyrrolidin-3-ylcarbamoyl)-2-cyclohexylmethyl-4-morpholin-4-yl-4-oxo-butyramide;
N-(3-Cyano-1-cyclohexylmethyl-pyrrolidin-3-yl)-2-cyclohexylmethyl-4-morpholin-4-yl-4-oxo-butyramide;
N-[3-Cyano-1-(2,6-difluoro-benzyl)-pyrrolidin-3-yl]-2-cyclohexylmethyl-4-morpholin-4-yl-4-oxo-butyramide;
N-[3-Cyano-1-(3,5-difluoro-benzyl)-pyrrolidin-3-yl]-2-cyclohexylmethyl-4-morpholin-4-yl-4-oxo-butyramide;
N-[3-Cyano-1-(3-trifluoromethyl-benzyl)-pyrrolidin-3-yl]-2-cyclohexylmethyl-4-morpholin-4-yl-4-oxo-butyramide;
N-(3-Cyano-1-cyclohexyl-pyrrolidin-3-yl)-2-cyclohexylmethyl-4-morpholin-4-yl-4-oxo-butyramide;
N-(3-cyano-1-(3,3-dimethyl-butyl)-pyrrolidin-3-ylcarbamoyl)-2-cyclohexylmethyl-4-morpholin-4-yl-4-oxo-butyramide;
N-(3-Cyano-1-isopropyl-pyrrolidin-3-yl)-2-cyclohexylmethyl-4-morpholin-4-yl-4-oxo-butyramide;
N-(3-Cyano-1-isobutyl-pyrrolidin-3-yl)-2-cyclohexylmethyl-4-morpholin-4-yl-4-oxo-butyramide;
N-(3-Cyano-1-cyclopropylmethyl-pyrrolidin-3-yl)-2-cyclohexylmethyl-4-morpholin-4-yl-4-oxo-butyramide;
N-(3-Cyano-1-phenethyl-pyrrolidin-3-yl)-2-cyclohexylmethyl-4-morpholin-4-yl-4-oxo-butyramide;
N-(3-Cyano-1-methyl-piperidin-3-yl)-2-cyclohexylmethyl-4-morpholin-4-yl-4-oxo-butyramide;
N-[3-Cyano-1-(4-methyl-cyclohexyl)-pyrrolidin-3-yl]-2-cyclohexylmethyl-4-morpholin-4-yl-4-oxo-butyramide;
N-(3-Cyano-1-propyl-pyrrolidin-3-yl)-2-cyclohexylmethyl-4-morpholin-4-yl-4-oxo-butyramide;
N-(3-Cyano-1-cyclopentyl-pyrrolidin-3-yl)-2-cyclohexylmethyl-4-morpholin-4-yl-4-oxo-butyramide;
N-[3-Cyano-1-(1H-indol-2-ylmethyl)-pyrrolidin-3-yl]-2-cyclohexylmethyl-4-morpholin-4-yl-4-oxo-butyramide;
N-(3-Cyano-1-cycloheptyl-pyrrolidin-3-yl)-2-cyclohexylmethyl-4-morpholin-4-yl-4-oxo-butyramide;
N-[3-Cyano-1-(1,2,3,4-tetrahydro-naphthalen-1-yl)-pyrrolidin-3-yl]-2-cyclohexylmethyl-4-morpholin-4-yl-4-oxo-butyramide;
N-(1-Bicyclo[2.2.1]hept-2-yl-3-cyano-pyrrolidin-3-yl)-2-cyclohexylmethyl-4-morpholin-4-yl-4-oxo-butyramide;
N-[3-Cyano-1-(tetrahydro-pyran-4-yl)-pyrrolidin-3-yl]-2-cyclohexylmethyl-4-morpholin-4-yl-4-oxo-butyramide;
N-[3-Cyano-1-(tetrahydro-thiopyran-4-yl)-pyrrolidin-3-yl]-2-cyclohexylmethyl-4-morpholin-4-yl-4-oxo-butyramide;
N-[3-Cyano-1-(tetrahydro-thiopyran-4-yl)-pyrrolidin-3-yl]-2-cyclohexylmethyl-4-morpholin-4-yl-4-oxo-butyramide;
(4R)-N-(3-Cyano-1-cyclohexyl-pyrrolidin-3-yl)-2-(4-methyl-cyclohexylmethyl)-4-morpholin-4-yl-4-oxo-butyramide;
2-Bicyclo[4.1.0]hept-7-ylmethyl-N-(3-cyano-1-cyclohexyl-pyrrolidin-3-yl)-4-morpholin-4-yl-4-oxo-butyramide;
N-(3-Cyano-1-cyclohexyl-pyrrolidin-3-yl)-4-morpholin-4-yl-4-oxo-2-(1,2,3,4-tetrahydro-naphthalen-2-ylmethyl)-butyramide;
N-(3-Cyano-1-cyclohexyl-pyrrolidin-3-yl)-2-indan-2-ylmethyl-4-morpholin-4-yl-4-oxo-butyramide;
N-(3-Cyano-1-cyclohexyl-pyrrolidin-3-yl)-2-cyclopentylmethyl-4-morpholin-4-yl-4-oxo-butyramide;
N-{Cyano-[(cyclohexyl-ethyl-amino)-methyl]-methyl}-2-cyclohexylmethyl-4-morpholin-4-yl-4-oxo-butyramide;
N-(Cyano-piperidin-1-ylmethyl-methyl)-2-cyclohexylmethyl-4-morpholin-4-yl-4-oxo-butyramide;
N-[(3S)-3-Cyano-1-trans-(4-ethyl-cyclohexyl)-pyrrolidin-3-yl]-(2R)-2-cyclohexylmethyl-4-morpholin-4-yl-4-oxo-butyramide;
N-[(3S)-3-Cyano-1-cis-(4-ethyl-cyclohexyl)-pyrrolidin-3-yl]-(2R)-2-cyclohexylmethyl-4-morpholin-4-yl-4-oxo-butyramide;

N-[(3S)-3-Cyano-1-trans-(4-isopropyl-cyclohexyl)-pyrrolidin-3-yl]-(2R)-2-cyclohexylmethyl-4-morpholin-4-yl-4-oxo-butyramide;

N-[(3S)-3-Cyano-1-cis-(4-isopropyl-cyclohexyl)-pyrrolidin-3-yl]-(2R)-2-cyclohexylmethyl-4-morpholin-4-yl-4-oxo-butyramide;

N-[1-trans-(4tert-Butyl-cyclohexyl)-(3S)-3-cyano-pyrrolidin-3-yl]-(2R)-2-cyclohexylmethyl-4-morpholin-4-yl-4-oxo-butyramide;

N-[(3S)-3-cyano-1-cis-(3-methyl-cyclohexyl)-pyrrolidin-3-yl]-(2R)-2-cyclohexylmethyl-4-morpholin-4-yl-4-oxo-butyramide;

N-[(3S)-3-cyano-1-trans-(3-methyl-cyclohexyl)-pyrrolidin-3-yl]-(2R)-2-cyclohexylmethyl-4-morpholin-4-yl-4-oxo-butyramide;

N-[(3R)-3-cyano-1-trans-(3-methyl-cyclohexyl)-pyrrolidin-3-yl]-(2R)-2-cyclohexylmethyl-4-morpholin-4-yl-4-oxo-butyramide;

N-[(3S)-3-Cyano-1-(3,3-dimethyl-cyclohexyl)-pyrrolidin-3-yl]-(2R)-2-cyclohexylmethyl-4-morpholin-4-yl-4-oxo-butyramide;

N-[(3R)-3-Cyano-1-(3,3-dimethyl-cyclohexyl)-pyrrolidin-3-yl]-(2R)-2-cyclohexylmethyl-4-morpholin-4-yl-4-oxo-butyramide;

N-[(3S)-3-Cyano-1-cis-(3-isopropyl-cyclohexyl)-pyrrolidin-3-yl]-(2R)-2-cyclohexylmethyl-4-morpholin-4-yl-4-oxo-butyramide;

N-[(3S)-3-Cyano-1-trans-(3-isopropyl-cyclohexyl)-pyrrolidin-3-yl]-(2R)-2-cyclohexylmethyl-4-morpholin-4-yl-4-oxo-butyramide;

N-[(3R)-3-Cyano-1-trans-(3-isopropyl-cyclohexyl)-pyrrolidin-3-yl]-(2R)-2-cyclohexylmethyl-4-morpholin-4-yl-4-oxo-butyramide;

N-[(3S)-3-Cyano-1-cis-(2-methyl-cyclohexyl)-pyrrolidin-3-yl]-(2R)-2-cyclohexylmethyl-4-morpholin-4-yl-4-oxo-butyramide;

N-[(3S)-3-Cyano-1-trans-(2-methyl-cyclohexyl)-pyrrolidin-3-yl]-(2R)-2-cyclohexylmethyl-4-morpholin-4-yl-4-oxo-butyramide;

N-[(3S)-3-Cyano-1-cis-(2-ethyl-cyclohexyl)-pyrtolidin-3-yl]-(2R)-2-cyclohexylmethyl-4-morpholin-4-yl-4-oxo-butyramide;

N-[(3S)-3-Cyano-1-trans-(2-ethyl-cyclohexyl)-pyrrolidin-3-yl]-(2R)-2-cyclohexylmethyl-4-morpholin-4-yl-4-oxo-butyramide;

N-[(3S)-3-Cyano-1-(2,2-dimethyl-cyclohexyl)-pyrrolidin-3-yl]-(2R)-2-cyclohexylmethyl-4-morpholin-4-yl-4-oxo-butyramide;

N-[(3S)-3-Cyano-1-(4,4-dimethyl-cyclohexyl)-pyrrolidin-3-yl]-(2R)-2-cyclohexylmethyl-4-morpholin-4-yl-4-oxo-butyramide;

N-[(3S)-3-Cyano-1-(2-methyl-2-phenyl-propyl)-pyrrolidin-3-yl]-(2R)-2-cyclohexylmethyl-4-morpholin-4-yl-4-oxo-butyramide;

N-[(3R)-3-Cyano-1-(2-methyl-2-phenyl-propyl)-pyrrolidin-3-yl]-(2R)-2-cyclohexylmethyl-4-morpholin-4-yl-4-oxo-butyramide;

N-[(3S)-3-Cyano-1-indan-2-ylmethyl-pyrrolidin-3-yl]-(2R)-2-cyclohexylmethyl-4-morpholin-4-yl-4-oxo-butyramide;

N-[(3S)-3-Cyano-1-(5-methyl-thiophen-2-ylmethyl)-pyrrolidin-3-yl]-(2S)-2-cyclohexylmethyl-4-morpholin-4-yl-4-oxo-butyramide and the pharmaceutically acceptable salts, esters or tautomers thereof.

27. The compound according to claim 26 wherein the compound is selected from the group consisting of:

N-(cyano-1-benzyl-pyrrolidin-3-ylcarbamoyl)-2-cyclohexylmethyl-4-morpholin-4-yl-4-oxo-butyramide;

N-(3-Cyano-1-cyclohexyl-pyrrolidin-3-yl)-2-cyclohexylmethyl-4-morpholin-4-yl-4-oxo-butyramide;

N-(3-Cyano-1-cyclopropylmethyl-pyrrolidin-3-yl)-2-cyclohexylmethyl-4-morpholin-4-yl-4-oxo-butyramide;

N-(3-Cyano-1-phenethyl-pyrrolidin-3-yl)-2-cyclohexylmethyl-4-morpholin-4-yl-4-oxo-butyramide;

N-[3-Cyano-1-(4-methyl-cyclohexyl)-pyrrolidin-3-yl]-2-cyclohexylmethyl-4-morpholin-4-yl-4-oxo-butyramide;

(4R)-N-(3-Cyano-1-cyclohexyl-pyrrolidin-3-yl)-2-(4-methyl-cyclohexylmethyl)-4-morpholin-4-yl-4-oxo-butyramide;

N-(3-Cyano-1-cyclohexyl-pyrrolidin-3-yl)-4-morpholin-4-yl-4-oxo-2-(1,2,3,4-tetrahydro-naphthalen-2-ylmethyl)-butyramide;

N-[(3S)-3-Cyano-1-trans-(4-ethyl-cyclohexyl)-pyrrolidin-3-yl]-(2R)-2-cyclohexylmethyl-4-morpholin-4-yl-4-oxo-butyramide;

N-[(3S)-3-cyano-1-trans-(3-methyl-cyclohexyl)-pyrrolidin-3-yl]-(2R)-2-cyclohexylmethyl-4-morpholin-4-yl-4-oxo-butyramide;

N-[(3R)-3-cyano-1-trans-(3-methyl-cyclohexyl)-pyrrolidin-3-yl]-(2R)-2-cyclohexylmethyl-4-morpholin-4-yl-4-oxo-butyramide and N-[(3S)-3-Cyano-1-(3,3-dimethyl-cyclohexyl)-pyrrolidin-3-yl]-(2R)-2-cyclohexylmethyl-4-morpholin-4-yl-4-oxo-butyramide.

* * * * *